(12) United States Patent
Metzger et al.

(10) Patent No.: US 10,206,697 B2
(45) Date of Patent: Feb. 19, 2019

(54) PATIENT-SPECIFIC KNEE ALIGNMENT GUIDE AND ASSOCIATED METHOD

(71) Applicant: Biomet Manufacturing, LLC, Warsaw, IN (US)

(72) Inventors: Robert Metzger, Wakarusa, IN (US); Keith R. Berend, Columbus, OH (US); Michael E. Berend, Indianapolis, IN (US); Adolph V. Lombardi, Jr., New Albany, OH (US); Lance Dean Perry, Warsaw, IN (US); Ryan John Schoenefeld, Fort Wayne, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 15/712,679

(22) Filed: Sep. 22, 2017

(65) Prior Publication Data
US 2018/0008292 A1  Jan. 11, 2018

Related U.S. Application Data

(60) Continuation of application No. 14/327,234, filed on Jul. 9, 2014, now Pat. No. 9,795,399, which is a (Continued)

(51) Int. Cl.
*A61F 5/00* (2006.01)
*A61B 17/17* (2006.01)
(Continued)

(52) U.S. Cl.
CPC ........ *A61B 17/1764* (2013.01); *A61B 17/154* (2013.01); *A61B 34/10* (2016.02);
(Continued)

(58) Field of Classification Search
None
See application file for complete search history.

(56) References Cited

U.S. PATENT DOCUMENTS 1,480,285 A   1/1924   Moore
1,763,730 A   6/1930   Lackum
(Continued)

FOREIGN PATENT DOCUMENTS

CA   2447694 A1   12/2002
CA   2501041 A1    4/2004
(Continued)

OTHER PUBLICATIONS

"U.S. Appl. No. 12/371,096, Corrected Notice of Allowance dated Nov. 13, 2017", 2 pgs.
(Continued)

*Primary Examiner* — Sameh Boles
(74) *Attorney, Agent, or Firm* — Schwegman Lundberg & Woessner, P.A.

(57) ABSTRACT

A method of preparing a knee joint for a prosthesis in a patient includes mating a patient-specific three-dimensional curved inner surface of a femoral alignment guide onto a corresponding three-dimensional femoral joint surface of the patient. The patient-specific three-dimensional curved inner surface is preoperatively configured from medical scans of the knee joint of the patient. First and second holes are drilled into an anterior portion of the femoral joint surface through corresponding first and second guiding apertures of the femoral alignment guide.

20 Claims, 16 Drawing Sheets

Related U.S. Application Data continuation-in-part of application No. 13/800,334, filed on Mar. 13, 2013, now Pat. No. 9,861,387, which is a division of application No. 13/303,546, filed on Nov. 23, 2011, now Pat. No. 8,398,646, which is a continuation of application No. 11/756,057, filed on May 31, 2007, now Pat. No. 8,092,465.

(60) Provisional application No. 60/812,694, filed on Jun. 9, 2006.

(51) Int. Cl.
  *A61B 17/15* (2006.01)
  *A61B 34/10* (2016.01)

(52) U.S. Cl.
  CPC .......... *A61B 17/155* (2013.01); *A61B 17/157* (2013.01); *A61B 2034/108* (2016.02)

(56) References Cited

U.S. PATENT DOCUMENTS

| | | |
|---|---|---|
| 1,959,615 A | 5/1934 | Derrah |
| 2,181,746 A | 11/1939 | Siebrandt |
| 2,407,845 A | 9/1946 | Orisan |
| 2,416,228 A | 2/1947 | Sheppard |
| 2,433,815 A | 12/1947 | Nicephore |
| 2,455,655 A | 12/1948 | Carroll |
| 2,618,913 A | 11/1952 | Plancon et al. |
| 2,702,550 A | 2/1955 | Rowe |
| 2,724,326 A | 11/1955 | Long |
| 2,910,978 A | 11/1959 | Urist |
| 2,955,530 A | 10/1960 | Nilo |
| 3,048,522 A | 8/1962 | Velley |
| 3,229,006 A | 1/1966 | Egon |
| 3,229,372 A | 1/1966 | Quashnock et al. |
| 3,330,611 A | 7/1967 | Heifetz |
| 3,514,791 A | 6/1970 | Sparks |
| 3,554,197 A | 1/1971 | Dobbie |
| 3,624,747 A | 11/1971 | Mcknight et al. |
| 3,631,596 A | 1/1972 | Glaus |
| 3,678,934 A | 7/1972 | Warfield et al. |
| 3,698,017 A | 10/1972 | Scales et al. |
| 3,703,036 A | 11/1972 | Karubian |
| 3,774,244 A | 11/1973 | Walker |
| 3,783,873 A | 1/1974 | Jacobs |
| 3,807,393 A | 4/1974 | Mc |
| 3,811,449 A | 5/1974 | Gravlee et al. |
| 3,840,904 A | 10/1974 | Tronzo |
| 3,869,731 A | 3/1975 | Waugh et al. |
| 3,903,549 A | 9/1975 | Deyerle |
| 3,905,105 A | 9/1975 | Tuke |
| 3,905,374 A | 9/1975 | Winter |
| 3,911,923 A | 10/1975 | Yoon |
| 3,913,585 A | 10/1975 | Wolvek |
| 3,920,022 A | 11/1975 | Pastor |
| 3,941,127 A | 3/1976 | Froning |
| 3,967,625 A | 7/1976 | Yoon et al. |
| 3,975,858 A | 8/1976 | Much |
| 3,989,049 A | 11/1976 | Yoon |
| 3,991,426 A | 11/1976 | Flom et al. |
| 3,994,287 A | 11/1976 | Turp et al. |
| 4,053,953 A | 10/1977 | Flom et al. |
| 4,055,862 A | 11/1977 | Farling |
| 4,081,866 A | 4/1978 | Upshaw et al. |
| 4,085,466 A | 4/1978 | Goodfellow et al. |
| 4,085,743 A | 4/1978 | Yoon |
| 4,103,680 A | 8/1978 | Yoon |
| 4,246,895 A | 1/1981 | Rehder |
| 4,299,224 A | 11/1981 | Noiles |
| 4,304,178 A | 12/1981 | Haberle |
| 4,306,866 A | 12/1981 | Weissman |
| 4,311,145 A | 1/1982 | Esty et al. |
| 4,324,006 A | 4/1982 | Charnley |
| 4,344,193 A | 8/1982 | Kenny |
| 4,349,018 A | 9/1982 | Chamber |
| 4,373,709 A | 2/1983 | Whitt et al. |
| 4,374,523 A | 2/1983 | Yoon |
| 4,385,404 A | 5/1983 | Sully et al. |
| 4,386,609 A | 6/1983 | Mongeon |
| 4,400,833 A | 8/1983 | Kurland |
| 4,421,112 A | 12/1983 | Mains et al. |
| 4,428,571 A | 1/1984 | Sugarman |
| 4,436,684 A | 3/1984 | White |
| D273,895 S | 5/1984 | Kenna et al. |
| D274,091 S | 5/1984 | Kenna |
| 4,453,421 A | 6/1984 | Umano |
| 4,457,306 A | 7/1984 | Borzone |
| 4,475,549 A | 10/1984 | Oh |
| 4,501,269 A | 2/1985 | Bagby |
| 4,506,393 A | 3/1985 | Murphy |
| 4,509,518 A | 4/1985 | Mcgarry et al. |
| 4,516,276 A | 5/1985 | Mittelmeier |
| 4,524,766 A | 6/1985 | Petersen |
| 4,528,980 A | 7/1985 | Kenna |
| 4,534,365 A | 8/1985 | Bonetta et al. |
| 4,535,773 A | 8/1985 | Yoon |
| 4,545,375 A | 10/1985 | Cline |
| 4,554,686 A | 11/1985 | Baker |
| 4,562,598 A | 1/1986 | Kranz |
| 4,565,191 A | 1/1986 | Slocum |
| 4,565,192 A | 1/1986 | Shapiro |
| 4,567,886 A | 2/1986 | Petersen |
| 4,574,794 A | 3/1986 | Cooke et al. |
| 4,619,391 A | 10/1986 | Sharkany et al. |
| 4,619,658 A | 10/1986 | Pappas et al. |
| 4,621,630 A | 11/1986 | Kenna |
| 4,624,254 A | 11/1986 | Mcgarry et al. |
| 4,632,111 A | 12/1986 | Roche |
| 4,633,862 A | 1/1987 | Petersen |
| 4,641,648 A | 2/1987 | Shapiro |
| 4,642,120 A | 2/1987 | Nevo et al. |
| 4,646,729 A | 3/1987 | Kenna et al. |
| 4,662,372 A | 5/1987 | Sharkany et al. |
| 4,663,720 A | 5/1987 | Duret et al. |
| 4,678,470 A | 7/1987 | Nashef et al. |
| 4,682,598 A | 7/1987 | Beraha |
| 4,685,460 A | 8/1987 | Thornton |
| 4,689,984 A | 9/1987 | Kellner |
| 4,695,283 A | 9/1987 | Aldinger |
| 4,696,292 A | 9/1987 | Heiple |
| 4,703,751 A | 11/1987 | Pohl |
| 4,704,686 A | 11/1987 | Aldinger |
| 4,706,660 A | 11/1987 | Petersen |
| 4,711,233 A | 12/1987 | Brown |
| 4,715,860 A | 12/1987 | Amstutz et al. |
| 4,718,413 A | 1/1988 | Johnson |
| 4,718,916 A | 1/1988 | Morscher |
| 4,719,907 A | 1/1988 | Banko et al. |
| 4,721,104 A | 1/1988 | Kaufman et al. |
| 4,722,330 A | 2/1988 | Russell et al. |
| 4,739,751 A | 4/1988 | Sapega et al. |
| 4,759,350 A | 7/1988 | Dunn et al. |
| 4,778,474 A | 10/1988 | Homsy |
| 4,794,854 A | 1/1989 | Swaim |
| 4,800,874 A | 1/1989 | David et al. |
| 4,817,602 A | 4/1989 | Beraha |
| 4,821,213 A | 4/1989 | Cline et al. |
| 4,822,365 A | 4/1989 | Walker et al. |
| 4,834,757 A | 5/1989 | Brantigan |
| 4,838,891 A | 6/1989 | Branemark et al. |
| 4,841,975 A | 6/1989 | Woolson |
| 4,846,161 A | 7/1989 | Roger |
| 4,863,472 A | 9/1989 | Tormala et al. |
| 4,871,975 A | 10/1989 | Nawata et al. |
| 4,888,022 A | 12/1989 | Huebsch |
| 4,892,545 A | 1/1990 | Day et al. |
| 4,893,619 A | 1/1990 | Dale et al. |
| 4,896,663 A | 1/1990 | Vandewalls |
| 4,907,577 A | 3/1990 | Wu |
| 4,911,721 A | 3/1990 | Andergaten |
| 4,927,422 A | 5/1990 | Engelhardt |
| 4,935,023 A | 6/1990 | Whiteside et al. |
| 4,936,852 A | 6/1990 | Kent et al. |

(56) References Cited

U.S. PATENT DOCUMENTS

| | | |
|---|---|---|
| 4,936,862 A | 6/1990 | Walker et al. |
| 4,950,296 A | 8/1990 | Mcintyre |
| 4,952,213 A | 8/1990 | Bowman et al. |
| 4,959,066 A | 9/1990 | Dunn et al. |
| 4,961,740 A | 10/1990 | Ray et al. |
| 4,961,954 A | 10/1990 | Goldberg et al. |
| 4,964,865 A | 10/1990 | Burkhead et al. |
| 4,976,737 A | 12/1990 | Leake |
| 4,979,949 A | 12/1990 | Matsen, III et al. |
| 4,979,957 A | 12/1990 | Hodorek |
| 4,985,037 A | 1/1991 | Petersen |
| 4,985,038 A | 1/1991 | Lyell |
| 4,994,064 A | 2/1991 | Aboczky |
| 5,002,579 A | 3/1991 | Copf et al. |
| 5,006,121 A | 4/1991 | Hafeli |
| 5,007,912 A | 4/1991 | Albrektsson et al. |
| 5,007,936 A | 4/1991 | Woolson |
| 5,015,247 A | 5/1991 | Michelson |
| 5,019,105 A | 5/1991 | Wiley |
| 5,030,219 A | 7/1991 | Matsen et al. |
| 5,030,221 A | 7/1991 | Buechel et al. |
| 5,032,132 A | 7/1991 | Matsen, III et al. |
| 5,035,700 A | 7/1991 | Kenna |
| 5,037,424 A | 8/1991 | Aboczsky |
| 5,041,117 A | 8/1991 | Engelhardt |
| 5,053,037 A | 10/1991 | Lackey et al. |
| 5,053,039 A | 10/1991 | Hofmann et al. |
| 5,056,351 A | 10/1991 | Stiver et al. |
| 5,060,678 A | 10/1991 | Bauman et al. |
| 5,061,270 A | 10/1991 | Aboczky |
| 5,061,286 A | 10/1991 | Lyle |
| 5,062,843 A | 11/1991 | Mahony, III |
| 5,073,373 A | 12/1991 | O'Leary et al. |
| 5,082,670 A | 1/1992 | Gage et al. |
| 5,084,050 A | 1/1992 | Draenert |
| 5,086,401 A | 2/1992 | Glassman et al. |
| 5,092,869 A | 3/1992 | Waldron |
| 5,098,383 A | 3/1992 | Hemmy et al. |
| 5,098,436 A | 3/1992 | Ferrante et al. |
| 5,098,437 A | 3/1992 | Kashuba et al. |
| 5,099,859 A | 3/1992 | Bell |
| 5,100,689 A | 3/1992 | Goldberg et al. |
| 5,101,720 A | 4/1992 | Bianchi |
| 5,108,425 A | 4/1992 | Hwang |
| 5,108,441 A | 4/1992 | Mcdowell |
| 5,111,987 A | 5/1992 | Moeinzadeh et al. |
| 5,122,144 A | 6/1992 | Bert et al. |
| 5,123,906 A | 6/1992 | Kelman |
| 5,123,927 A | 6/1992 | Duncan et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,141,512 A | 8/1992 | Farmer et al. |
| 5,147,365 A | 9/1992 | Whitlock et al. |
| 5,150,304 A | 9/1992 | Berchem et al. |
| 5,152,744 A | 10/1992 | Krause et al. |
| 5,152,778 A | 10/1992 | Bales, Jr. et al. |
| 5,154,717 A | 10/1992 | Matsen, III et al. |
| 5,162,506 A | 11/1992 | Hadden |
| 5,163,949 A | 11/1992 | Bonutti |
| 5,170,800 A | 12/1992 | Smith et al. |
| 5,171,243 A | 12/1992 | Kashuba et al. |
| 5,171,244 A | 12/1992 | Caspari et al. |
| 5,171,276 A | 12/1992 | Caspari et al. |
| 5,174,300 A | 12/1992 | Bales et al. |
| 5,176,684 A | 1/1993 | Ferrante et al. |
| 5,176,702 A | 1/1993 | Bales et al. |
| 5,176,711 A | 1/1993 | Grimes |
| 5,178,622 A | 1/1993 | Lehner, II |
| 5,183,053 A | 2/1993 | Yeh |
| 5,183,464 A | 2/1993 | Dubrul et al. |
| 5,186,178 A | 2/1993 | Yeh |
| 5,192,327 A | 3/1993 | Brantigan |
| 5,194,066 A | 3/1993 | Van Zile |
| 5,197,968 A | 3/1993 | Clement |
| 5,197,971 A | 3/1993 | Bonutti |
| 5,197,987 A | 3/1993 | Koch et al. |
| 5,204,106 A | 4/1993 | Schepers et al. |
| 5,207,680 A | 5/1993 | Dietz et al. |
| 5,207,692 A | 5/1993 | Kraus et al. |
| 5,217,463 A | 6/1993 | Mikhail |
| 5,222,984 A | 6/1993 | Forte |
| 5,228,459 A | 7/1993 | Caspari et al. |
| 5,234,433 A | 8/1993 | Bert et al. |
| 5,242,448 A | 9/1993 | Pettine et al. |
| 5,246,444 A | 9/1993 | Schreiber |
| 5,253,506 A | 10/1993 | Davis et al. |
| 5,258,004 A | 11/1993 | Bales et al. |
| 5,258,032 A | 11/1993 | Bertin |
| 5,261,915 A | 11/1993 | Durlacher et al. |
| 5,263,498 A | 11/1993 | Caspari et al. |
| 5,263,987 A | 11/1993 | Shah |
| 5,269,785 A | 12/1993 | Bonutti |
| 5,273,524 A | 12/1993 | Fox et al. |
| 5,274,565 A | 12/1993 | Reuben |
| D343,247 S | 1/1994 | Walen |
| 5,275,166 A | 1/1994 | Vaitekunas et al. |
| 5,275,603 A | 1/1994 | Ferrante et al. |
| 5,282,802 A | 2/1994 | Mahony, III |
| 5,282,803 A | 2/1994 | Lackey |
| 5,285,773 A | 2/1994 | Bonutti et al. |
| 5,293,878 A | 3/1994 | Bales et al. |
| 5,295,994 A | 3/1994 | Bonutti |
| 5,299,288 A | 3/1994 | Glassman et al. |
| 5,300,077 A | 4/1994 | Howell |
| 5,304,181 A | 4/1994 | Caspari et al. |
| 5,306,285 A | 4/1994 | Miller et al. |
| 5,308,349 A | 5/1994 | Mikhail |
| 5,314,482 A | 5/1994 | Goodfellow et al. |
| 5,320,529 A | 6/1994 | Pompa |
| 5,320,625 A | 6/1994 | Bertin |
| 5,322,505 A | 6/1994 | Krause et al. |
| 5,323,697 A | 6/1994 | Schrock |
| 5,329,845 A | 7/1994 | Bichel |
| 5,342,366 A | 8/1994 | Whiteside et al. |
| 5,342,367 A | 8/1994 | Ferrante et al. |
| 5,342,368 A | 8/1994 | Petersen |
| 5,344,423 A | 9/1994 | Dietz et al. |
| 5,344,458 A | 9/1994 | Bonutti |
| 5,348,541 A | 9/1994 | Bonutti |
| 5,360,446 A | 11/1994 | Kennedy |
| 5,364,402 A | 11/1994 | Mumme et al. |
| 5,368,599 A | 11/1994 | Hirsch et al. |
| 5,368,858 A | 11/1994 | Hunziker |
| 5,370,692 A | 12/1994 | Fink et al. |
| 5,370,699 A | 12/1994 | Hood et al. |
| 5,379,133 A | 1/1995 | Kirk |
| 5,382,249 A | 1/1995 | Fletcher et al. |
| 5,383,937 A | 1/1995 | Mikhail |
| 5,390,683 A | 2/1995 | Pisharodi |
| 5,395,376 A | 2/1995 | Pisharodi |
| 5,405,395 A | 4/1995 | Coates |
| 5,408,409 A | 4/1995 | Glassman et al. |
| D358,647 S | 5/1995 | Cohen et al. |
| 5,411,521 A | 5/1995 | Putnam et al. |
| 5,415,662 A | 5/1995 | Ferrante et al. |
| 5,417,694 A | 5/1995 | Marik et al. |
| 5,423,827 A | 6/1995 | Mumme et al. |
| 5,425,355 A | 6/1995 | Kulick |
| 5,425,745 A | 6/1995 | Green et al. |
| 5,438,263 A | 8/1995 | Dworkin et al. |
| 5,440,496 A | 8/1995 | Andersson et al. |
| 5,443,475 A | 8/1995 | Auerbach et al. |
| 5,445,639 A | 8/1995 | Kuslich et al. |
| 5,445,642 A | 8/1995 | McNulty et al. |
| 5,448,489 A | 9/1995 | Reuben |
| 5,449,360 A | 9/1995 | Schreiber |
| 5,452,407 A | 9/1995 | Crook |
| 5,454,365 A | 10/1995 | Bonutti |
| 5,454,815 A | 10/1995 | Geisser et al. |
| 5,454,816 A | 10/1995 | Ashby |
| 5,456,268 A | 10/1995 | Bonutti |
| 5,462,550 A | 10/1995 | Dietz et al. |

(56) References Cited

U.S. PATENT DOCUMENTS

| | | |
|---|---|---|
| 5,472,415 A | 12/1995 | King et al. |
| 5,474,559 A | 12/1995 | Bertin et al. |
| 5,484,095 A | 1/1996 | Green et al. |
| 5,486,178 A | 1/1996 | Hodge |
| 5,490,854 A | 2/1996 | Fisher et al. |
| 5,496,324 A | 3/1996 | Barnes |
| 5,497,933 A | 3/1996 | Defonzo et al. |
| 5,507,763 A | 4/1996 | Petersen et al. |
| 5,507,833 A | 4/1996 | Bohn |
| 5,514,139 A | 5/1996 | Goldstein et al. |
| 5,514,143 A | 5/1996 | Bonutti et al. |
| 5,514,519 A | 5/1996 | Neckers |
| 5,520,692 A | 5/1996 | Ferrante |
| 5,520,694 A | 5/1996 | Dance et al. |
| 5,520,695 A | 5/1996 | Luckman |
| 5,522,897 A | 6/1996 | King et al. |
| 5,527,317 A | 6/1996 | Ashby et al. |
| 5,539,649 A | 7/1996 | Walsh et al. |
| 5,540,695 A | 7/1996 | Levy |
| 5,545,222 A | 8/1996 | Bonutti |
| 5,546,720 A | 8/1996 | Labruzza |
| 5,549,683 A | 8/1996 | Bonutti |
| 5,549,688 A | 8/1996 | Ries et al. |
| 5,554,169 A | 9/1996 | Green et al. |
| 5,554,190 A | 9/1996 | Draenert |
| 5,560,096 A | 10/1996 | Stephens |
| 5,560,728 A | 10/1996 | Mcfadden |
| 5,562,675 A | 10/1996 | Mcnulty et al. |
| 5,569,163 A | 10/1996 | Francis et al. |
| 5,569,261 A | 10/1996 | Marik et al. |
| 5,570,700 A | 11/1996 | Vogeler |
| 5,571,110 A | 11/1996 | Matsen, III et al. |
| 5,571,111 A | 11/1996 | Aboczky |
| 5,578,037 A | 11/1996 | Sanders et al. |
| 5,578,039 A | 11/1996 | Vendrely et al. |
| 5,586,558 A | 12/1996 | Riley |
| 5,593,411 A | 1/1997 | Stalcup et al. |
| 5,593,448 A | 1/1997 | Dong |
| 5,595,703 A | 1/1997 | Swaelens et al. |
| 5,597,379 A | 1/1997 | Haines et al. |
| 5,601,565 A | 2/1997 | Huebner |
| 5,607,431 A | 3/1997 | Dudasik et al. |
| 5,608,052 A | 3/1997 | Zmitek et al. |
| 5,609,603 A | 3/1997 | Linden |
| 5,611,802 A | 3/1997 | Samuelson et al. |
| 5,613,969 A | 3/1997 | Jenkins, Jr. |
| 5,616,147 A | 4/1997 | Gadelius |
| 5,620,448 A | 4/1997 | Puddu |
| 5,624,444 A | 4/1997 | Wixon et al. |
| 5,624,463 A | 4/1997 | Stone et al. |
| 5,632,745 A | 5/1997 | Schwartz |
| 5,634,927 A | 6/1997 | Houston et al. |
| 5,641,323 A | 6/1997 | Caldarise |
| 5,643,272 A | 7/1997 | Haines et al. |
| 5,649,946 A | 7/1997 | Bramlet |
| 5,649,947 A | 7/1997 | Auerbach et al. |
| 5,653,714 A | 8/1997 | Dietz et al. |
| 5,658,294 A | 8/1997 | Sederholm |
| 5,659,947 A | 8/1997 | Eilers et al. |
| 5,662,656 A | 9/1997 | White |
| 5,662,710 A | 9/1997 | Bonutti |
| 5,667,069 A | 9/1997 | Williams, Jr. |
| 5,667,511 A | 9/1997 | Vendrely et al. |
| 5,667,512 A | 9/1997 | Johnson |
| 5,667,520 A | 9/1997 | Bonutti |
| 5,671,018 A | 9/1997 | Ohara et al. |
| D385,163 S | 10/1997 | Hutchins et al. |
| 5,676,668 A | 10/1997 | McCue et al. |
| 5,677,107 A | 10/1997 | Neckers |
| 5,681,316 A | 10/1997 | DeOrio et al. |
| 5,681,354 A | 10/1997 | Eckhoff |
| 5,682,886 A | 11/1997 | Delp et al. |
| 5,683,398 A | 11/1997 | Carls et al. |
| 5,683,469 A | 11/1997 | Johnson et al. |
| 5,688,279 A | 11/1997 | McNulty et al. |
| 5,688,280 A | 11/1997 | Booth, Jr. et al. |
| 5,690,635 A | 11/1997 | Matsen, III et al. |
| 5,694,693 A | 12/1997 | Hutchins et al. |
| 5,697,933 A | 12/1997 | Gundlapalli et al. |
| 5,702,447 A | 12/1997 | Walch et al. |
| 5,702,460 A | 12/1997 | Carls et al. |
| 5,702,464 A | 12/1997 | Lackey et al. |
| 5,702,475 A | 12/1997 | Zahedi |
| 5,704,941 A | 1/1998 | Jacober et al. |
| 5,707,350 A | 1/1998 | Krause et al. |
| 5,709,689 A | 1/1998 | Ferrante et al. |
| 5,712,543 A | 1/1998 | Sjostrom |
| 5,716,360 A | 2/1998 | Baldwin et al. |
| 5,718,708 A | 2/1998 | Webb |
| 5,720,752 A | 2/1998 | Elliot et al. |
| 5,722,978 A | 3/1998 | Jenkins, Jr. |
| 5,723,331 A | 3/1998 | Tubo et al. |
| 5,725,376 A | 3/1998 | Poirier |
| 5,725,592 A | 3/1998 | White et al. |
| 5,725,593 A | 3/1998 | Caracciolo |
| 5,728,128 A | 3/1998 | Crickenberger et al. |
| 5,733,292 A | 3/1998 | Gustilo et al. |
| 5,735,277 A | 4/1998 | Schuster |
| 5,745,834 A | 4/1998 | Bampton et al. |
| 5,748,767 A | 5/1998 | Raab |
| 5,749,875 A | 5/1998 | Puddu |
| 5,749,876 A | 5/1998 | Duvillier et al. |
| 5,755,731 A | 5/1998 | Grinberg |
| 5,755,791 A | 5/1998 | Whitson et al. |
| 5,755,803 A | 5/1998 | Haines et al. |
| 5,762,125 A | 6/1998 | Mastrorio |
| 5,766,251 A | 6/1998 | Koshino |
| 5,768,134 A | 6/1998 | Swaelens et al. |
| 5,769,092 A | 6/1998 | Williamson, Jr. |
| 5,769,855 A | 6/1998 | Bertin et al. |
| 5,769,899 A | 6/1998 | Schwartz et al. |
| 5,772,594 A | 6/1998 | Barrick |
| 5,776,200 A | 7/1998 | Johnson et al. |
| 5,786,217 A | 7/1998 | Tubo et al. |
| 5,788,700 A | 8/1998 | Morawa et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,810,827 A | 9/1998 | Haines et al. |
| 5,810,831 A | 9/1998 | D'Antonio |
| 5,817,097 A | 10/1998 | Howard et al. |
| 5,817,109 A | 10/1998 | Mcgarry et al. |
| 5,824,083 A | 10/1998 | Draenert |
| 5,835,619 A | 11/1998 | Morimoto et al. |
| 5,842,477 A | 12/1998 | Naughton et al. |
| 5,846,931 A | 12/1998 | Hattersley et al. |
| 5,860,980 A | 1/1999 | Axelson, Jr. et al. |
| 5,860,981 A | 1/1999 | Bertin et al. |
| 5,866,415 A | 2/1999 | Villeneuve |
| 5,871,018 A | 2/1999 | Delp et al. |
| 5,871,493 A | 2/1999 | Sjostrom et al. |
| 5,876,456 A | 3/1999 | Sederholm et al. |
| 5,879,354 A | 3/1999 | Haines et al. |
| 5,879,398 A | 3/1999 | Swarts et al. |
| 5,879,402 A | 3/1999 | Lawes et al. |
| 5,879,404 A | 3/1999 | Bateman et al. |
| 5,880,976 A | 3/1999 | DiGioia, III et al. |
| 5,885,297 A | 3/1999 | Matsen |
| 5,885,298 A | 3/1999 | Herrington et al. |
| 5,888,219 A | 3/1999 | Bonutti |
| 5,895,389 A | 4/1999 | Schenk et al. |
| 5,899,907 A | 5/1999 | Johnson |
| 5,899,914 A | 5/1999 | Zirps et al. |
| 5,901,060 A | 5/1999 | Schall et al. |
| 5,902,340 A | 5/1999 | White et al. |
| 5,908,424 A | 6/1999 | Bertin et al. |
| 5,911,723 A | 6/1999 | Ashby et al. |
| 5,911,724 A | 6/1999 | Wehrli |
| 5,913,874 A | 6/1999 | Berns et al. |
| 5,916,219 A | 6/1999 | Matsuno et al. |
| 5,921,988 A | 7/1999 | Legrand |
| 5,921,990 A | 7/1999 | Webb |
| 5,925,049 A | 7/1999 | Gustilo et al. |
| 5,925,077 A | 7/1999 | Williamson et al. |

(56) References Cited

U.S. PATENT DOCUMENTS

| | | |
|---|---|---|
| 5,942,370 A | 8/1999 | Neckers |
| 5,961,499 A | 10/1999 | Bonutti et al. |
| 5,967,777 A | 10/1999 | Klein et al. |
| 5,976,149 A | 11/1999 | Masini |
| 5,980,526 A | 11/1999 | Johnson et al. |
| 5,995,738 A | 11/1999 | DiGioia, III et al. |
| 5,997,566 A | 12/1999 | Tobin |
| 6,002,859 A | 12/1999 | DiGioia, III et al. |
| 6,007,537 A | 12/1999 | Burkinshaw et al. |
| 6,008,433 A | 12/1999 | Stone |
| 6,012,456 A | 1/2000 | Schuerch |
| 6,013,081 A | 1/2000 | Burkinshaw et al. |
| 6,015,419 A | 1/2000 | Strome et al. |
| 6,019,767 A | 2/2000 | Howell |
| 6,022,350 A | 2/2000 | Ganem |
| 6,022,356 A * | 2/2000 | Noyes ............... A61B 17/1714 606/88 |
| 6,024,746 A | 2/2000 | Katz |
| 6,033,415 A | 3/2000 | Mittelstadt et al. |
| 6,042,612 A | 3/2000 | Voydeville |
| 6,056,754 A | 5/2000 | Haines et al. |
| 6,056,756 A | 5/2000 | Eng et al. |
| 6,059,789 A | 5/2000 | Dinger |
| 6,059,817 A | 5/2000 | Bonutti et al. |
| 6,059,831 A | 5/2000 | Braslow et al. |
| 6,059,833 A | 5/2000 | Doets |
| 6,063,095 A | 5/2000 | Wang et al. |
| 6,066,175 A | 5/2000 | Henderson et al. |
| 6,077,270 A | 6/2000 | Katz |
| 6,077,287 A | 6/2000 | Taylor et al. |
| 6,086,593 A | 7/2000 | Bonutti |
| 6,090,122 A | 7/2000 | Sjostrom et al. |
| 6,096,043 A | 8/2000 | Techiera et al. |
| 6,099,531 A | 8/2000 | Bonutti |
| 6,099,532 A | 8/2000 | Florea |
| 6,102,850 A | 8/2000 | Wang et al. |
| 6,106,529 A | 8/2000 | Techiera |
| 6,118,845 A | 9/2000 | Simon et al. |
| 6,120,509 A | 9/2000 | Wheeler |
| 6,120,510 A | 9/2000 | Albrektsson et al. |
| 6,120,544 A | 9/2000 | Grundei et al. |
| 6,126,690 A | 10/2000 | Ateshian et al. |
| 6,126,692 A | 10/2000 | Robie et al. |
| 6,132,469 A | 10/2000 | Schroeder |
| 6,132,472 A | 10/2000 | Bonutti |
| 6,136,033 A | 10/2000 | Suemer |
| 6,156,069 A | 12/2000 | Amstutz |
| 6,156,070 A | 12/2000 | Incavo et al. |
| 6,159,217 A | 12/2000 | Robie et al. |
| 6,159,246 A | 12/2000 | Mendes et al. |
| 6,161,080 A | 12/2000 | Aouni-Ateshian et al. |
| 6,162,257 A | 12/2000 | Gustilo et al. |
| 6,165,223 A | 12/2000 | Metzger et al. |
| 6,171,340 B1 | 1/2001 | Mcdowell et al. |
| 6,174,321 B1 | 1/2001 | Webb |
| 6,185,315 B1 | 2/2001 | Schmucker et al. |
| 6,187,010 B1 | 2/2001 | Masini |
| 6,187,023 B1 | 2/2001 | Bonutti |
| 6,195,158 B1 | 2/2001 | Cadell et al. |
| 6,195,615 B1 | 2/2001 | Lysen |
| 6,197,064 B1 | 3/2001 | Haines et al. |
| 6,198,794 B1 | 3/2001 | Peshkin et al. |
| 6,203,546 B1 | 3/2001 | Macmahon |
| 6,205,411 B1 | 3/2001 | Digioia, III et al. |
| 6,206,927 B1 | 3/2001 | Fell et al. |
| 6,210,445 B1 | 4/2001 | Zawadzki |
| 6,211,976 B1 | 4/2001 | Popovich et al. |
| 6,214,051 B1 | 4/2001 | Badorf et al. |
| 6,228,121 B1 | 5/2001 | Khalili |
| 6,238,435 B1 | 5/2001 | Meulink et al. |
| 6,254,604 B1 | 7/2001 | Howell |
| 6,258,097 B1 | 7/2001 | Cook et al. |
| 6,258,127 B1 | 7/2001 | Schmotzer |
| 6,264,698 B1 | 7/2001 | Lawes et al. |
| 6,270,529 B1 | 8/2001 | Terrill-Grisoni et al. |
| 6,273,891 B1 | 8/2001 | Masini |
| 6,277,136 B1 | 8/2001 | Bonutti et al. |
| 6,290,703 B1 | 9/2001 | Ganem |
| 6,290,704 B1 | 9/2001 | Burkinshaw et al. |
| 6,290,727 B1 | 9/2001 | Otto et al. |
| 6,293,971 B1 | 9/2001 | Nelson et al. |
| 6,301,495 B1 | 10/2001 | Gueziec et al. |
| 6,302,913 B1 | 10/2001 | Ripamonti et al. |
| 6,310,269 B1 | 10/2001 | Friese et al. |
| 6,312,258 B1 | 11/2001 | Ashman |
| 6,312,473 B1 | 11/2001 | Oshida |
| 6,319,285 B1 | 11/2001 | Chamier et al. |
| 6,322,728 B1 | 11/2001 | Brodkin et al. |
| 6,325,806 B1 | 12/2001 | Fox |
| 6,325,829 B1 | 12/2001 | Schmotzer |
| 6,327,491 B1 | 12/2001 | Franklin et al. |
| 6,328,572 B1 | 12/2001 | Higashida et al. |
| 6,338,737 B1 | 1/2002 | Toledano |
| 6,338,738 B1 | 1/2002 | Bellotti et al. |
| 6,343,987 B2 | 2/2002 | Hayama et al. |
| 6,354,011 B1 | 3/2002 | Albrecht |
| 6,358,266 B1 | 3/2002 | Bonutti |
| 6,361,506 B1 | 3/2002 | Saenger et al. |
| 6,361,563 B2 | 3/2002 | Terrill-Grisoni et al. |
| 6,361,565 B1 | 3/2002 | Bonutti |
| 6,379,299 B1 | 4/2002 | Borodulin et al. |
| 6,379,388 B1 | 4/2002 | Ensign et al. |
| 6,383,228 B1 | 5/2002 | Schmotzer |
| 6,391,040 B1 | 5/2002 | Christoudias |
| 6,391,251 B1 | 5/2002 | Keicher et al. |
| 6,395,005 B1 | 5/2002 | Lovell |
| 6,406,495 B1 | 6/2002 | Schoch |
| 6,409,722 B1 | 6/2002 | Hoey et al. |
| 6,413,279 B1 | 7/2002 | Metzger et al. |
| 6,416,553 B1 | 7/2002 | White et al. |
| 6,423,063 B1 | 7/2002 | Bonutti |
| 6,423,068 B1 | 7/2002 | Reisberg et al. |
| 6,424,332 B1 | 7/2002 | Powell |
| 6,427,698 B1 | 8/2002 | Yoon et al. |
| 6,428,541 B1 | 8/2002 | Boyd et al. |
| 6,431,743 B1 | 8/2002 | Mizutani et al. |
| D462,767 S | 9/2002 | Meyer et al. |
| 6,447,448 B1 | 9/2002 | Ishikawa et al. |
| 6,458,135 B1 | 10/2002 | Harwin et al. |
| 6,459,948 B1 | 10/2002 | Ateshian et al. |
| 6,463,351 B1 | 10/2002 | Clynch |
| 6,468,280 B1 | 10/2002 | Saenger et al. |
| 6,468,289 B1 | 10/2002 | Bonutti |
| 6,475,243 B1 | 11/2002 | Sheldon et al. |
| 6,478,799 B1 | 11/2002 | Williamson |
| 6,482,209 B1 | 11/2002 | Engh et al. |
| 6,482,236 B2 | 11/2002 | Habecker |
| 6,488,715 B1 | 12/2002 | Pope et al. |
| 6,500,181 B1 | 12/2002 | Portney |
| 6,503,255 B1 | 1/2003 | Albrektsson et al. |
| 6,503,267 B2 | 1/2003 | Bonutti et al. |
| 6,508,980 B1 | 1/2003 | Sachs et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,519,998 B2 | 2/2003 | Ertl et al. |
| 6,520,964 B2 | 2/2003 | Tallarida et al. |
| 6,533,737 B1 | 3/2003 | Brosseau et al. |
| 6,547,823 B2 | 4/2003 | Scarborough et al. |
| 6,551,325 B2 | 4/2003 | Neubauer et al. |
| 6,554,837 B1 | 4/2003 | Hauri et al. |
| 6,554,838 B2 | 4/2003 | Mcgovern et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,562,073 B2 | 5/2003 | Foley |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,583,630 B2 | 6/2003 | Mendes et al. |
| 6,589,283 B1 | 7/2003 | Metzger et al. |
| 6,591,581 B2 | 7/2003 | Schmieding |
| 6,602,259 B1 | 8/2003 | Masini |

(56) References Cited

U.S. PATENT DOCUMENTS

| | | |
|---|---|---|
| 6,605,293 B1 | 8/2003 | Giordano et al. |
| 6,610,067 B2 | 8/2003 | Tallarida et al. |
| 6,610,096 B2 | 8/2003 | MacDonald |
| 6,620,181 B1 | 9/2003 | Bonutti |
| 6,622,567 B1 | 9/2003 | Hamel et al. |
| 6,629,999 B1 | 10/2003 | Serafin, Jr. |
| 6,632,225 B2 | 10/2003 | Sanford et al. |
| 6,635,073 B2 | 10/2003 | Bonutti |
| 6,641,617 B1 | 11/2003 | Merrill et al. |
| 6,673,077 B1 | 1/2004 | Katz |
| 6,676,662 B1 | 1/2004 | Bagga et al. |
| 6,676,892 B2 | 1/2004 | Das et al. |
| 6,682,566 B2 | 1/2004 | Draenert et al. |
| 6,682,567 B1 | 1/2004 | Schroeder |
| 6,695,848 B2 | 2/2004 | Haines |
| 6,696,073 B2 | 2/2004 | Boyce et al. |
| 6,697,664 B2 | 2/2004 | Kienzle, III et al. |
| 6,699,289 B2 | 3/2004 | Iannotti et al. |
| 6,701,174 B1 | 3/2004 | Krause et al. |
| 6,702,821 B2 | 3/2004 | Bonutti |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,743,235 B2 | 6/2004 | Subba Rao |
| 6,746,487 B2 | 6/2004 | Scifert et al. |
| 6,749,638 B1 | 6/2004 | Saladino |
| 6,750,653 B1 | 6/2004 | Zou et al. |
| 6,770,078 B2 | 8/2004 | Bonutti |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,810,753 B2 | 11/2004 | Valdevit et al. |
| 6,821,299 B2 | 11/2004 | Kirking et al. |
| 6,823,871 B2 | 11/2004 | Schmieding |
| 6,827,723 B2 | 12/2004 | Carson |
| 6,871,549 B2 | 3/2005 | Serra et al. |
| 6,887,247 B1 | 5/2005 | Couture et al. |
| 6,905,514 B2 | 6/2005 | Carignan et al. |
| 6,916,324 B2 | 7/2005 | Sanford |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,966,932 B1 | 11/2005 | Schroeder |
| 6,975,755 B1 | 12/2005 | Baumberg |
| 6,979,299 B2 | 12/2005 | Peabody et al. |
| 6,990,220 B2 | 1/2006 | Ellis et al. |
| 6,993,406 B1 | 1/2006 | Cesarano, III et al. |
| 7,001,385 B2 | 2/2006 | Bonutti |
| 7,001,393 B2 | 2/2006 | Schwenke et al. |
| 7,022,141 B2 | 4/2006 | Dwyer et al. |
| 7,029,477 B2 | 4/2006 | Grimm |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | Mckinnon |
| RE39,301 E | 9/2006 | Bertin |
| 7,104,995 B2 | 9/2006 | Crofford |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |
| D533,664 S | 12/2006 | Büttler et al. |
| 7,169,185 B2 | 1/2007 | Sidebotham |
| 7,172,599 B2 | 2/2007 | Steffensmeier et al. |
| 7,174,282 B2 | 2/2007 | Hollister et al. |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | Disilvestro et al. |
| 7,220,264 B1 | 5/2007 | Hershberger |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,261,719 B1 | 8/2007 | Twomey et al. |
| 7,275,218 B2 | 9/2007 | Petrella et al. |
| 7,282,054 B2 | 10/2007 | Steffensmeier et al. |
| 7,291,117 B2 | 11/2007 | Boecker et al. |
| 7,291,177 B2 | 11/2007 | Gibbs |
| 7,294,133 B2 | 11/2007 | Zink et al. |
| 7,297,164 B2 | 11/2007 | Johnson et al. |
| 7,309,339 B2 | 12/2007 | Cusick et al. |
| 7,331,965 B2 | 2/2008 | Nielsen |
| 7,333,013 B2 | 2/2008 | Berger |
| 7,335,207 B1 | 2/2008 | Smith |
| 7,335,231 B2 | 2/2008 | Mclean |
| 7,338,499 B1 | 3/2008 | Kuczynski et al. |
| 7,371,260 B2 | 5/2008 | Malinin |
| 7,377,182 B2 | 5/2008 | Serra et al. |
| 7,383,164 B2 | 6/2008 | Aram et al. |
| 7,385,498 B2 | 6/2008 | Dobosz |
| 7,388,972 B2 | 6/2008 | Kitson |
| 7,390,327 B2 | 6/2008 | Collazo et al. |
| 7,392,076 B2 | 6/2008 | Moctezuma De |
| 7,419,492 B2 | 9/2008 | Yoon et al. |
| 7,427,200 B2 | 9/2008 | Noble et al. |
| 7,427,272 B2 | 9/2008 | Richard et al. |
| 7,458,989 B2 | 12/2008 | Banks |
| 7,465,320 B1 | 12/2008 | Kito et al. |
| 7,468,075 B2 | 12/2008 | Lang et al. |
| 7,474,223 B2 | 1/2009 | Nycz et al. |
| 7,488,324 B1 | 2/2009 | Metzger et al. |
| 7,488,325 B2 | 2/2009 | Qian et al. |
| 7,494,510 B2 | 2/2009 | Zweymuller |
| 7,517,365 B2 | 4/2009 | Carignan et al. |
| 7,519,540 B2 | 4/2009 | Mayaud |
| 7,527,631 B2 | 5/2009 | Maroney et al. |
| 7,534,263 B2 | 5/2009 | Burdulis, Jr. et al. |
| 7,537,664 B2 | 5/2009 | O'neill et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kleman |
| 7,601,155 B2 | 10/2009 | Petersen |
| 7,603,192 B2 | 10/2009 | Martin et al. |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,636,595 B2 | 12/2009 | Marquart |
| 7,646,161 B2 | 1/2010 | Albu-schäffer et al. |
| 7,651,501 B2 | 1/2010 | Penenberg et al. |
| 7,660,623 B2 | 2/2010 | Hunter et al. |
| 7,670,345 B2 | 3/2010 | Plassky et al. |
| 7,674,100 B2 | 3/2010 | Hayes-pankhurst et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,702,380 B1 | 4/2010 | Dean |
| 7,704,253 B2 | 4/2010 | Bastian et al. |
| 7,723,395 B2 | 5/2010 | Ringeisen et al. |
| 7,747,305 B2 | 6/2010 | Dean et al. |
| D622,854 S | 8/2010 | Otto et al. |
| 7,780,672 B2 | 8/2010 | Metzger et al. |
| 7,780,681 B2 | 8/2010 | Sarin et al. |
| 7,780,740 B2 | 8/2010 | Steinberg |

(56) References Cited

U.S. PATENT DOCUMENTS

| | | |
|---|---|---|
| 7,789,885 B2 | 9/2010 | Metzger |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,833,245 B2 | 11/2010 | Kaes et al. |
| 7,837,040 B2 | 11/2010 | Ward et al. |
| 7,837,690 B2 | 11/2010 | Metzger |
| 7,846,382 B2 | 12/2010 | Strand |
| 7,850,698 B2 | 12/2010 | Straszheim-Morley et al. |
| 7,854,737 B2 | 12/2010 | Daniels et al. |
| 7,879,109 B2 | 2/2011 | Borden et al. |
| 7,892,261 B2 | 2/2011 | Bonutti |
| 7,896,921 B2 | 3/2011 | Smith et al. |
| 7,926,363 B2 | 4/2011 | Miller et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,988,736 B2 | 8/2011 | May et al. |
| 7,993,353 B2 | 8/2011 | Roßner et al. |
| 8,057,482 B2 | 11/2011 | Stone et al. |
| 8,062,301 B2 | 11/2011 | Ammann et al. |
| 8,066,708 B2 | 11/2011 | Lang et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,105,330 B2 | 1/2012 | Fitz et al. |
| 8,109,942 B2 | 2/2012 | Carson |
| 8,122,582 B2 | 2/2012 | Burdulis, Jr. et al. |
| 8,133,230 B2 | 3/2012 | Stevens et al. |
| 8,133,234 B2 | 3/2012 | Meridew et al. |
| 8,137,406 B2 | 3/2012 | Novak et al. |
| 8,147,861 B2 | 4/2012 | Jones et al. |
| 8,160,345 B2 | 4/2012 | Pavlovskaia et al. |
| 8,167,823 B2 | 5/2012 | Nycz et al. |
| 8,167,951 B2 | 5/2012 | Ammann et al. |
| 8,170,641 B2 | 5/2012 | Belcher |
| 8,172,850 B2 | 5/2012 | Mcminn |
| 8,182,489 B2 | 5/2012 | Horacek |
| 8,192,441 B2 | 6/2012 | Collazo |
| 8,192,495 B2 | 6/2012 | Simpson et al. |
| 8,200,355 B2 | 6/2012 | Lee et al. |
| 8,211,112 B2 | 7/2012 | Novak et al. |
| 8,221,430 B2 | 7/2012 | Park et al. |
| 8,241,292 B2 | 8/2012 | Collazo |
| 8,241,293 B2 | 8/2012 | Stone et al. |
| 8,246,680 B2 | 8/2012 | Betz et al. |
| 8,260,589 B1 | 9/2012 | Kumar |
| 8,265,790 B2 | 9/2012 | Amiot et al. |
| 8,268,099 B2 | 9/2012 | O'neill et al. |
| 8,268,100 B2 | 9/2012 | O'neill et al. |
| D669,176 S | 10/2012 | Frey |
| 8,282,646 B2 | 10/2012 | Schoenfeld et al. |
| 8,298,237 B2 | 10/2012 | Schoenfeld et al. |
| 8,303,596 B2 | 11/2012 | Plaßky et al. |
| 8,313,491 B2 | 11/2012 | Green, II et al. |
| D672,038 S | 12/2012 | Frey |
| 8,333,772 B2 | 12/2012 | Fox et al. |
| 8,337,426 B2 | 12/2012 | Nycz |
| 8,337,501 B2 | 12/2012 | Fitz et al. |
| 8,337,503 B2 | 12/2012 | Lian |
| 8,355,773 B2 | 1/2013 | Leitner et al. |
| 8,372,078 B2 | 2/2013 | Collazo |
| 8,377,066 B2 | 2/2013 | Katrana et al. |
| 8,388,690 B2 | 3/2013 | Singhatat et al. |
| 8,398,646 B2 | 3/2013 | Metzger et al. |
| 8,407,067 B2 | 3/2013 | Uthgenannt et al. |
| 8,414,594 B2 | 4/2013 | Berger et al. |
| 8,419,741 B2 | 4/2013 | Carignan et al. |
| 8,425,522 B2 | 4/2013 | Bonutti |
| 8,430,882 B2 | 4/2013 | Lowry et al. |
| 8,430,931 B2 | 4/2013 | Acker et al. |
| 8,439,675 B2 | 5/2013 | De Moyer |
| 8,439,925 B2 | 5/2013 | Marino et al. |
| 8,444,564 B2 | 5/2013 | Mahfouz et al. |
| 8,444,651 B2 | 5/2013 | Kunz et al. |
| 8,457,930 B2 | 6/2013 | Schroeder |
| 8,460,302 B2 | 6/2013 | Park et al. |
| 8,469,961 B2 | 6/2013 | Alleyne et al. |
| 8,473,305 B2 | 6/2013 | Belcher et al. |
| 8,486,150 B2 | 7/2013 | White et al. |
| 8,500,740 B2 | 8/2013 | Bojarski et al. |
| 8,529,578 B2 | 9/2013 | Daniels et al. |
| 8,532,361 B2 | 9/2013 | Pavlovskaia et al. |
| 8,532,806 B1 | 9/2013 | Masson |
| 8,532,807 B2 | 9/2013 | Metzger |
| 8,535,387 B2 | 9/2013 | Meridew et al. |
| 8,543,234 B2 | 9/2013 | Gao |
| 8,545,508 B2 | 10/2013 | Collazo |
| 8,551,099 B2 | 10/2013 | Lang et al. |
| 8,568,487 B2 | 10/2013 | Witt et al. |
| 8,591,516 B2 | 11/2013 | Metzger et al. |
| 8,597,365 B2 | 12/2013 | Meridew |
| 8,603,180 B2 | 12/2013 | White et al. |
| 8,608,748 B2 | 12/2013 | Metzger et al. |
| 8,608,749 B2 | 12/2013 | Meridew et al. |
| 8,617,170 B2 | 12/2013 | Ashby et al. |
| 8,617,174 B2 | 12/2013 | Axelson, Jr. et al. |
| 8,617,175 B2 | 12/2013 | Park et al. |
| 8,632,547 B2 | 1/2014 | Maxson et al. |
| 8,652,142 B2 | 2/2014 | Geissler |
| 8,668,700 B2 | 3/2014 | Catanzarite et al. |
| 8,702,712 B2 | 4/2014 | Jordan et al. |
| 8,702,715 B2 | 4/2014 | Ammann et al. |
| 8,706,285 B2 | 4/2014 | Narainasamy et al. |
| 8,715,289 B2 | 5/2014 | Smith |
| 8,728,387 B2 | 5/2014 | Jones et al. |
| 8,735,773 B2 | 5/2014 | Lang |
| 8,764,760 B2 | 7/2014 | Metzger et al. |
| 8,775,133 B2 | 7/2014 | Schroeder |
| 8,777,875 B2 | 7/2014 | Park |
| 8,781,557 B2 | 7/2014 | Dean et al. |
| 8,828,016 B2 | 9/2014 | Major et al. |
| 8,828,087 B2 | 9/2014 | Stone et al. |
| 8,828,089 B1 | 9/2014 | Perez et al. |
| 8,834,568 B2 | 9/2014 | Shapiro |
| 8,858,561 B2 | 10/2014 | White et al. |
| 8,864,769 B2 | 10/2014 | Stone et al. |
| 8,900,244 B2 | 12/2014 | Meridew et al. |
| 8,903,530 B2 | 12/2014 | Metzger |
| 8,956,364 B2 | 2/2015 | Catanzarite |
| 8,979,936 B2 | 3/2015 | White et al. |
| 8,986,309 B1 | 3/2015 | Murphy |
| 9,005,297 B2 | 4/2015 | Katrana et al. |
| 9,060,788 B2 | 6/2015 | Bollinger |
| 9,066,734 B2 | 6/2015 | Schoenefeld et al. |
| 9,107,139 B2 | 8/2015 | Sirotkin et al. |
| 9,113,971 B2 | 8/2015 | Metzger et al. |
| 9,173,661 B2 | 11/2015 | Metzger et al. |
| 9,186,254 B2 | 11/2015 | Fitz et al. |
| 9,208,558 B2 | 12/2015 | Dean et al. |
| 9,241,745 B2 | 1/2016 | Smith et al. |
| 9,271,744 B2 | 3/2016 | Meridew |
| 9,275,191 B2 | 3/2016 | Dean et al. |
| 9,289,253 B2 | 3/2016 | Vanasse et al. |
| 9,292,920 B2 | 3/2016 | Dean et al. |
| 9,330,206 B2 | 5/2016 | Dean et al. |
| 9,339,278 B2 | 5/2016 | Meridew et al. |
| 9,345,548 B2 | 5/2016 | Schoenefeld et al. |
| 9,445,907 B2 | 9/2016 | Meridew et al. |
| 9,468,538 B2 | 10/2016 | Nycz et al. |

(56) References Cited

U.S. PATENT DOCUMENTS

| | | |
|---|---|---|
| 9,480,490 B2 | 11/2016 | Metzger et al. |
| 9,480,580 B2 | 11/2016 | White et al. |
| 9,522,010 B2 | 12/2016 | Metzger et al. |
| 9,539,013 B2 | 1/2017 | Katrana et al. |
| 9,662,127 B2 | 5/2017 | Meridew et al. |
| 9,662,216 B2 | 5/2017 | Witt et al. |
| 9,700,329 B2 | 7/2017 | Metzger et al. |
| 9,730,616 B2 | 8/2017 | Hershberger |
| 9,743,935 B2 | 8/2017 | Smith et al. |
| 9,795,399 B2 | 10/2017 | Metzger et al. |
| 9,861,387 B2 | 1/2018 | Metzger et al. |
| 9,907,659 B2 | 3/2018 | Belcher et al. |
| 9,913,734 B2 | 3/2018 | White et al. |
| 9,918,740 B2 | 3/2018 | Uthgenannt et al. |
| 9,968,376 B2 | 5/2018 | Metzger et al. |
| 9,993,344 B2 | 6/2018 | White et al. |
| 2001/0005797 A1 | 6/2001 | Barlow et al. |
| 2001/0011190 A1 | 8/2001 | Park |
| 2001/0018589 A1 | 8/2001 | Muller |
| 2001/0021876 A1 | 9/2001 | Terril-Grisoni et al. |
| 2001/0034554 A1 | 10/2001 | Pappas |
| 2001/0037155 A1 | 11/2001 | Merchant |
| 2001/0054478 A1 | 12/2001 | Watanabe et al. |
| 2002/0007294 A1 | 1/2002 | Bradbury et al. |
| 2002/0029038 A1 | 3/2002 | Haines |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0062127 A1 | 5/2002 | Schumacher et al. |
| 2002/0077540 A1 | 6/2002 | Kienzle, III |
| 2002/0082741 A1 | 6/2002 | Mazumder et al. |
| 2002/0087274 A1 | 7/2002 | Alexander et al. |
| 2002/0092532 A1 | 7/2002 | Yoon |
| 2002/0107522 A1 | 8/2002 | Picard et al. |
| 2002/0107523 A1 | 8/2002 | Naughton et al. |
| 2002/0116023 A1 | 8/2002 | Fletcher et al. |
| 2002/0120342 A1 | 8/2002 | Gibbs |
| 2002/0128872 A1 | 9/2002 | Giammattei |
| 2002/0147415 A1 | 10/2002 | Martelli |
| 2002/0173797 A1 | 11/2002 | Van Zile et al. |
| 2002/0186818 A1 | 12/2002 | Arnaud et al. |
| 2002/0193797 A1 | 12/2002 | Johnson et al. |
| 2002/0198528 A1 | 12/2002 | Engh et al. |
| 2002/0198529 A1 | 12/2002 | Masini |
| 2002/0198531 A1 | 12/2002 | Millard et al. |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Stuart, Jr. et al. |
| 2003/0028196 A1 | 2/2003 | Bonutti |
| 2003/0039676 A1 | 2/2003 | Boyce et al. |
| 2003/0055502 A1 | 3/2003 | Lang et al. |
| 2003/0060831 A1 | 3/2003 | Bonutti |
| 2003/0069897 A1 | 4/2003 | Roy et al. |
| 2003/0074800 A1 | 4/2003 | Huang |
| 2003/0100906 A1 | 5/2003 | Rosa et al. |
| 2003/0100907 A1 | 5/2003 | Rosa et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0130665 A1 | 7/2003 | Pinczewski et al. |
| 2003/0130741 A1 | 7/2003 | McMinn |
| 2003/0139817 A1 | 7/2003 | Tuke et al. |
| 2003/0153829 A1 | 8/2003 | Sarin et al. |
| 2003/0158606 A1 | 8/2003 | Coon et al. |
| 2003/0171757 A1 | 9/2003 | Coon et al. |
| 2003/0181987 A1 | 9/2003 | Muirhead-allwood |
| 2003/0212403 A1 | 11/2003 | Swanson |
| 2003/0212459 A1 | 11/2003 | Gibbs |
| 2003/0216669 A1 | 11/2003 | Lang et al. |
| 2003/0216741 A1 | 11/2003 | Sanford et al. |
| 2003/0220641 A1 | 11/2003 | Thelen et al. |
| 2003/0225413 A1 | 12/2003 | Sanford et al. |
| 2004/0018144 A1 | 1/2004 | Briscoe |
| 2004/0030245 A1 | 2/2004 | Noble et al. |
| 2004/0034302 A1 | 2/2004 | Abovitz et al. |
| 2004/0039395 A1 | 2/2004 | Coon et al. |
| 2004/0044295 A1 | 3/2004 | Reinert et al. |
| 2004/0054372 A1 | 3/2004 | Corden et al. |
| 2004/0054416 A1 | 3/2004 | Wyss et al. |
| 2004/0068187 A1 | 4/2004 | Krause et al. |
| 2004/0092932 A1 | 5/2004 | Aubin et al. |
| 2004/0097952 A1 | 5/2004 | Sarin et al. |
| 2004/0098133 A1 | 5/2004 | Carignan et al. |
| 2004/0102785 A1 | 5/2004 | Hodorek et al. |
| 2004/0102792 A1 | 5/2004 | Sarin et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0117026 A1 | 6/2004 | Tuma et al. |
| 2004/0122436 A1 | 6/2004 | Grimm |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138670 A1 | 7/2004 | Metzger |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0193169 A1 | 9/2004 | Schon et al. |
| 2004/0204644 A1 | 10/2004 | Tsougarakis et al. |
| 2004/0204760 A1 | 10/2004 | Fitz et al. |
| 2004/0212586 A1 | 10/2004 | Trueman, III |
| 2004/0220583 A1 | 11/2004 | Pieczynski, II et al. |
| 2004/0225369 A1 | 11/2004 | Lakin et al. |
| 2004/0230199 A1 | 11/2004 | Jansen et al. |
| 2004/0236341 A1 | 11/2004 | Petersen |
| 2004/0236424 A1 | 11/2004 | Berez et al. |
| 2004/0243148 A1 | 12/2004 | Wasielewski |
| 2004/0243481 A1 | 12/2004 | Bradbury et al. |
| 2004/0249386 A1 | 12/2004 | Faoro |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0009952 A1 | 1/2005 | Qian et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0015599 A1 | 1/2005 | Wang et al. |
| 2005/0015603 A1 | 1/2005 | Cabezas et al. |
| 2005/0015604 A1 | 1/2005 | Sundararajan et al. |
| 2005/0015605 A1 | 1/2005 | Lin et al. |
| 2005/0019664 A1 | 1/2005 | Matsumoto |
| 2005/0021044 A1 | 1/2005 | Stone et al. |
| 2005/0021148 A1 | 1/2005 | Gibbs |
| 2005/0021299 A1 | 1/2005 | Kadota et al. |
| 2005/0021494 A1 | 1/2005 | Wilkinson |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065617 A1 | 3/2005 | Moctezuma De et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | De La |
| 2005/0109855 A1 | 5/2005 | Mccombs |
| 2005/0113659 A1 | 5/2005 | Pothier et al. |
| 2005/0113840 A1 | 5/2005 | Metzger et al. |
| 2005/0113841 A1 | 5/2005 | Sheldon et al. |

(56) References Cited

U.S. PATENT DOCUMENTS

| | | |
|---|---|---|
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0143828 A1 | 6/2005 | Collins et al. |
| 2005/0148843 A1 | 7/2005 | Roose |
| 2005/0149042 A1 | 7/2005 | Metzger |
| 2005/0171545 A1 | 8/2005 | Walsh et al. |
| 2005/0177170 A1 | 8/2005 | Fisher et al. |
| 2005/0177245 A1 | 8/2005 | Leatherbury et al. |
| 2005/0203384 A1 | 9/2005 | Sati et al. |
| 2005/0203536 A1 | 9/2005 | Laffargue et al. |
| 2005/0203540 A1 | 9/2005 | Broyles |
| 2005/0209597 A1 | 9/2005 | Long et al. |
| 2005/0209605 A1 | 9/2005 | Grimm et al. |
| 2005/0216305 A1 | 9/2005 | Funderud |
| 2005/0222571 A1 | 10/2005 | Ryan |
| 2005/0222573 A1 | 10/2005 | Branch et al. |
| 2005/0228393 A1 | 10/2005 | Williams, III et al. |
| 2005/0234332 A1 | 10/2005 | Murphy |
| 2005/0234461 A1 | 10/2005 | Burdulis, Jr. et al. |
| 2005/0234465 A1 | 10/2005 | Mccombs et al. |
| 2005/0234468 A1 | 10/2005 | Carson |
| 2005/0240195 A1 | 10/2005 | Axelson, Jr. et al. |
| 2005/0240267 A1 | 10/2005 | Randall et al. |
| 2005/0244239 A1 | 11/2005 | Shimp |
| 2005/0245808 A1 | 11/2005 | Carson |
| 2005/0245934 A1 | 11/2005 | Tuke et al. |
| 2005/0245936 A1 | 11/2005 | Tuke et al. |
| 2005/0251026 A1 | 11/2005 | Stone |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis, Jr. et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0025778 A1 | 2/2006 | Ferree |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058809 A1 | 3/2006 | Zink et al. |
| 2006/0058884 A1 | 3/2006 | Aram et al. |
| 2006/0058886 A1 | 3/2006 | Wozencroft |
| 2006/0069444 A1 | 3/2006 | Deffenbaugh |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0094958 A1 | 5/2006 | Marquart et al. |
| 2006/0095044 A1 | 5/2006 | Grady, Jr. et al. |
| 2006/0095047 A1 | 5/2006 | De La |
| 2006/0095049 A1 | 5/2006 | Zannis et al. |
| 2006/0100832 A1 | 5/2006 | Bowman |
| 2006/0105011 A1 | 5/2006 | Sun et al. |
| 2006/0111722 A1 | 5/2006 | Bouadi |
| 2006/0122491 A1 | 6/2006 | Murray et al. |
| 2006/0122616 A1 | 6/2006 | Bennett et al. |
| 2006/0122618 A1 | 6/2006 | Claypool et al. |
| 2006/0136058 A1 | 6/2006 | Pietrzak |
| 2006/0142657 A1 | 6/2006 | Quaid et al. |
| 2006/0142774 A1 | 6/2006 | Metzger |
| 2006/0142778 A1 | 6/2006 | Dees |
| 2006/0147332 A1 | 7/2006 | Jones et al. |
| 2006/0149283 A1 | 7/2006 | May et al. |
| 2006/0155380 A1 | 7/2006 | Clemow et al. |
| 2006/0161165 A1 | 7/2006 | Swanson et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0192319 A1 | 8/2006 | Solar |
| 2006/0195111 A1 | 8/2006 | Couture |
| 2006/0195194 A1 | 8/2006 | Gunther |
| 2006/0195198 A1 | 8/2006 | James |
| 2006/0198943 A1 | 9/2006 | Kumar |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0241775 A1 | 10/2006 | Buss |
| 2006/0241776 A1 | 10/2006 | Brown et al. |
| 2006/0241781 A1 | 10/2006 | Brown et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0287891 A1 | 12/2006 | Grasso et al. |
| 2006/0293681 A1 | 12/2006 | Claypool et al. |
| 2007/0015995 A1 | 1/2007 | Lang et al. |
| 2007/0016008 A1 | 1/2007 | Schoenefeld |
| 2007/0016209 A1 | 1/2007 | Ammann et al. |
| 2007/0027680 A1 | 2/2007 | Ashley et al. |
| 2007/0039205 A1 | 2/2007 | Erb et al. |
| 2007/0043582 A1 | 2/2007 | Peveto et al. |
| 2007/0066917 A1 | 3/2007 | Hodorek et al. |
| 2007/0073133 A1 | 3/2007 | Schoenefeld |
| 2007/0073136 A1 | 3/2007 | Metzger |
| 2007/0073137 A1 | 3/2007 | Schoenefeld |
| 2007/0083209 A1 | 4/2007 | Schenberger et al. |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0106299 A1 | 5/2007 | Manspeizer |
| 2007/0106391 A1 | 5/2007 | Ronk |
| 2007/0118055 A1 | 5/2007 | Mccombs |
| 2007/0118138 A1 | 5/2007 | Seo et al. |
| 2007/0118243 A1 | 5/2007 | Schroeder et al. |
| 2007/0129809 A1 | 6/2007 | Meridew et al. |
| 2007/0142914 A1 | 6/2007 | Jones et al. |
| 2007/0149981 A1 | 6/2007 | Bhattacharyya |
| 2007/0150068 A1 | 6/2007 | Dong et al. |
| 2007/0156066 A1 | 7/2007 | Mcginley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0179739 A1 | 8/2007 | Donofrio et al. |
| 2007/0185498 A2 | 8/2007 | Lavallee |
| 2007/0191962 A1 | 8/2007 | Jones |
| 2007/0198022 A1 | 8/2007 | Lang et al. |
| 2007/0203430 A1 | 8/2007 | Lang et al. |
| 2007/0203583 A1 | 8/2007 | Slone |
| 2007/0203605 A1 | 8/2007 | Melton et al. |
| 2007/0219562 A1 | 9/2007 | Slone et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0225719 A1 | 9/2007 | Stone et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor, III et al. |
| 2007/0239481 A1 | 10/2007 | Disilvestro et al. |
| 2007/0244457 A1 | 10/2007 | Fangrow |
| 2007/0244487 A1 | 10/2007 | Ammann et al. |
| 2007/0250169 A1 | 10/2007 | Lang |
| 2007/0250175 A1 | 10/2007 | Meridew et al. |
| 2007/0253617 A1 | 11/2007 | Arata et al. |

(56) References Cited

U.S. PATENT DOCUMENTS

| | | |
|---|---|---|
| 2007/0255030 A1 | 11/2007 | Sakamoto et al. |
| 2007/0255255 A1 | 11/2007 | Shah et al. |
| 2007/0255288 A1 | 11/2007 | Mahfouz et al. |
| 2007/0255412 A1 | 11/2007 | Hajaj et al. |
| 2007/0262567 A1 | 11/2007 | Benson |
| 2007/0262867 A1 | 11/2007 | Westrick et al. |
| 2007/0270680 A1 | 11/2007 | Sheffer et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0282451 A1 | 12/2007 | Metzger et al. |
| 2007/0288029 A1 | 12/2007 | Justin et al. |
| 2007/0288030 A1 | 12/2007 | Metzger et al. |
| 2008/0009874 A1 | 1/2008 | Meridew et al. |
| 2008/0009952 A1 | 1/2008 | Hodge |
| 2008/0014618 A1 | 1/2008 | Amiot et al. |
| 2008/0015599 A1 | 1/2008 | D'alessio et al. |
| 2008/0015603 A1 | 1/2008 | Collazo |
| 2008/0015604 A1 | 1/2008 | Collazo |
| 2008/0015605 A1 | 1/2008 | Collazo |
| 2008/0015607 A1 | 1/2008 | D'Alessio et al. |
| 2008/0021299 A1 | 1/2008 | Meulink |
| 2008/0021494 A1 | 1/2008 | Schmelzeisen-redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0039850 A1 | 2/2008 | Rowley et al. |
| 2008/0051799 A1 | 2/2008 | Bonutti et al. |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0094396 A1 | 4/2008 | Sabczynsdi et al. |
| 2008/0097451 A1 | 4/2008 | Chen et al. |
| 2008/0112996 A1 | 5/2008 | Harlow et al. |
| 2008/0114370 A1 | 5/2008 | Schoenefeld |
| 2008/0133016 A1 | 6/2008 | Heinz |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0147074 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 | 8/2008 | Minas |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0221699 A1 | 9/2008 | Meridew et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0249395 A1 | 10/2008 | Shachar et al. |
| 2008/0255674 A1 | 10/2008 | Rahaman et al. |
| 2008/0257363 A1 | 10/2008 | Schoenefeld et al. |
| 2008/0262499 A1 | 10/2008 | Giori et al. |
| 2008/0262500 A1 | 10/2008 | Collazo |
| 2008/0262624 A1 | 10/2008 | White et al. |
| 2008/0269596 A1 | 10/2008 | Revie et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287926 A1 | 11/2008 | Abou El |
| 2008/0287954 A1 | 11/2008 | Kunz et al. |
| 2008/0287959 A1 | 11/2008 | Quest et al. |
| 2008/0294170 A1 | 11/2008 | O'brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0312746 A1 | 12/2008 | Unger |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0022015 A1 | 1/2009 | Harrison |
| 2009/0024131 A1 | 1/2009 | Metzger et al. |
| 2009/0024169 A1 | 1/2009 | Triplett et al. |
| 2009/0043556 A1 | 2/2009 | Axelson et al. |
| 2009/0048618 A1 | 2/2009 | Harrison et al. |
| 2009/0066936 A1 | 3/2009 | Huang et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0076555 A1 | 3/2009 | Lowry et al. |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0099570 A1 | 4/2009 | Paradis et al. |
| 2009/0105837 A1 | 4/2009 | Lafosse et al. |
| 2009/0116621 A1 | 5/2009 | Yuan et al. |
| 2009/0118736 A1 | 5/2009 | Kreuzer |
| 2009/0118769 A1 | 5/2009 | Sixto, Jr. et al. |
| 2009/0129067 A1 | 5/2009 | Fan et al. |
| 2009/0131941 A1 | 5/2009 | Park et al. |
| 2009/0131942 A1 | 5/2009 | Aker et al. |
| 2009/0138019 A1 | 5/2009 | Wasielewski |
| 2009/0138020 A1 | 5/2009 | Park et al. |
| 2009/0149964 A1 | 6/2009 | May et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0204225 A1 | 8/2009 | Meridew et al. |
| 2009/0209884 A1 | 8/2009 | Van Vorhis et al. |
| 2009/0209961 A1 | 8/2009 | Ferrante et al. |
| 2009/0210067 A1 | 8/2009 | Meridew |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez |
| 2009/0234217 A1 | 9/2009 | Mire et al. |
| 2009/0234302 A1 | 9/2009 | Hoendervoogt et al. |

(56) References Cited

U.S. PATENT DOCUMENTS

| | | |
|---|---|---|
| 2009/0234360 A1 | 9/2009 | Alexander |
| 2009/0248044 A1 | 10/2009 | Amiot et al. |
| 2009/0250413 A1 | 10/2009 | Hoeppner |
| 2009/0254093 A1 | 10/2009 | White et al. |
| 2009/0254367 A1 | 10/2009 | Belcher et al. |
| 2009/0259312 A1 | 10/2009 | Shterling et al. |
| 2009/0270868 A1 | 10/2009 | Park et al. |
| 2009/0274350 A1 | 11/2009 | Pavlovskaia et al. |
| 2009/0287217 A1 | 11/2009 | Ammann et al. |
| 2009/0287309 A1 | 11/2009 | Walch et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2009/0318930 A1 | 12/2009 | Stone et al. |
| 2009/0318931 A1 | 12/2009 | Stone et al. |
| 2010/0010493 A1 | 1/2010 | Dower |
| 2010/0015082 A1 | 1/2010 | Ting-jenulis et al. |
| 2010/0016705 A1 | 1/2010 | Stone et al. |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0036404 A1 | 2/2010 | Yi et al. |
| 2010/0042105 A1 | 2/2010 | Park et al. |
| 2010/0049195 A1 | 2/2010 | Park et al. |
| 2010/0049327 A1 | 2/2010 | Isch et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0082067 A1 | 4/2010 | Kondrashov |
| 2010/0087829 A1 | 4/2010 | Metzger |
| 2010/0094295 A1 | 4/2010 | Schnieders et al. |
| 2010/0099977 A1 | 4/2010 | Hershberger |
| 2010/0100011 A1 | 4/2010 | Roche |
| 2010/0105011 A1 | 4/2010 | Karkar et al. |
| 2010/0121334 A1 | 5/2010 | Couture et al. |
| 2010/0121335 A1 | 5/2010 | Penenberg et al. |
| 2010/0131073 A1 | 5/2010 | Meridew et al. |
| 2010/0136214 A1 | 6/2010 | Kumar |
| 2010/0137869 A1 | 6/2010 | Borja et al. |
| 2010/0137871 A1 | 6/2010 | Borja |
| 2010/0137924 A1 | 6/2010 | Tuke et al. |
| 2010/0139377 A1 | 6/2010 | Huang et al. |
| 2010/0145343 A1 | 6/2010 | Johnson et al. |
| 2010/0145344 A1 | 6/2010 | Jordan et al. |
| 2010/0145466 A1 | 6/2010 | Slone |
| 2010/0152782 A1 | 6/2010 | Stone et al. |
| 2010/0160917 A1 | 6/2010 | Fitz et al. |
| 2010/0160919 A1 | 6/2010 | Axelson, Jr. et al. |
| 2010/0168752 A1 | 7/2010 | Edwards |
| 2010/0168754 A1 | 7/2010 | Fitz et al. |
| 2010/0168857 A1 | 7/2010 | Hatch |
| 2010/0168866 A1 | 7/2010 | Shih |
| 2010/0179663 A1 | 7/2010 | Steinberg |
| 2010/0185202 A1 | 7/2010 | Lester et al. |
| 2010/0191244 A1 | 7/2010 | White et al. |
| 2010/0198067 A1 | 8/2010 | Mahfouz et al. |
| 2010/0198224 A1 | 8/2010 | Metzger |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0217399 A1 | 8/2010 | Groh |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0256649 A1 | 10/2010 | Capsal et al. |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0286789 A1 | 11/2010 | Meridew |
| 2010/0291401 A1 | 11/2010 | Medina et al. |
| 2010/0292743 A1 | 11/2010 | Singhal et al. |
| 2010/0298894 A1 | 11/2010 | Bojarski et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0008754 A1 | 1/2011 | Bassett et al. |
| 2011/0009869 A1 | 1/2011 | Marino et al. |
| 2011/0014081 A1 | 1/2011 | Jones et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0015752 A1 | 1/2011 | Meridew |
| 2011/0015753 A1 | 1/2011 | Meridew |
| 2011/0016690 A1 | 1/2011 | Narainasamy et al. |
| 2011/0022049 A1 | 1/2011 | Huebner et al. |
| 2011/0022174 A1 | 1/2011 | Holdstein et al. |
| 2011/0029088 A1 | 2/2011 | Rauscher et al. |
| 2011/0029091 A1 | 2/2011 | Bojarski et al. |
| 2011/0029093 A1 | 2/2011 | Bojarski |
| 2011/0029116 A1 | 2/2011 | Jordan et al. |
| 2011/0035012 A1 | 2/2011 | Linares |
| 2011/0040303 A1 | 2/2011 | Iannotti |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0060339 A1 | 3/2011 | De |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0071581 A1 | 3/2011 | Lang et al. |
| 2011/0071802 A1 | 3/2011 | Bojarski et al. |
| 2011/0087332 A1 | 4/2011 | Bojarski et al. |
| 2011/0092804 A1 | 4/2011 | Schoenefeld et al. |
| 2011/0093086 A1 | 4/2011 | Witt et al. |
| 2011/0106093 A1 | 5/2011 | Romano et al. |
| 2011/0106254 A1 | 5/2011 | Abel et al. |
| 2011/0125264 A1 | 5/2011 | Bagga et al. |
| 2011/0125284 A1 | 5/2011 | Gabbrielli et al. |
| 2011/0130795 A1 | 6/2011 | Ball |
| 2011/0151027 A1 | 6/2011 | Clineff et al. |
| 2011/0151259 A1 | 6/2011 | Jarman-Smith et al. |
| 2011/0153025 A1 | 6/2011 | Mcminn |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0177590 A1 | 7/2011 | Clyne et al. |
| 2011/0184419 A1 | 7/2011 | Meridew et al. |
| 2011/0184424 A1 | 7/2011 | Isch et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0238071 A1 | 9/2011 | Fernandez-scoma |
| 2011/0245835 A1 | 10/2011 | Dodds et al. |
| 2011/0251617 A1 | 10/2011 | Ammann et al. |
| 2011/0257657 A1 | 10/2011 | Turner et al. |
| 2011/0269100 A1 | 11/2011 | Furrer et al. |
| 2011/0275032 A1 | 11/2011 | Tardieu et al. |
| 2011/0276053 A1 | 11/2011 | Birkbeck et al. |
| 2011/0276145 A1 | 11/2011 | Carignan et al. |
| 2011/0282473 A1 | 11/2011 | Pavlovskaia et al. |
| 2011/0295887 A1 | 12/2011 | Palmese et al. |
| 2011/0313424 A1 | 12/2011 | Bono et al. |
| 2011/0319745 A1 | 12/2011 | Frey |
| 2012/0010619 A1 | 1/2012 | Barsoum |
| 2012/0010710 A1 | 1/2012 | Frigg |

(56) References Cited

U.S. PATENT DOCUMENTS

| | | |
|---|---|---|
| 2012/0010711 A1 | 1/2012 | Antonyshyn et al. |
| 2012/0029345 A1 | 2/2012 | Mahfouz et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0041564 A1 | 2/2012 | Landon |
| 2012/0053590 A1 | 3/2012 | Allen et al. |
| 2012/0063655 A1 | 3/2012 | Dean et al. |
| 2012/0065640 A1 | 3/2012 | Metzger et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0089595 A1 | 4/2012 | Jaecksch et al. |
| 2012/0101586 A1 | 4/2012 | Carson |
| 2012/0109137 A1 | 5/2012 | Iannotti et al. |
| 2012/0109138 A1 | 5/2012 | Meridew et al. |
| 2012/0109226 A1 | 5/2012 | Iannotti et al. |
| 2012/0116203 A1 | 5/2012 | Vancraen et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0136365 A1 | 5/2012 | Iannotti et al. |
| 2012/0141034 A1 | 6/2012 | Iannotti et al. |
| 2012/0143197 A1 | 6/2012 | Lang et al. |
| 2012/0143267 A1 | 6/2012 | Iannotti et al. |
| 2012/0150242 A1 | 6/2012 | Mannion |
| 2012/0158002 A1 | 6/2012 | Carignan et al. |
| 2012/0165954 A1 | 6/2012 | Nimal |
| 2012/0190971 A1 | 7/2012 | De |
| 2012/0192401 A1 | 8/2012 | Pavlovskaia et al. |
| 2012/0196314 A1 | 8/2012 | Nawaz et al. |
| 2012/0209276 A1 | 8/2012 | Schuster |
| 2012/0215225 A1 | 8/2012 | Philippon et al. |
| 2012/0215310 A1 | 8/2012 | Sharp et al. |
| 2012/0221017 A1 | 8/2012 | Bonutti |
| 2012/0226283 A1 | 9/2012 | Meridew et al. |
| 2012/0232596 A1 | 9/2012 | Ribeiro |
| 2012/0245587 A1 | 9/2012 | Fang et al. |
| 2012/0245647 A1 | 9/2012 | Kunz et al. |
| 2012/0259335 A1 | 10/2012 | Scifert et al. |
| 2012/0265208 A1 | 10/2012 | Smith |
| 2012/0271131 A1 | 10/2012 | Kling et al. |
| 2012/0271314 A1 | 10/2012 | Stemniski et al. |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289965 A1 | 11/2012 | Gelaude et al. |
| 2012/0296339 A1 | 11/2012 | Iannotti et al. |
| 2012/0303004 A1 | 11/2012 | Uthgenannt et al. |
| 2012/0303033 A1 | 11/2012 | Weiner et al. |
| 2012/0310364 A1 | 12/2012 | Li et al. |
| 2012/0310399 A1 | 12/2012 | Metzger |
| 2012/0316564 A1 | 12/2012 | Serbousek et al. |
| 2012/0323246 A1 | 12/2012 | Catanzarite et al. |
| 2012/0323282 A1 | 12/2012 | Brianza et al. |
| 2012/0323323 A1 | 12/2012 | Vargas et al. |
| 2012/0330319 A1 | 12/2012 | Birkbeck et al. |
| 2013/0001121 A1 | 1/2013 | Metzger |
| 2013/0006250 A1 | 1/2013 | Metzger et al. |
| 2013/0018483 A1 | 1/2013 | Li et al. |
| 2013/0035766 A1 | 2/2013 | Meridew |
| 2013/0046310 A1 | 2/2013 | Ranawat et al. |
| 2013/0053854 A1 | 2/2013 | Schoenefeld et al. |
| 2013/0056912 A1 | 3/2013 | O'neill et al. |
| 2013/0060253 A1 | 3/2013 | Couture et al. |
| 2013/0066323 A1 | 3/2013 | Nycz et al. |
| 2013/0072940 A1 | 3/2013 | Dawood et al. |
| 2013/0085500 A1 | 4/2013 | Meridew et al. |
| 2013/0085590 A1 | 4/2013 | Bryan et al. |
| 2013/0110116 A1 | 5/2013 | Kehres et al. |
| 2013/0110470 A1 | 5/2013 | Vanasse et al. |
| 2013/0116699 A1 | 5/2013 | Smith et al. |
| 2013/0119579 A1 | 5/2013 | Iannotti et al. |
| 2013/0123850 A1 | 5/2013 | Schoenefeld et al. |
| 2013/0131681 A1 | 5/2013 | Katrana et al. |
| 2013/0144392 A1 | 6/2013 | Hughes |
| 2013/0158671 A1 | 6/2013 | Uthgenannt et al. |
| 2013/0197528 A1 | 8/2013 | Zakaria et al. |
| 2013/0197529 A1 | 8/2013 | Metzger et al. |
| 2013/0197687 A1 | 8/2013 | Pavlovskaia et al. |
| 2013/0218163 A1 | 8/2013 | Frey |
| 2013/0245631 A1 | 9/2013 | Bettenga |
| 2013/0245801 A1 | 9/2013 | Schroeder |
| 2013/0261503 A1 | 10/2013 | Sherman et al. |
| 2013/0264749 A1 | 10/2013 | Jones et al. |
| 2013/0268085 A1 | 10/2013 | Dong |
| 2013/0289730 A1 | 10/2013 | Gabriel et al. |
| 2013/0292870 A1 | 11/2013 | Roger |
| 2013/0317511 A1 | 11/2013 | Bojarski et al. |
| 2013/0317621 A1 | 11/2013 | Metzger et al. |
| 2013/0326878 A1 | 12/2013 | Boehm et al. |
| 2013/0338673 A1 | 12/2013 | Keppler |
| 2014/0001226 A1 | 1/2014 | Scabin et al. |
| 2014/0005672 A1 | 1/2014 | Edwards et al. |
| 2014/0012266 A1 | 1/2014 | Bonin, Jr. et al. |
| 2014/0018934 A1 | 1/2014 | Meridew et al. |
| 2014/0052270 A1 | 2/2014 | Witt et al. |
| 2014/0066937 A1 | 3/2014 | Wiebe, III et al. |
| 2014/0081659 A1 | 3/2014 | Nawana et al. |
| 2014/0088724 A1 | 3/2014 | Meridew |
| 2014/0094816 A1 | 4/2014 | White et al. |
| 2014/0100578 A1 | 4/2014 | Metzger et al. |
| 2014/0107651 A1 | 4/2014 | Meridew et al. |
| 2014/0107654 A1 | 4/2014 | Kehres et al. |
| 2014/0107715 A1 | 4/2014 | Heilman et al. |
| 2014/0081275 A1 | 5/2014 | Metzger et al. |
| 2014/0127211 A1 | 5/2014 | Geles et al. |
| 2014/0135775 A1 | 5/2014 | Maxson |
| 2014/0163564 A1 | 6/2014 | Bollinger |
| 2014/0163565 A1 | 6/2014 | Bollinger |
| 2014/0172116 A1 | 6/2014 | Maxson et al. |
| 2014/0188119 A1 | 7/2014 | Catanzarite et al. |
| 2014/0222157 A1 | 8/2014 | Al Hares et al. |
| 2014/0243833 A1 | 8/2014 | Smith |
| 2014/0257304 A1 | 9/2014 | Eash |
| 2014/0257508 A1 | 9/2014 | Bojarski et al. |
| 2014/0276854 A1 | 9/2014 | Schoenefeld et al. |
| 2014/0276856 A1 | 9/2014 | Schoenfeld |
| 2014/0276870 A1 | 9/2014 | Eash |
| 2014/0276873 A1 | 9/2014 | Meridew et al. |
| 2014/0303938 A1 | 10/2014 | Schoenefeld et al. |
| 2014/0303990 A1 | 10/2014 | Schoenefeld et al. |
| 2014/0309644 A1 | 10/2014 | Metzger et al. |
| 2014/0324058 A1 | 10/2014 | Metzger et al. |
| 2014/0378979 A1 | 12/2014 | Stone et al. |
| 2015/0088293 A1 | 3/2015 | Metzger |
| 2015/0112348 A1 | 4/2015 | Schoenefeld et al. |
| 2015/0112349 A1 | 4/2015 | Schoenefeld |
| 2015/0150688 A1 | 6/2015 | Vanasse et al. |
| 2015/0157341 A1 | 6/2015 | Catanzarite et al. |
| 2015/0320429 A1 | 11/2015 | Katrana et al. |
| 2015/0320508 A1 | 11/2015 | White et al. |
| 2015/0335438 A1 | 11/2015 | Pierce et al. |
| 2015/0351778 A1 | 12/2015 | Uthgenannt et al. |
| 2016/0008013 A1 | 1/2016 | Metzger et al. |
| 2016/0038160 A1 | 2/2016 | Metzger |
| 2016/0100845 A1 | 4/2016 | Smith et al. |
| 2016/0128706 A1 | 5/2016 | Meridew |
| 2016/0135824 A1 | 5/2016 | Vanasse et al. |
| 2016/0196651 A1 | 7/2016 | Dean et al. |
| 2016/0203241 A1 | 7/2016 | Dean et al. |
| 2016/0213491 A1 | 7/2016 | Schoenefeld et al. |
| 2016/0228133 A1 | 8/2016 | Meridew et al. |
| 2016/0338838 A1 | 11/2016 | Meridew et al. |
| 2017/0000626 A1 | 1/2017 | White et al. |
| 2017/0056030 A1 | 3/2017 | Metzger et al. |
| 2017/0224496 A1 | 8/2017 | Witt et al. |
| 2017/0273718 A1 | 9/2017 | Metzger et al. |
| 2017/0311846 A1 | 11/2017 | Hershberger |
| 2017/0333194 A1 | 11/2017 | Pierce et al. |
| 2018/0140426 A1 | 5/2018 | Belcher et al. |
| 2018/0153565 A1 | 6/2018 | Stone et al. |
| 2018/0168690 A1 | 6/2018 | Uthgenannt et al. |
| 2018/0168822 A1 | 6/2018 | White et al. |

(56) References Cited

U.S. PATENT DOCUMENTS

| | | | |
|---|---|---|---|
| 2018/0206888 A1 | 7/2018 | Metzger et al. | |
| 2018/0250135 A1 | 9/2018 | White et al. | |
| 2018/0256257 A1 | 9/2018 | Luby | |

FOREIGN PATENT DOCUMENTS

| | | | |
|---|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CH | 117960 A | 5/1927 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 102038553 A | 5/2011 |
| CN | 102335742 A | 2/2012 |
| DE | 337437 C | 5/1921 |
| DE | 3447365 A1 | 7/1986 |
| DE | 04219939 A1 | 12/1993 |
| DE | 4421153 A1 | 12/1995 |
| DE | 10341187 A1 | 3/2005 |
| DE | 102009028503 A1 | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0255797 A1 | 2/1988 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1563810 A1 | 8/2005 |
| EP | 1588669 A1 | 10/2005 |
| EP | 1634551 A2 | 3/2006 |
| EP | 1832239 A1 | 9/2007 |
| EP | 1852072 A2 | 11/2007 |
| EP | 1852072 A3 | 11/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| EP | 2502582 A1 | 9/2012 |
| EP | 2709568 A1 | 3/2014 |
| EP | 2816962 A1 | 12/2014 |
| EP | 2029061 B1 | 2/2017 |
| FR | 1111677 A | 3/1956 |
| FR | 2429582 A1 | 1/1980 |
| FR | 2659226 A2 | 9/1991 |
| FR | 2721195 A1 | 12/1995 |
| FR | 2768916 A1 | 4/1999 |
| FR | 2979817 A1 | 3/2013 |
| GB | 2094590 A | 9/1982 |
| GB | 2197790 A | 6/1988 |
| GB | 2423021 A | 8/2006 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| GB | 2486390 B | 11/2015 |
| GB | 2527690 B | 6/2016 |
| GB | 2483980 B | 12/2016 |
| GB | 2491526 B | 1/2017 |
| JP | 59157715 A | 9/1984 |
| JP | 60231208 A | 11/1985 |
| JP | 6233790 A | 8/1994 |
| JP | 2000245758 A | 9/2000 |
| JP | 2004008797 A | 1/2004 |
| JP | 2005218861 A | 8/2005 |
| JP | 2009514612 A | 4/2009 |
| JP | 2009515610 A | 4/2009 |
| JP | 2011505080 A | 2/2011 |
| JP | 2011517996 A | 6/2011 |
| JP | 2011527885 A | 11/2011 |
| JP | 5710014 B2 | 4/2015 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| RU | 2218242 C2 | 12/2003 |
| TW | 231755 A | 5/2005 |
| TW | 201114409 A | 5/2011 |
| WO | WO-8807840 A1 | 10/1988 |
| WO | WO-8909028 A1 | 10/1989 |
| WO | WO-9014806 A1 | 12/1990 |
| WO | WO-9107139 A1 | 5/1991 |
| WO | WO-9325157 A1 | 12/1993 |
| WO | WO-9413218 A1 | 6/1994 |
| WO | WO-9528688 A1 | 10/1995 |
| WO | WO-9607361 A1 | 3/1996 |
| WO | WO-9729703 A1 | 8/1997 |
| WO | WO-9901073 A1 | 1/1999 |
| WO | WO-9952473 A1 | 10/1999 |
| WO | WO-9959106 A1 | 11/1999 |
| WO | WO-0110339 A2 | 2/2001 |
| WO | WO-0133511 A2 | 5/2001 |
| WO | WO-0170142 A1 | 9/2001 |
| WO | WO-0184479 A1 | 11/2001 |
| WO | WO-0217821 A2 | 3/2002 |
| WO | WO-2002026145 A1 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004030556 A2 | 4/2004 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2004112610 A2 | 12/2004 |
| WO | WO-2005051209 A1 | 6/2005 |
| WO | WO-2005051233 A2 | 6/2005 |
| WO | WO-2005051239 A1 | 6/2005 |
| WO | WO-2005051240 A1 | 6/2005 |
| WO | WO-2005077039 A2 | 8/2005 |
| WO | WO-2005099636 A1 | 10/2005 |
| WO | WO-06060795 A1 | 6/2006 |
| WO | WO-2006058057 A2 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-07041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2007145937 A3 | 12/2007 |
| WO | WO-2007147235 A1 | 12/2007 |
| WO | WO-2008014618 A1 | 2/2008 |
| WO | WO-2008021494 A2 | 2/2008 |

(56) References Cited

FOREIGN PATENT DOCUMENTS

| WO | WO-2008040961 A1 | 4/2008 |
|---|---|---|
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009001109 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010045537 A1 | 4/2010 |
| WO | WO-2010048257 A1 | 4/2010 |
| WO | WO-2010088696 A1 | 8/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |
| WO | WO-2010129870 A1 | 11/2010 |
| WO | WO-2010144705 A1 | 12/2010 |
| WO | WO-2010148103 A1 | 12/2010 |
| WO | WO-2010150223 A1 | 12/2010 |
| WO | WO-2011018458 A1 | 2/2011 |
| WO | WO-2011019797 A3 | 2/2011 |
| WO | WO-2011041398 A1 | 4/2011 |
| WO | WO-2011060536 A1 | 5/2011 |
| WO | WO-2011063231 A1 | 5/2011 |
| WO | WO-2011080260 A1 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2011117644 A2 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012058349 A4 | 5/2012 |
| WO | WO-2012058353 A4 | 5/2012 |
| WO | WO-2012058355 A4 | 5/2012 |
| WO | WO-2012061042 A1 | 5/2012 |
| WO | WO-2012116206 A1 | 8/2012 |
| WO | WO-2012141790 A1 | 10/2012 |
| WO | WO-2012158917 A1 | 11/2012 |
| WO | WO-2012173929 A1 | 12/2012 |
| WO | WO-2012174008 A1 | 12/2012 |
| WO | WO-2013126416 A1 | 8/2013 |
| WO | WO-2013170872 A1 | 11/2013 |
| WO | WO-2014019712 A1 | 2/2014 |
| WO | WO-2015084831 A1 | 6/2015 |
| WO | WO-2016007631 A1 | 1/2016 |

OTHER PUBLICATIONS

"U.S. Appl. No. 12/371,096, Notice of Allowance dated Oct. 20, 2017", 5 pgs.

"U.S. Appl. No. 13/527,981, Corrected Notice of Allowance dated Nov. 27, 2017", 2 pgs.

"U.S. Appl. No. 13/527,981, Notice of Allowance dated Nov. 3, 2017", 5 pgs.

"U.S. Appl. No. 14/483,214, Final Office Action dated Oct. 25, 2017", 11 pgs.

"U.S. Appl. No. 14/658,429, Examiner Interview Summary dated Dec. 26, 2017", 2 pgs.

"U.S. Appl. No. 14/658,429, Final Office Action dated Oct. 20, 2017", 11 pgs.

"U.S. Appl. No. 14/658,429, Notice of Allowance dated Feb. 9, 2018", 8 pgs.

"U.S. Appl. No. 14/658,429, Response filed Jan. 4, 2018 to Final Office Action dated Oct. 20, 2017", 20 pgs.

"U.S. Appl. No. 14/739,160, Non Final Office Action dated Jan. 16, 2018", 14 pgs.

"U.S. Appl. No. 14/798,809, Advisory Action dated Feb. 28, 2018", 3 pgs.

"U.S. Appl. No. 14/798,809, Final Office Action dated Dec. 29, 2017", 4 pgs.

"U.S. Appl. No. 14/798,809, Preliminary Amendment filed Oct. 29, 2015", 7 pgs.

"U.S. Appl. No. 14/798,809, Response filed Feb. 21, 2018 to Final Office Action dated Dec. 29, 2017", 7 pgs.

"U.S. Appl. No. 14/798,809, Response Filed Mar. 29, 2018 to Advisory Action dated Feb. 28, 2018", 8 pgs.

"U.S. Appl. No. 14/865,762, Final Office Action dted Mar. 8, 2018", 14 pgs.

"U.S. Appl. No. 14/983,077, Non Final Office Action dated Jan. 4, 2018", 6 pgs.

"U.S. Appl. No. 15/008,528, Response filed Dec. 7, 2017 to Restriction Requirement dated Oct. 12, 2017", 7 pgs.

"U.S. Appl. No. 15/008,528, Restriction Requirement dated Oct. 12, 2017", 6 pgs.

"U.S. Appl. No. 15/130,414, Response filed Apr. 2, 2018 to Restriction Requirement dated Feb. 6, 2018", 7 pgs.

"U.S. Appl. No. 15/130,414, Response filed Nov. 6, 2017 to Restriction Requirement dated Sep. 20, 2017", 8 pgs.

"U.S. Appl. No. 15/130,414, Restriction Requirement dated Feb. 6, 2018", 8 pgs.

"U.S. Appl. No. 15/224,741, Restriction Requirement dated Mar. 15, 2018", 7 pgs.

"U.S. Appl. No. 15/267,714, Notice of Allowance dated Oct. 10, 2017", 13 pgs.

"U.S. Appl. No. 15/495,432, Response filed Apr. 4, 2018 to Restriction Requirement dated Feb. 9, 2018", 10 pgs.

"U.S. Appl. No. 15/495,432, Restriction Requirement dated Feb. 9, 2018", 8 pgs.

"U.S. Appl. No. 15/618,331, Notice of Allowance dated Jan. 10, 2018", 10 pgs.

"U.S. Appl. No. 15/863,421, Preliminary Amendment Filed Mar. 13, 2018", 9 pgs.

"U.S. Appl. No. 15/875,204, Preliminary Amendment filed Mar. 8, 2018", 9 pgs.

"U.S. Appl. No. 15/878,984, Preliminary Amendment Filed Mar. 9, 2018", 8 pgs.

"European Application Serial No. 16179349.2, Response filed Oct. 19, 2017 to Extended European Search Report dated Mar. 22, 2017", 17 pgs.

"European Application Serial No. 16179569.5, Response filed Feb. 7, 2018 to Extended European Search Report dated Jul. 7, 2017", 14 pgs.

"German Application Serial No. 1120111008104, Office Action dated Oct. 18, 2017", (W/ English translation of claims), 7 pgs.

"German Application Serial No. 1120111008104, Response filed Feb. 23, 2018 to Office Action dated Oct. 18, 2017", (W/ English translation of claims), 8 pgs.

Kwon, Oh-Ryong, et al., "The Effect of Femoral Cutting Guide Design Improvements for Patient-Specific Instruments", BioMed Research International, vol. 2015, Article ID 978686; https://www.hindawi.com/journals/bmri/2015/978686/, (Apr. 20, 2015), 9 pgs.

MacDessi, S., et al., "Patient-specific cutting guides for total knee arthroplasty", Cochrane Database of Systematic Reviews, Issue 3. Art. No. CD012589; http://onlinelibrary.wiley.com/doi/10.1002/14651858.CD012589/full, (Mar. 13, 2017), 16 pgs.

"U.S. Appl. No. 12/371,096, Appeal Decision mailed Jun. 23, 2017", 10 pgs.

"U.S. Appl. No. 13/088,787, Notice of Allowance dated Oct. 21, 2015", 6 pgs.

"U.S. Appl. No. 13/088,787, Response filed May 12, 2014 to Restriction Requirement dated Mar. 12, 2014", 10 pgs.

"U.S. Appl. No. 13/088,787, Response filed Aug. 20, 2015 to Final Office Action dated May 20, 2015", 9 pgs.

"U.S. Appl. No. 13/088,787, Response filed Dec. 10, 2014 to Non Final Office Action dated Sep. 11, 2014", 11 pgs.

"U.S. Appl. No. 13/527,981, Non Final Office Action dated Jun. 22, 2017", 6 pgs.

"U.S. Appl. No. 13/527,981, Response filed Sep. 21, 2017 to Non Final Office Action dated Jun. 22, 2017", 11 pgs.

(56) References Cited

OTHER PUBLICATIONS

"U.S. Appl. No. 13/674,531 Response Filed Mar. 30, 2016 to Non-Final Office Action dated Sep. 30, 2015", 10 pgs.
"U.S. Appl. No. 13/674,531, Advisory Action dated Aug. 6, 2015", 3 pgs.
"U.S. Appl. No. 13/674,531, Non Final Office Action dated Sep. 30, 2015", 8 pgs.
"U.S. Appl. No. 13/674,531, Non Final Office Action dated Dec. 1, 2014", 9 pgs.
"U.S. Appl. No. 13/674,531, Notice of Allowance dated Jun. 14, 2016", 16 pgs.
"U.S. Appl. No. 13/674,531, Response filed Mar. 2, 2015 to Non Final Office Action dated Dec. 1, 2014", 12 pgs.
"U.S. Appl. No. 13/674,531, Response filed Oct. 9, 2014 to Restriction Requirement dated Sep. 24, 2014", 3 pgs.
"U.S. Appl. No. 13/800,334, Final Office Action dated Jun. 15, 2017", 22 pgs.
"U.S. Appl. No. 13/800,334, Notice of Allowance dated Aug. 31, 2017", 8 pgs.
"U.S. Appl. No. 14/483,214, Response filed Jul. 31, 2017 to Non Final Office Action dated May 2, 2017", 12 pgs.
"U.S. Appl. No. 14/658,429, Advisory Action dated Sep. 12, 2017", 3 pgs.
"U.S. Appl. No. 14/658,429, Examiner Interview Summary dated Aug. 17, 2017", 2 pgs.
"U.S. Appl. No. 14/658,429, Final Office Action dated Jun. 15, 2017", 7 pgs.
"U.S. Appl. No. 14/658,429, Response Filed May 19, 2017 to Non-Final Office Action dated Feb. 23, 2017", 15 pgs.
"U.S. Appl. No. 14/658,429, Response filed Aug. 11, 2017 to Final Office Action dated Jun. 15, 2017", 21 pgs.
"U.S. Appl. No. 14/658,429, Supplemental Response Filed Sep. 21, 2017 to Final Office Action dated Jun. 15, 2017 and Advisory Action dated Sep. 12, 2017", 25 pgs.
"U.S. Appl. No. 14/798,809, Examiner Interview Summary dated Sep. 14, 2017", 3 pgs.
"U.S. Appl. No. 14/798,809, Non Final Office Action dated Jun. 28, 2017", 7 pgs.
"U.S. Appl. No. 14/798,809, Response filed Sep. 26, 2017 to Non Final Office Action dated Jun. 28, 2017", 9 pgs.
"U.S. Appl. No. 14/865,762, Non Final Office Action dared Jun. 13, 2017", 13 pgs.
"U.S. Appl. No. 14/865,762, Response filed May 17, 2017 to Restrictiion Requirement dated Apr. 13, 2017", 8 pgs.
"U.S. Appl. No. 14/865,762, Response filed Sep. 13, 2017 to Non Final Office Action dated Jun. 13, 2017", 17 pgs.
"U.S. Appl. No. 14/973,057, Corrected Notice of Allowance dated May 30, 2017", 2 pgs.
"U.S. Appl. No. 14/983,077, Preliminary Amendment filed Dec. 30, 2015", 6 pgs.
"U.S. Appl. No. 15/130,414, Restriction Requirement dated Sep. 20, 2017", 7 pgs.
"U.S. Appl. No. 15/267,714, Response filed Aug. 4, 2017 to Non Final Office Action dated May 10, 2017", 21 pgs.
"U.S. Appl. No. 15/495,432, Preliminary Amendment filed May 17, 2017", 8 pgs.
"U.S. Appl. No. 15/618,331, Preliminary Amendment filed Jun. 28, 2017", 6 pgs.
"U.S. Appl. No. 15/650,035, Preliminary Amendment filed Jul. 20, 2017", 6 pgs.
"U.S. Appl. No. 15/672,724, Preliminary Amendment Filed Aug. 9, 2017", 4 pgs.
"U.S. Appl. No. 15/672,724, Supplemental Preliminary Amendment filed Aug. 23, 2017", 7 pgs.
"U.S. Appl. No. 13/800,334, Response filed Aug. 10, 2017 to Final Office Action dated Jun. 15, 2017", 9 pgs.
"C2a-Taper™ Ceramic-on-Ceramic Articulation", Surgical Technique, Biomet Orthopedics, (2007), 20 pgs.
"European Application Serial No. 15739458.6, Response filed Sep. 4, 2017 to Communication pursuant to Rules 161(1) and 162 EPC dated Feb. 21, 2017", 9 pgs.
"European Application Serial No. 16179569.5, Extended European Search Report dated Jul. 7, 2017", 8 pgs.
"International Application Serial No. PCT/US2010/028325, International Preliminary Report on Patentability dated Oct. 6, 2011", 8 pgs.
"International Application Serial No. PCT/US2010/028325, International Search Report dated Jun. 11, 2010", 6 pgs.
"International Application Serial No. PCT/US2010/028325, Written Opinion dated Jun. 11, 2010", 6 pgs.
"International Application Serial No. PCT/US2012/060848, International Search Report dated Apr. 12, 2013", 6 pgs.
"Vision Acetabular Surgical TechniQue", Biomet Orthopedics, Inc brochure, (2001), 16 pgs.
"3D-Implantatplanung und StereolithographieImplantatbohrschablonen", Stomatologie 101.3, (2004), 55-59.
"AGC 3000 Intramedullary",—Surgical Technique Using PMMA Fixation—Biomet, Inc., (1987), 32 pgs.
"AGC Distal Fem Cutter for Dr. Hardy", Biomet, Inc., (Jun. 22, 1989), 4 pgs.
"AGC Total Knee System, Intramedullary Without Distractor Surgical Technique", Biomet, Inc., (1989), 35 pgs.
"AGC Total Knee System, Unicondylar Surgical Overview", Biomet, Inc., (Jan. 31, 1989), 5 pgs.
"AGC Traditional Surgical Overview", Biomet Orthopedics, Inc., (2001), 8 pgs.
"AGC-S Total Knee System, Surgical Technique for the AGC-S Total Knee System", Biomet, Inc., (1992), 22 pgs.
"Amazing Precision. Beautiful Results. The next evolution of MAKOplasty® is here", MAKO Surgical Corp., (Feb. 2009), 6 pgs.
"Anatomic Axial Alignment Instrumentation", Biomet, Inc., (1994), 24 pgs.
"U.S. Appl. No. 09/861,859, 312 Amendment filed Sep. 27, 2011", 3 pgs.
"U.S. Appl. No. 09/861,859, Final Office Action dated Aug. 5, 2011", 10 pgs.
"U.S. Appl. No. 09/861,859, Non Final Office Action dated Mar. 3, 2011", 9 pgs.
"U.S. Appl. No. 09/861,859, Notice of Allowance dated Sep. 8, 2011", 5 pgs.
"U.S. Appl. No. 09/861,859, Notice of Non Compliant Amendment dated Nov. 18, 2010", 3 pgs.
"U.S. Appl. No. 09/861,859, PTO Response to Rule 312 Communication dated Oct. 7, 2011", 2 pgs.
"U.S. Appl. No. 09/861,859, Response filed May 12, 2011 to Non Final Office Action dated Mar. 11, 2011", 13 pgs.
"U.S. Appl. No. 09/861,859, Response filed Aug. 22, 2011 to Final Office Action dated Aug. 5, 2011", 9 pgs.
"U.S. Appl. No. 09/861,859, Response filed Oct. 28, 2010 to Restriction Requirement dated Sep. 29, 2010", 1 pg.
"U.S. Appl. No. 09/861,859, Response filed Nov. 29, 2010 to Notice of Non Compliant Amendment dated Nov. 18, 2010", 8 pgs.
"U.S. Appl. No. 09/861,859, Restriction Requirement dated Sep. 29, 2010", 7 pgs.
"U.S. Appl. No. 11/363,548, Advisory Action dated Aug. 5, 2009", 2 pgs.
"U.S. Appl. No. 11/363,548, Appeal Brief filed Jun. 19, 2009", 52 pgs.
"U.S. Appl. No. 11/363,548, Final Office Action dated Jan. 22, 2009", 12 pgs.
"U.S. Appl. No. 11/363,548, Non Final Office Action dated Jul. 9, 2008", 11 pgs.
"U.S. Appl. No. 11/363,548, Notice of Allowance dated Apr. 9, 2010", 5 pgs.
"U.S. Appl. No. 11/363,548, Response filed Jun. 19, 2009 to Final Office Action dated Jan. 22, 2009", 9 pgs.
"U.S. Appl. No. 11/363,548, Response filed Oct. 8, 2008 to Non Final Office Action dated Jul. 9, 2008", 18 pgs.
"U.S. Appl. No. 11/971,390, Non Final Office Action dated Mar. 3, 2011", 7 pgs.

(56) References Cited

OTHER PUBLICATIONS

"U.S. Appl. No. 11/971,390, Notice of Allowance dated Jul. 26, 2011", 8 pgs.
"U.S. Appl. No. 11/971,390, Preliminary Amendment filed Jan. 14, 2011", 8 pgs.
"U.S. Appl. No. 11/971,390, Response filed May 12, 2011 to Non Final Office Action dated Mar. 3, 2011", 12 pgs.
"U.S. Appl. No. 11/971,390, Response filed Dec. 23, 2010 to Restriction Requirement dated Nov. 23, 2010", 1 pgs.
"U.S. Appl. No. 11/971,390, Restriction Requirement dated Nov. 23, 2010", 6 pgs.
"U.S. Appl. No. 12/039,849, Final Office Action dated Apr. 8, 2012", 7 pgs.
"U.S. Appl. No. 12/039,849, Non Final Office Action dated Mar. 8, 2012", 11 pgs.
"U.S. Appl. No. 12/039,849, Notice of Allowance dated Jun. 6, 2012", 7 pgs.
"U.S. Appl. No. 12/039,849, Response filed Apr. 3, 2012 to Non Final Office Action dated Mar. 8, 2012", 19 pgs.
"U.S. Appl. No. 12/039,849, Response filed May 14, 2012 to Final Office Action dated Apr. 28, 2012", 7 pgs.
"U.S. Appl. No. 12/039,849, Response filed Aug. 30, 2011 to Restriction Requirement dated Aug. 16, 2011", 11 pgs.
"U.S. Appl. No. 12/039,849, Restriction Requirement dated Aug. 16, 2011", 6 pgs.
"U.S. Appl. No. 12/103,824, Examiner Interview Summary dated Jan. 12, 2012", 2 pgs.
"U.S. Appl. No. 12/103,824, Examiner Interview Summary dated Sep. 19, 2011", 3 pgs.
"U.S. Appl. No. 12/103,824, Final Office Action dated Apr. 26, 2012", 19 pgs.
"U.S. Appl. No. 12/103,824, Final Office Action dated Dec. 6, 2011", 20 pgs.
"U.S. Appl. No. 12/103,824, Non Final Office Action dated Aug. 17, 2011", 17 pgs.
"U.S. Appl. No. 12/103,824, Response filed Sep. 15, 2011 to Non Final Office Action dated Aug. 17, 2011", 16 pgs.
"U.S. Appl. No. 12/103,834 , Final Office Action dated Dec. 8, 2010", 11 pgs.
"U.S. Appl. No. 12/103,834 , Non Final Office Action dated Jun. 22, 2010", 9 pgs.
"U.S. Appl. No. 12/103,834 , Response filed Feb. 3, 2011 to Final Office Action dated Dec. 8, 2010", 5 pgs.
"U.S. Appl. No. 12/103,834 , Response filed Sep. 21, 2010 to Non Final Office Action dated Jun. 22, 2010", 11 pgs.
"U.S. Appl. No. 12/103,834, Notice of Allowance dated Feb. 23, 2011", 9 ogs.
"U.S. Appl. No. 12/103,834, Response filed Mar. 8, 2010 to Restriction Requirement dated Feb. 18, 2010", 9 pgs.
"U.S. Appl. No. 12/103,834, Restriction Requirement dated Feb. 18, 2010", 9 pgs.
"U.S. Appl. No. 12/211,407, Examiner Interview Summary dated Jan. 13, 2012", 3 pgs.
"U.S. Appl. No. 12/211,407, Examiner Interview Summary dated Dec. 5, 2013", 3 pgs.
"U.S. Appl. No. 12/211,407, Final Office Action dated Nov. 25, 2011", 14 pgs.
"U.S. Appl. No. 12/211,407, Non Final Office Action dated Aug. 17, 2011", 15 pgs.
"U.S. Appl. No. 12/211,407, Notice of Allowance dated Aug. 7, 2013", 12 pgs.
"U.S. Appl. No. 12/211,407, Response filed Jan. 16, 2012 to Final Office Action dated Nov. 25, 2011", 18 pgs.
"U.S. Appl. No. 12/211,407, Response filed Aug. 29, 2011 to Non Final Office Action dated Aug. 17, 2011", 19 pgs.
"U.S. Appl. No. 12/255,945, Advisory Action dated Feb. 5, 2014", 3 pgs.
"U.S. Appl. No. 12/255,945, Advisory Action dated Feb. 10, 2012", 3 pgs.
"U.S. Appl. No. 12/255,945, Advisory Action dated Mar. 27, 2014", 3 pgs.
"U.S. Appl. No. 12/255,945, Appeal Brief filed Mar. 26, 2014", 29 pgs.
"U.S. Appl. No. 12/255,945, Appeal Brief filed Oct. 13, 2014", 30 pgs.
"U.S. Appl. No. 12/255,945, Appeal Decision mailed Feb. 27, 2017", 12 pgs.
"U.S. Appl. No. 12/255,945, Examiner Interview Summary dated Aug. 13, 2013", 3 pgs.
"U.S. Appl. No. 12/255,945, Examiner Interview Summary dated Sep. 22, 2011", 3 pgs.
"U.S. Appl. No. 12/255,945, Examiner's Answer dated Feb. 12, 2015", 26 pgs.
"U.S. Appl. No. 12/255,945, Final Office Action dated Sep. 30, 2013", 21 pgs.
"U.S. Appl. No. 12/255,945, Final Office Action dated Nov. 28, 2011", 14 pgs.
"U.S. Appl. No. 12/255,945, Non Final Office Action dated May 7, 2013", 23 pgs.
"U.S. Appl. No. 12/255,945, Non Final Office Action dated Jul. 24, 2014", 26 pgs.
"U.S. Appl. No. 12/255,945, Non Final Office Action dated Aug. 4, 2011", 12 pgs.
"U.S. Appl. No. 12/255,945, Notice of Allowance dated May 5, 2017", 7 pgs.
"U.S. Appl. No. 12/255,945, Reply Brief filed Apr. 13, 2015", 4 pgs.
"U.S. Appl. No. 12/255,945, Response filed Jan. 17, 2012 to Final Office Action dated Nov. 28, 2011", 11 pgs.
"U.S. Appl. No. 12/255,945, Response filed Jan. 28, 2014 to Final Office Action dated Sep. 30, 2013", 13 pgs.
"U.S. Appl. No. 12/255,945, Response filed Feb. 28, 2012 to Advisory Action dated Feb. 10, 2012", 13 pgs.
"U.S. Appl. No. 12/255,945, Response filed Jul. 7, 2011 to Restriction Requirement dated Jun. 7, 2011", 8 pgs.
"U.S. Appl. No. 12/255,945, Response filed Aug. 8, 2013 to Non Final Office Action dated May 7, 2013", 13 pgs.
"U.S. Appl. No. 12/255,945, Response filed Nov. 4, 2011 to Non Final Office Action dated Aug. 4, 2011", 14 pgs.
"U.S. Appl. No. 12/255,945, Restriction Requirement dated Jun. 7, 2011", 8 pgs.
"U.S. Appl. No. 12/255,945, Supplemental Amendment filed Mar. 5, 2014", 13 pgs.
"U.S. Appl. No. 12/371,096, Examiner Interview Summary dated Jan. 13, 2012", 3 pgs.
"U.S. Appl. No. 12/371,096, Examiner Interview Summary dated Dec. 5, 2013", 3 pgs.
"U.S. Appl. No. 12/371,096, Final Office Action dated Jul. 6, 2011", 23 pgs.
"U.S. Appl. No. 12/371,096, Final Office Action dated Nov. 25, 2011", 14 pgs.
"U.S. Appl. No. 12/371,096, Non Final Office Action dated Mar. 30, 2011", 19 pgs.
"U.S. Appl. No. 12/371,096, Non Final Office Action dated Apr. 17, 2014", 23 pgs.
"U.S. Appl. No. 12/371,096, Non Final Office Action dated Aug. 17, 2011", 15 pgs.
"U.S. Appl. No. 12/371,096, Non Final Office Action dated Aug. 28, 2014", 21 pgs.
"U.S. Appl. No. 12/371,096, Notice of Allowance dated Aug. 7, 2013", 12 pgs.
"U.S. Appl. No. 12/371,096, Notice of Allowance dated Nov. 5, 2013", 2 pgs.
"U.S. Appl. No. 12/371,096, Notice of Allowance dated Nov. 15, 2013", 2 pgs.
"U.S. Appl. No. 12/371,096, Response filed Jan. 16, 2012 to Final Office Action dated Nov. 25, 2011", 15 pgs.
"U.S. Appl. No. 12/371,096, Response filed Aug. 29, 2011 to Non Final Office Action dated Aug. 17, 2011", 19 pgs.
"U.S. Appl. No. 12/389,901, Applicant's Summary of Examiner Interview filed Nov. 28, 2011", 1 pg.
"U.S. Appl. No. 12/389,901, Examiner Interview Summary dated Nov. 1, 2011", 3 pgs.

(56) References Cited

OTHER PUBLICATIONS

"U.S. Appl. No. 12/389,901, Non Final Office Action dated May 12, 2011", 6 pgs.
"U.S. Appl. No. 12/389,901, Notice of Allowance dated Sep. 30, 2011", 12 pgs.
"U.S. Appl. No. 12/389,901, Notice of Allowance dated Dec. 7, 2011", 9 pgs.
"U.S. Appl. No. 12/389,901, Response filed Mar. 17, 2011 to Restriction Requirement dated Mar. 2, 2011", 8 pgs.
"U.S. Appl. No. 12/389,901, Response filed Jun. 28, 2011 to Non Final Office Action dated May 12, 2011", 11 pgs.
"U.S. Appl. No. 12/389,901, Restriction Requirement dated Mar. 2, 2011", 6 pgs.
"U.S. Appl. No. 12/483,807, Advisory Action dated Jan. 3, 2012", 2 pgs.
"U.S. Appl. No. 12/483,807, Applicant's Summary of Examiner Interview filed Jan. 19, 2012", 3 pgs.
"U.S. Appl. No. 12/483,807, Applicant's Summary of Examiner Interview filed Dec. 21, 2011", 3 pgs.
"U.S. Appl. No. 12/483,807, Non Final Office Action dated Oct. 3, 2011", 18 pgs.
"U.S. Appl. No. 12/483,807, Notice of Allowance dated Feb. 21, 2013", 9 pgs.
"U.S. Appl. No. 12/483,807, Response filed Jan. 16, 2012 to Advisory Action dated Jan. 3, 2012", 14 pgs.
"U.S. Appl. No. 12/483,807, Response filed Oct. 24, 2011 to Non Final Office Action dated Oct. 3, 2011", 16 pgs.
"U.S. Appl. No. 12/483,807, Response filed Dec. 19, 2011 to Final Office Action dated Nov. 4, 2011", 7 pgs.
"U.S. Appl. No. 12/486,992, Examiner Interview Summary dated Jan. 9, 2012", 3 pgs.
"U.S. Appl. No. 12/486,992, Examiner Interview Summary dated Mar. 9, 2012", 4 pgs.
"U.S. Appl. No. 12/486,992, Final Office Action dated Feb. 21, 2012", 8 pgs.
"U.S. Appl. No. 12/486,992, Non Final Office Action dated Nov. 21, 2011", 9 pgs.
"U.S. Appl. No. 12/486,992, Notice of Allowance dated Jun. 12, 2014", 11 pgs.
"U.S. Appl. No. 12/486,992, Preliminary Amendment filed Mar. 9, 2010", 3 pgs.
"U.S. Appl. No. 12/486,992, Response filed Jan. 17, 2012 to Non Final Office Action dated Nov. 21, 2011", 13 pgs.
"U.S. Appl. No. 12/486,992, Response filed Mar. 12, 2012 to Final Office Action dated Feb. 21, 2012", 10 pgs.
"U.S. Appl. No. 12/486,992, Response filed Oct. 24, 2011 to Restriction Requirement dated Sep. 30, 2011", 7 pgs.
"U.S. Appl. No. 12/486,992, Restriction Requirement dated Sep. 30, 2011", 6 pgs.
"U.S. Appl. No. 12/571,969, Advisory Action dated Oct. 21, 2013", 3 pgs.
"U.S. Appl. No. 12/571,969, Examiner Interview Summary dated Feb. 26, 2015", 3 pgs.
"U.S. Appl. No. 12/571,969, Examiner Interview Summary dated Mar. 11, 2013", 3 pgs.
"U.S. Appl. No. 12/571,969, Final Office Action dated Jan. 15, 2015", 9 pgs.
"U.S. Appl. No. 12/571,969, Final Office Action dated Jul. 31, 2013", 8 pgs.
"U.S. Appl. No. 12/571,969, Non Final Office Action dated Jun. 26, 2014", 8 pgs.
"U.S. Appl. No. 12/571,969, Non Final Office Action dated Dec. 19, 2012", 7 pgs.
"U.S. Appl. No. 12/571,969, Notice of Allowance dated Jun. 23, 2015", 8 pgs.
"U.S. Appl. No. 12/571,969, Preliminary Amendment filed Mar. 16, 2010", 3 pgs.
"U.S. Appl. No. 12/571,969, Response filed Mar. 6, 2013 to Non Final Office Action dated Dec. 19, 2012", 10 pgs.

"U.S. Appl. No. 12/571,969, Response filed May 15, 2015 to Final Office Action dated Jan. 15, 2015", 16 pgs.
"U.S. Appl. No. 12/571,969, Response filed Jun. 4, 2012 to Restriction Requirement dated May 12, 2012", 9 pgs.
"U.S. Appl. No. 12/571,969, Response filed Sep. 26, 2014 to Non Final Office Action dated Jun. 26, 2014", 12 pgs.
"U.S. Appl. No. 12/571,969, Response filed Sep. 30, 2013 to Final Office Action dated Jul. 31, 2013", 13 pgs.
"U.S. Appl. No. 12/571,969, Restriction Requirement dated May 9, 2012", 9 pgs.
"U.S. Appl. No. 12/714,023, Non Final Office Action dated Jan. 26, 2012", 15 pgs.
"U.S. Appl. No. 12/714,023, Notice of Allowance dated Apr. 9, 2012", 10 pgs.
"U.S. Appl. No. 12/714,023, Response filed Jan. 3, 2012 to Restriction Requirement dated Dec. 12, 2011", 9 pgs.
"U.S. Appl. No. 12/714,023, Response filed Feb. 14, 2012 to Non Final Office Action dated Jan. 26, 2012", 15 pgs.
"U.S. Appl. No. 12/714,023, Restriction Requirement dated Dec. 12, 2011", 5 pgs.
"U.S. Appl. No. 12/872,663, Non Final Office Action dated Jun. 20, 2012", 11 pgs.
"U.S. Appl. No. 12/872,663, Notice of Allowance dated Nov. 15, 2012", 9 pgs.
"U.S. Appl. No. 12/872,663, Response filed May 21, 2012 to Restriction Requirement dated Apr. 27, 2012", 7 pgs.
"U.S. Appl. No. 12/872,663, Restriction Requirement dated Apr. 27, 2012", 6 pgs.
"U.S. Appl. No. 12/872,663, Supplemental Amendment filed Nov. 8, 2012", 8 pgs.
"U.S. Appl. No. 12/888,005, Non Final Office Action dated Jun. 1, 2012", 11 pgs.
"U.S. Appl. No. 12/888,005, Notice of Allowance dated Sep. 27, 2012", 6 pgs.
"U.S. Appl. No. 12/888,005, Response filed May 15, 2012 to Restriction Requirement dated Apr. 27, 2012", 7 pgs.
"U.S. Appl. No. 12/888,005, Response filed Jul. 11, 2012 to Non Final Office Action dated Jun. 1, 2012", 12 pgs.
"U.S. Appl. No. 12/888,005, Restriction Requirement daated Apr. 27, 2012", 7 pgs.
"U.S. Appl. No. 12/893,306, Examiner Interview Summary dated Dec. 18, 2014", 3 pgs.
"U.S. Appl. No. 12/893,306, Final Office Action dated Sep. 11, 2014", 8 pgs.
"U.S. Appl. No. 12/893,306, Non Final Office Action dated Feb. 26, 2014", 9 pgs.
"U.S. Appl. No. 12/893,306, Notice of Allowability dated Jul. 29, 2015", 2 pgs.
"U.S. Appl. No. 12/893,306, Notice of Allowance dated Apr. 14, 2015", 5 pgs.
"U.S. Appl. No. 12/893,306, Response filed Jan. 12, 2015 to Final Office Action dated Sep. 11, 2014", 14 pgs.
"U.S. Appl. No. 12/893,306, Response filed May 22, 2014 to Non Final Office Action dated Feb. 26, 2014", 8 pgs.
"U.S. Appl. No. 12/893,306, Response filed Nov. 4, 2013 to Restriction Requirement dated Oct. 4, 2013", 11 pgs.
"U.S. Appl. No. 12/893,306, Restriction Requirement dated Oct. 4, 2013", 11 pgs.
"U.S. Appl. No. 12/938,905, Advisory Action dated Feb. 4, 2013", 3 pgs.
"U.S. Appl. No. 12/938,905, Appeal Brief filed Feb. 28, 2013", 1 pg.
"U.S. Appl. No. 12/938,905, Appeal Brief filed Apr. 29, 2013", 26 pgs.
"U.S. Appl. No. 12/938,905, Appeal Decision mailed Dec. 14, 2015", 18 pgs.
"U.S. Appl. No. 12/938,905, Examiner Interview Summary dated Jan. 30, 2013", 3 pgs.
"U.S. Appl. No. 12/938,905, Examiner Interview Summary dated Jul. 13, 2012", 3 pgs.
"U.S. Appl. No. 12/938,905, Examiner's Answer to Appeal Brief dated Jun. 24, 2013", 8 pgs.
"U.S. Appl. No. 12/938,905, Final Office Action dated Nov. 28, 2012", 11 pgs.

(56) References Cited

OTHER PUBLICATIONS

"U.S. Appl. No. 12/938,905, Non Final Office Action dated Jun. 4, 2012", 11 pgs.
"U.S. Appl. No. 12/938,905, Reply Brief filed Aug. 26, 2013", 12 pgs.
"U.S. Appl. No. 12/938,905, Response filed Jan. 28, 2013 to Final Office Action dated Nov. 28, 2012", 19 pgs.
"U.S. Appl. No. 12/938,905, Response filed May 14, 2012 to Restriction Requirement dated Apr. 17, 2012", 7 pgs.
"U.S. Appl. No. 12/938,905, Response filed Jul. 19, 2012 to Non Final Office Action dated Jun. 4, 2012", 20 pgs.
"U.S. Appl. No. 12/938,905, Response filed Oct. 8, 2012 to Restriction Requirement dated Sep. 14, 2012", 8 pgs.
"U.S. Appl. No. 12/938,905, Restriction Requirement dated Apr. 17, 2012", 8 pgs.
"U.S. Appl. No. 12/938,905, Restriction Requirement dated Sep. 14, 2012", 6 pgs.
"U.S. Appl. No. 12/938,913, Advisory Action dated Jan. 15, 2015", 3 pgs.
"U.S. Appl. No. 12/938,913, Examiner Interview Summary dated Dec. 18, 2014", 3 pgs.
"U.S. Appl. No. 12/938,913, Final Office Action dated Oct. 1, 2014", 9 pgs.
"U.S. Appl. No. 12/938,913, Non Final Office Action dated Mar. 11, 2014", 10 pgs.
"U.S. Appl. No. 12/938,913, Non Final Office Action dated Apr. 9, 2015", 8 pgs.
"U.S. Appl. No. 12/938,913, Notice of Allowance dated Nov. 12, 2015", 5 pgs.
"U.S. Appl. No. 12/938,913, Response filed Jan. 2, 2015 to Final Office Action dated Oct. 1, 2014", 10 pgs.
"U.S. Appl. No. 12/938,913, Response filed Feb. 2, 2015 to Advisory Action dated Jan. 15, 2015", 14 pgs.
"U.S. Appl. No. 12/938,913, Response filed Jun. 11, 2014 to Non Final Office Action dated Mar. 11, 2014", 9 pgs.
"U.S. Appl. No. 12/938,913, Response filed Jul. 7, 2015 to Non Final Office Action dated Apr. 9, 2015", 11 pgs.
"U.S. Appl. No. 12/938,913, Response filed Nov. 6, 2013 to Restriction Requirement dated Oct. 7, 2013", 1 pg.
"U.S. Appl. No. 12/938,913, Restriction Requirement dated Oct. 7, 2013", 7 pgs.
"U.S. Appl. No. 12/955,361, Non Final Office Action dated Mar. 27, 2013", 23 pgs.
"U.S. Appl. No. 12/955,361, Response filed Jun. 27, 2013 to Non Final Office Action dated Mar. 27, 2013", 12 pgs.
"U.S. Appl. No. 12/955,361, Notice of Allowance dated Jul. 18, 2013", 9 pgs.
"U.S. Appl. No. 12/955,361, Notice of Allowance dated Oct. 1, 2013", 4 pgs.
"U.S. Appl. No. 12/955,361, Notice of Allowance dated Oct. 24, 2013", 4 pgs.
"U.S. Appl. No. 12/955,361, Response filed Jan. 14, 2013 to Restriction Requirement dated Dec. 14, 2012", 13 pgs.
"U.S. Appl. No. 12/955,361, Restriction Requirement dated Dec. 14, 2012", 9 pgs.
"U.S. Appl. No. 12/973,214, Response filed Feb. 21, 2014 to Final Office Action dated Nov. 21, 2013", 16 pgs.
"U.S. Appl. No. 12/973,214, Examiner Interview Summary dated Jan. 24, 2014", 3 pgs.
"U.S. Appl. No. 12/973,214, Final Office Action dated Sep. 9, 2015", 10 pgs.
"U.S. Appl. No. 12/973,214, Final Office Action dated Nov. 21, 2013", 14 pgs.
"U.S. Appl. No. 12/973,214, Non Final Office Action dated Feb. 3, 2015", 14 pgs.
"U.S. Appl. No. 12/973,214, Non Final Office Action dated May 22, 2013", 11 pgs.
"U.S. Appl. No. 12/973,214, Notice of Allowance dated Jan. 11, 2016", 8 pgs.
"U.S. Appl. No. 12/973,214, Response filed Apr. 12, 2013 to Restriction Requirement dated Mar. 13, 2013", 9 pgs.
"U.S. Appl. No. 12/973,214, Response filed Jun. 3, 2015 to Non Final Office Action dated Feb. 3, 2015", 13 pgs.
"U.S. Appl. No. 12/973,214, Response filed Aug. 22, 2013 to Non Final Office Action dated May 22, 2013", 12 pgs.
"U.S. Appl. No. 12/973,214, Response filed Nov. 6, 2015 to Final Office Action dated Sep. 9, 2015", 14 pgs.
"U.S. Appl. No. 12/973,214, Restriction Requirement dated Mar. 13, 2013", 8 pgs.
"U.S. Appl. No. 12/978,069, Advisory Action dated Jun. 12, 2013", 3 pgs.
"U.S. Appl. No. 12/978,069, Examiner Interview Summary dated May 28, 2013", 3 pgs.
"U.S. Appl. No. 12/978,069, Final Office Action dated Mar. 25, 2013", 11 pgs.
"U.S. Appl. No. 12/978,069, Non Final Office Action dated Sep. 11, 2012", 11 pgs.
"U.S. Appl. No. 12/978,069, Notice of Allowance dated Jun. 21, 2013", 13 pgs.
"U.S. Appl. No. 12/978,069, Response filed May 23, 2013 to Final Office Action dated Mar. 25, 2013", 17 pgs.
"U.S. Appl. No. 12/978,069, Response filed Aug. 27, 2012 to Restriction Requirement dated Aug. 10, 2012", 8 pgs.
"U.S. Appl. No. 12/978,069, Response filed Dec. 10, 2012 to Non Final Office Action dated Sep. 11, 2012", 15 pgs.
"U.S. Appl. No. 12/978,069, Restriction Requirement dated Aug. 10, 2012", 11 pgs.
"U.S. Appl. No. 12/978,069, Supplemental Notice of Allowance dated Aug. 9, 2013", 3 pgs.
"U.S. Appl. No. 12/978,069, Supplemental Notice of Allowance dated Sep. 17, 2013", 2 pgs.
"U.S. Appl. No. 13/041,469, Non Final Office Action dated Mar. 22, 2013", 12 pgs.
"U.S. Appl. No. 13/041,469, Notice of Allowance dated Aug. 8, 2013", 6 pgs.
"U.S. Appl. No. 13/041,469, Notice of Allowance dated Oct. 3, 2013", 2 pgs.
"U.S. Appl. No. 13/041,469, Notice of Allowance dated Nov. 19, 2013", 2 pgs.
"U.S. Appl. No. 13/041,469, Response filed Jun. 18, 2013 to Non Final Office Action dated Mar. 22, 2013", 15 pgs.
"U.S. Appl. No. 13/041,469, Response filed Oct. 25, 2012 to Restriction Requirement dated Sep. 25, 2012", 1 pg.
"U.S. Appl. No. 13/041,469, Restriction Requirement dated Sep. 25, 2012", 5 pgs.
"U.S. Appl. No. 13/041,495, Appeal Brief filed Oct. 4, 2013", 39 pgs.
"U.S. Appl. No. 13/041,495, Examiner Interview Summary dated Feb. 20, 2013", 3 pgs.
"U.S. Appl. No. 13/041,495, Examiner Interview Summary dated Aug. 6, 2013", 3 pgs.
"U.S. Appl. No. 13/041,495, Final Office Action dated Jun. 18, 2013", 14 pgs.
"U.S. Appl. No. 13/041,495, Non Final Office Action dated Nov. 2, 2012", 10 pgs.
"U.S. Appl. No. 13/041,495, Non Final Office Action dated Dec. 31, 2013", 11 pgs.
"U.S. Appl. No. 13/041,495, Notice of Allowance dated Jun. 11, 2014", 5 pgs.
"U.S. Appl. No. 13/041,495, Response filed Jan. 31, 2013 to Non Final Office Action dated Nov. 2, 2012", 13 pgs.
"U.S. Appl. No. 13/041,495, Response filed Mar. 31, 2014 to Non Final Office Action dated Dec. 31, 2013", 12 pgs.
"U.S. Appl. No. 13/041,495, Response filed Oct. 8, 2012 to Restriction Requirement dated Sep. 25, 2012", 8 pgs.
"U.S. Appl. No. 13/041,495, Restriction Requirement dated Sep. 25, 2012", 7 pgs.
"U.S. Appl. No. 13/041,495, Supplemental Amendment filed Feb. 20, 2013", 15 pgs.
"U.S. Appl. No. 13/041,665, Examiner Interview Summary dated Apr. 30, 2013", 3 pgs.

(56) References Cited

OTHER PUBLICATIONS

"U.S. Appl. No. 13/041,665, Final Office Action dated Mar. 5, 2013", 10 pgs.
"U.S. Appl. No. 13/041,665, Non Final Office Action dated Sep. 27, 2012", 10 pgs.
"U.S. Appl. No. 13/041,665, Notice of Allowance dated May 16, 2013", 7 pgs.
"U.S. Appl. No. 13/041,665, Response filed May 3, 2013 to Final Office Action dated Mar. 5, 2013", 13 pgs.
"U.S. Appl. No. 13/041,665, Response filed Sep. 17, 2012 to Restriction Requirement dated Aug. 20, 2012", 6 pgs.
"U.S. Appl. No. 13/041,665, Response filed Dec. 27, 2012 to Non Final Office Action dated Sep. 27, 2012", 16 pgs.
"U.S. Appl. No. 13/041,665, Restriction Requirement dated Aug. 20, 2012", 9 pgs.
"U.S. Appl. No. 13/041,883, Advisory Action dated May 18, 2016", 3 pgs.
"U.S. Appl. No. 13/041,883, Appeal Brief filed Jul. 25, 2016", 26 pgs.
"U.S. Appl. No. 13/041,883, Examiner Interview Summary dated Oct. 27, 2014", 3 pgs.
"U.S. Appl. No. 13/041,883, Examiner's Answer dated Mar. 8, 2017", 8 pgs.
"U.S. Appl. No. 13/041,883, Final Office Action dated Jan. 15, 2015", 10 pgs.
"U.S. Appl. No. 13/041,883, Final Office Action dated Feb. 11, 2016", 9 pgs.
"U.S. Appl. No. 13/041,883, Non Final Office Action dated Jun. 26, 2014", 8 pgs.
"U.S. Appl. No. 13/041,883, Non Final Office Action dated Aug. 13, 2015", 10 pgs.
"U.S. Appl. No. 13/041,883, Reply Brief Filed May 2, 2017 to Examiner's Answer dated Mar. 8, 2017", 8 pgs.
"U.S. Appl. No. 13/041,883, Response filed Feb. 17, 2014 to Restriction Requirement dated Jan. 15, 2014", 3 pgs.
"U.S. Appl. No. 13/041,883, Response filed Apr. 7, 2016 to Final Office Action dated Feb. 11, 2016", 17 pgs.
"U.S. Appl. No. 13/041,883, Response filed May 15, 2015 to Final Office Action dated Jan. 15, 2015", 13 pgs.
"U.S. Appl. No. 13/041,883, Response filed Sep. 26, 2014 to Non Final Office Action dated Jun. 26, 2014", 12 pgs.
"U.S. Appl. No. 13/041,883, Response filed Nov. 6, 2015 to Non Final Office Action dated Aug. 13, 2015", 16 pgs.
"U.S. Appl. No. 13/041,883, Restriction Requirement dated Jan. 15, 2014", 9 pgs.
"U.S. Appl. No. 13/045,169, Applicant's Summary of Examiner Interview filed Sep. 21, 2015", 2 pgs.
"U.S. Appl. No. 13/045,169, Examiner Interview Summary dated Sep. 10, 2015", 3 pgs.
"U.S. Appl. No. 13/045,169, Final Office Action dated Dec. 3, 2015", 8 pgs.
"U.S. Appl. No. 13/045,169, Non Final Office Action dated Jun. 4, 2015", 8 pgs.
"U.S. Appl. No. 13/045,169, Non Final Office Action dated Sep. 24, 2014", 9 pgs.
"U.S. Appl. No. 13/045,169, Response filed May 15, 2014 to Restriction Requirement dated Mar. 14, 2014", 10 pgs.
"U.S. Appl. No. 13/045,169, Response filed Aug. 31, 2015 to Non Final Office Action dated Jun. 4, 2015", 14 pgs.
"U.S. Appl. No. 13/045,169, Response filed Dec. 23, 2014 to Non Final Office Action dated Sep. 24, 2014", 10 pgs.
"U.S. Appl. No. 13/045,169, Restriction Requirement dated Mar. 14, 2014", 10 pgs.
"U.S. Appl. No. 13/047,924, Examiner Interview Summary dated Jan. 21, 2015", 3 pgs.
"U.S. Appl. No. 13/047,924, Examiner Interview Summary dated Jan. 25, 2013", 3 pgs.
"U.S. Appl. No. 13/047,924, Examiner Interview Summary dated Sep. 5, 2013", 3 pgs.
"U.S. Appl. No. 13/047,924, Examiner Interview Summary dated Sep. 18, 2012", 3 pgs.
"U.S. Appl. No. 13/047,924, Final Office Action dated Apr. 3, 2015", 16 pgs.
"U.S. Appl. No. 13/047,924, Final Office Action dated Jul. 18, 2013", 14 pgs.
"U.S. Appl. No. 13/047,924, Non Final Office Action dated Sep. 21, 2012", 11 pgs.
"U.S. Appl. No. 13/047,924, Non Final Office Action dated Nov. 3, 2014", 14 pgs.
"U.S. Appl. No. 13/047,924, Response filed Feb. 3, 2015 to Non Final Office Action dated Nov. 3, 2014", 16 pgs.
"U.S. Appl. No. 13/047,924, Response filed May 1, 2013 to Restriction Requirement dated Apr. 1, 2013", 11 pgs.
"U.S. Appl. No. 13/047,924, Response filed Sep. 17, 2012 to Restriction Requirement dated Aug. 20, 2012", 9 pgs.
"U.S. Appl. No. 13/047,924, Response filed Oct. 18, 2013 to Final Office Action dated Jul. 18, 2013", 18 pgs.
"U.S. Appl. No. 13/047,924, Response filed Dec. 20, 2012 to Non Final Office Action dated Sep. 21, 2012", 19 pgs.
"U.S. Appl. No. 13/047,924, Restriction Requirement dated Apr. 1, 2013", 7 pgs.
"U.S. Appl. No. 13/047,924, Restriction Requirement dated Aug. 20, 2012", 8 pgs.
"U.S. Appl. No. 13/081,618, Examiner Interview Summary dated Feb. 5, 2013", 3 pgs.
"U.S. Appl. No. 13/081,618, Examiner Interview Summary dated Aug. 31, 2012".
"U.S. Appl. No. 13/081,618, Final Office Action dated Nov. 19, 2012", 8 pgs.
"U.S. Appl. No. 13/081,618, Non Final Office Action dated Jul. 25, 2012", 7 pgs.
"U.S. Appl. No. 13/081,618, Notice of Allowance dated Feb. 26, 2013", 9 pgs.
"U.S. Appl. No. 13/081,618, Response filed Feb. 25, 2013 to Final Office Action dated Nov. 19, 2012", 12 pgs.
"U.S. Appl. No. 13/081,618, Response filed Aug. 23, 2012 to Non Final Office Action dated Jul. 25, 2012", 10 pgs.
"U.S. Appl. No. 13/081,618, Supplemental Notice of Allowability dated Jun. 21, 2013", 2 pgs.
"U.S. Appl. No. 13/088,787, Final Office Action dated May 20, 2015", 11 pgs.
"U.S. Appl. No. 13/088,787, Non Final Office Action dated Sep. 11, 2014", 8 pgs.
"U.S. Appl. No. 13/088,787, Restriction Requirement dated Mar. 12, 2014", 9 pgs.
"U.S. Appl. No. 13/106,295, Non Final Office Action dated Jan. 24, 2013", 14 pgs.
"U.S. Appl. No. 13/106,295, Notice of Allowance dated Aug. 1, 2013", 9 pgs.
"U.S. Appl. No. 13/106,295, Response filed Apr. 16, 2013 to Non Final Office Action dated Jan. 24, 2013", 10 pgs.
"U.S. Appl. No. 13/106,295, Response filed Dec. 20, 2012 to Restriction Requirement dated Nov. 23, 2012", 1 pg.
"U.S. Appl. No. 13/106,295, Restriction Requirement dated Nov. 23, 2012", 5 pgs.
"U.S. Appl. No. 13/111,007, Non Final Office Action dated Mar. 25, 2013", 10 pgs.
"U.S. Appl. No. 13/111,007, Notice of Allowance dated Aug. 1, 2013", 8 pgs.
"U.S. Appl. No. 13/111,007, Notice of Allowance dated Oct. 4, 2013", 2 pgs.
"U.S. Appl. No. 13/111,007, Notice of Allowance dated Nov. 7, 2013", 2 pgs.
"U.S. Appl. No. 13/111,007, Response filed Jun. 20, 2013 to Non Final Office Action dated Mar. 25, 2013", 12 pgs.
"U.S. Appl. No. 13/111,007, Response filed Nov. 26, 2012 to Restriction Requirement dated Sep. 24, 2012", 13 pgs.
"U.S. Appl. No. 13/111,007, Restriction Requirement dated Sep. 24, 2012", 7 pgs.
"U.S. Appl. No. 13/303,546, Non Final Office Action dated Jun. 29, 2012", 12 pgs.

(56) References Cited

OTHER PUBLICATIONS

"U.S. Appl. No. 13/303,546, Notice of Allowance dated Nov. 6, 2012", 10 pgs.
"U.S. Appl. No. 13/303,546, Response filed Jun. 14, 2012 to Restriction Requirement dated May 30, 2012", 7 pgs.
"U.S. Appl. No. 13/303,546, Response filed Aug. 16, 2012 to Non Final Office Action dated Jun. 29, 2012", 11 pgs.
"U.S. Appl. No. 13/303,546, Restriction Requirement dated May 30, 2012", 6 pgs.
"U.S. Appl. No. 13/303,546, Supplemental Notice of Allowance dated Jan. 8, 2013", 4 pgs.
"U.S. Appl. No. 13/303,546, Supplemental Notice of Allowance dated Feb. 13, 2013", 4 pgs.
"U.S. Appl. No. 13/343,957, Non Final Office Action dated Feb. 20, 2014", 14 pgs.
"U.S. Appl. No. 13/343,957, Notice of Allowance dated Jul. 24, 2014", 7 pgs.
"U.S. Appl. No. 13/343,957, Response filed May 20, 2014 to Non Final Office Action dated Feb. 20, 2014", 14 pgs.
"U.S. Appl. No. 13/400,652, Corrected Notice of Allowance dated Feb. 1, 2016", 2 pgs.
"U.S. Appl. No. 13/400,652, Non Final Office Action dated Jun. 17, 2015", 7 pgs.
"U.S. Appl. No. 13/400,652, Notice of Allowance dated Jan. 11, 2016", 7 pgs.
"U.S. Appl. No. 13/400,652, Response filed Jan. 28, 2015 to Restriction Requirement dated Nov. 28, 2014", 17 pgs.
"U.S. Appl. No. 13/400,652, Response filed Apr. 13, 2015 to Restriction Requirement dated Feb. 13, 2015", 16 pgs.
"U.S. Appl. No. 13/400,652, Response filed Aug. 13, 2014 to Restriction Requirement dated Jun. 13, 2014", 19 pgs.
"U.S. Appl. No. 13/400,652, Response filed Sep. 16, 2015 to Non Final Office Action dated Jun. 17, 2015", 12 pgs.
"U.S. Appl. No. 13/400,652, Restriction Requirement dated Feb. 13, 2015", 8 pgs.
"U.S. Appl. No. 13/400,652, Restriction Requirement dated Jun. 13, 2014", 9 pgs.
"U.S. Appl. No. 13/400,652, Restriction Requirement dated Nov. 28, 2014", 7 pgs.
"U.S. Appl. No. 13/527,981, Advisory Action dated Jan. 20, 2016", 3 pgs.
"U.S. Appl. No. 13/527,981, Examiner Interview Summary dated Apr. 24, 2017", 5 pgs.
"U.S. Appl. No. 13/527,981, Final Office Action dated Feb. 5, 2015", 22 pgs.
"U.S. Appl. No. 13/527,981, Final Office Action dated Feb. 8, 2017", 17 pgs.
"U.S. Appl. No. 13/527,981, Final Office Action dated Nov. 6, 2015", 13 pgs.
"U.S. Appl. No. 13/527,981, Non Final Office Action dated Feb. 26, 2015", 10 pgs.
"U.S. Appl. No. 13/527,981, Non Final Office Action dated Jul. 28, 2016", 11 pgs.
"U.S. Appl. No. 13/527,981, Non Final Office Action dated Sep. 15, 2014", 19 pgs.
"U.S. Appl. No. 13/527,981, Response filed Jan. 6, 2016 to Final Office Action dated Nov. 6, 2015", 14 pgs.
"U.S. Appl. No. 13/527,981, Response filed May 8, 2017 to Final Office Action dated Feb. 8, 2017", 18 pgs.
"U.S. Appl. No. 13/527,981, Response filed May 27, 2014 to Restriction Requirement dated Mar. 27, 2014", 11 pgs.
"U.S. Appl. No. 13/527,981, Response filed Jul. 27, 2015 to Non-Final Office Action dated Feb. 26, 2015", 25 pgs.
"U.S. Appl. No. 13/527,981, Response Filed Oct. 28, 2016 to Non-Final Office Action dated Jul. 28, 2016", 15 pgs.
"U.S. Appl. No. 13/527,981, Restriction Requirement dared Mar. 27, 2014", 7 pgs.
"U.S. Appl. No. 13/572,895, Non Final Office Action dated Nov. 7, 2013", 5 pgs.
"U.S. Appl. No. 13/572,895, Notice of Allowance dated Apr. 29, 2014", 7 pgs.
"U.S. Appl. No. 13/572,895, Response filed Feb. 7, 2014 to Non Final Office Action dated Nov. 7, 2013", 13 pgs.
"U.S. Appl. No. 13/674,531, Final Office Action dated Apr. 29, 2015", 8 pgs.
"U.S. Appl. No. 13/674,531, Response filed Jul. 29, 2015 to Final Office Action dated Apr. 29, 2015", 12 pgs.
"U.S. Appl. No. 13/674,531, Restriction Requirement dated Sep. 24, 2014", 7 pgs.
"U.S. Appl. No. 13/713,710, Notice of Allowance dated Sep. 15, 2015", 10 pgs.
"U.S. Appl. No. 13/713,710, Response filed Aug. 25, 2015 to Restriction Requirement dated Jul. 2, 2015", 7 pgs.
"U.S. Appl. No. 13/713,710, Restriction Requirement dated Jul. 2, 2015", 6 pgs.
"U.S. Appl. No. 13/744,022, Advisory Action dated Oct. 27, 2014", 3 pgs.
"U.S. Appl. No. 13/744,022, Final Office Action dated Jul. 14, 2014", 9 pgs.
"U.S. Appl. No. 13/744,022, Non Final Office Action dated Jan. 30, 2014", 20 pgs.
"U.S. Appl. No. 13/744,022, Notice of Allowance dated Nov. 28, 2014", 9 pgs.
"U.S. Appl. No. 13/744,022, Response filed Apr. 25, 2014 to Non Final Office Action dated Jan. 30, 2014", 16 pgs.
"U.S. Appl. No. 13/744,022, Response filed Oct. 8, 2014 to Final Office Action dated Jul. 14, 2014", 15 pgs.
"U.S. Appl. No. 13/766,419, Advisory Action dated May 18, 2015", 2 pgs.
"U.S. Appl. No. 13/766,419, Final Office Action dated Jan. 13, 2015", 16 pgs.
"U.S. Appl. No. 13/766,419, Non Final Office Action dated Sep. 5, 2014", 14 pgs.
"U.S. Appl. No. 13/766,419, Response filed May 12, 2015 to Final Office Action dated Jan. 13, 2015", 13 pgs.
"U.S. Appl. No. 13/766,419, Response filed Dec. 5, 2014 to Non Final Office Action dated Sep. 5, 2014", 12 pgs.
"U.S. Appl. No. 13/800,334, Examiner Interview Summary dated Jan. 29, 2015", 4 pgs.
"U.S. Appl. No. 13/800,334, Final Office Action dated Feb. 12, 2015", 11 pgs.
"U.S. Appl. No. 13/800,334, Non Final Office Action dated Sep. 24, 2015", 14 pgs.
"U.S. Appl. No. 13/800,334, Non Final Office Action dated Oct. 22, 2014", 11 pgs.
"U.S. Appl. No. 13/800,334, Non Final Office Action dated Dec. 15, 2016", 26 pgs.
"U.S. Appl. No. 13/800,334, Response filed Jan. 21, 2015 to Non Final Office Action dated Oct. 22, 2014", 12 pgs.
"U.S. Appl. No. 13/800,334, Response filed Mar. 15, 2017 to Non Final Office Action dated Dec. 15, 2016", 16 pgs.
"U.S. Appl. No. 13/800,334, Response filed Jun. 24, 2016 to Final Office Action dated Apr. 7, 2016", 19 pgs.
"U.S. Appl. No. 13/800,334, Response filed Jul. 10, 2015 to Final Office Action dated Feb. 12, 2015", 8 pgs.
"U.S. Appl. No. 13/800,334, Response filed Dec. 16, 2015 to Non Final Office Action dated Sep. 24, 2015", 16 pgs.
"U.S. Appl. No. 13/923,827, Advisory Action dated Oct. 9, 2014", 3 pgs.
"U.S. Appl. No. 13/923,827, Examiner Interview Summary dated Sep. 29, 2014", 3 pgs.
"U.S. Appl. No. 13/923,827, Final Office Action dated Jul. 28, 2014", 11 pgs.
"U.S. Appl. No. 13/923,827, Non Final Office Action dated Apr. 10, 2014", 9 pgs.
"U.S. Appl. No. 13/923,827, Notice of Allowance dated Oct. 29, 2014", 11 pgs.
"U.S. Appl. No. 13/923,827, Response filed Jul. 10, 2014 to Non Final Office Action dated Apr. 10, 2014", 13 pgs.
"U.S. Appl. No. 13/923,827, Response filed Sep. 29, 2014 to Final Office Action dated Jul. 28, 2014", 11 pgs.

(56) References Cited

OTHER PUBLICATIONS

"U.S. Appl. No. 13/923,827, Supplemental Notice of Allowance dated Feb. 11, 2015", 2 pgs.
"U.S. Appl. No. 13/923,827, Supplemental Notice of Allowance dated Dec. 19, 2014", 3 pgs.
"U.S. Appl. No. 14/027,340, Advisory Action dated Sep. 17, 2015", 3 pgs.
"U.S. Appl. No. 14/027,340, Final Office Action dated Jul. 8, 2015", 10 pgs.
"U.S. Appl. No. 14/027,340, Non Final Office Action dated Jan. 22, 2015", 11 pgs.
"U.S. Appl. No. 14/027,340, Non Final Office Action dated Dec. 9, 2015", 10 pgs.
"U.S. Appl. No. 14/027,340, Notice of Allowance dated May 12, 2016", 7 pgs.
"U.S. Appl. No. 14/027,340, Response filed Feb. 19, 2016 to Non Final Office Action dated Dec. 9, 2015", 13 pgs.
"U.S. Appl. No. 14/027,340, Response filed May 21, 20 to Non Final Office Action dated Jan. 22, 2015", 14 pgs.
"U.S. Appl. No. 14/027,340, Response filed Sep. 9, 2015 to Final Office Action dated Jul. 8, 2015", 15 pgs.
"U.S. Appl. No. 14/064,970, Advisory Action dated Jan. 4, 2016", 3 pgs.
"U.S. Appl. No. 14/064,970, Final Office Action dated Oct. 19, 2015", 10 pgs.
"U.S. Appl. No. 14/064,970, Non Final Office Action dated Mar. 12, 2015", 11 pgs.
"U.S. Appl. No. 14/064,970, Non Final Office Action dated Jul. 26, 2016", 12 pgs.
"U.S. Appl. No. 14/064,970, Notice of Allowability dated Feb. 10, 2017", 2 pgs.
"U.S. Appl. No. 14/064,970, Notice of Allowability dated Feb. 17, 2017", 2 pgs.
"U.S. Appl. No. 14/064,970, Notice of Allowance dated Jan. 27, 2017", 10 pgs.
"U.S. Appl. No. 14/064,970, Response filed Jul. 8, 2015 to Non Final Office Action dated Mar. 12, 2015", 8 pgs.
"U.S. Appl. No. 14/064,970, Response filed Oct. 26, 2016 to Non Final Office Action dated Jul. 26, 2016", 14 pgs.
"U.S. Appl. No. 14/064,970, Response filed Dec. 9, 2014 to Restriction Requirement dated Oct. 9, 2014", 11 pgs.
"U.S. Appl. No. 14/064,970, Response filed Dec. 15, 2015 to Final Office Action dated Oct. 19, 2015", 11 pgs.
"U.S. Appl. No. 14/064,970, Restriction Requirement dated Oct. 9, 2014", 9 pgs.
"U.S. Appl. No. 14/086,447, Notice of Allowance dated Aug. 12, 2016", 9 pgs.
"U.S. Appl. No. 14/086,447, Preliminary Amendment filed Jul. 29, 2016", 4 pgs.
"U.S. Appl. No. 14/086,447, Response filed May 4, 2016 to Restriction Requirement dated Apr. 6, 2016", 7 pgs.
"U.S. Appl. No. 14/086,447, Restriction Requirement dated Apr. 6, 2016", 7 pgs.
"U.S. Appl. No. 14/100,134 Response Filed Apr. 14, 2016 to Restriction Requirement dated Feb. 24, 2016", 7 pgs.
"U.S. Appl. No. 14/100,134, Notice of Allowance dated Jun. 16, 2016", 14 pgs.
"U.S. Appl. No. 14/100,134, Restriction Requirement dated Feb. 24, 2016", 5 pgs.
"U.S. Appl. No. 14/105,669, Non Final Office Action dated Jan. 11, 2016", 11 pgs.
"U.S. Appl. No. 14/105,669, Non Final Office Action dated Aug. 11, 2016", 5 pgs.
"U.S. Appl. No. 14/105,669, Notice of Allowance dated Jan. 26, 2017", 7 pgs.
"U.S. Appl. No. 14/105,669, Response filed Oct. 13, 2015 to Restriction Requirement dated Sep. 8, 2015", 7 pgs.
"U.S. Appl. No. 14/105,669, Response filed Oct. 31, 2016 to Non Final Office Action dated Aug. 11, 2016", 8 pgs.
"U.S. Appl. No. 14/105,669, Restriction Requirement dated Sep. 8, 2015", 6 pgs.
"U.S. Appl. No. 14/106,669, Response filed Apr. 11, 2016 to Non Final Office Action dated Jan. 11, 2016", 11 pgs.
"U.S. Appl. No. 14/107,316, Corrected Notice of dated Jul. 11, 2016", 2 pgs.
"U.S. Appl. No. 14/107,316, Examiner Interview Summary dated Jun. 10, 2016", 3 pgs.
"U.S. Appl. No. 14/107,316, Non Final Office Action dated Mar. 24, 2016", 16 pgs.
"U.S. Appl. No. 14/107,316, Notice of Allowance dated Jun. 28, 2016", 11 pgs.
"U.S. Appl. No. 14/107,316, Notice of Non-Compliant Amendment dated Dec. 30, 2015", 3 pgs.
"U.S. Appl. No. 14/107,316, Response filed Jan. 18, 2016 to Notice of Non-Compliant Amendment dated Dec. 30, 2015", 8 pgs.
"U.S. Appl. No. 14/107,316, Response filed Jun. 13, 2016 to Non Final Office Action dated Mar. 24, 2016", 13 pgs.
"U.S. Appl. No. 14/107,316, Response filed Dec. 16, 2015 to Restriction Requirement dated Oct. 29, 2015", 8 pgs.
"U.S. Appl. No. 14/107,316, Restriction Requirement mailed Oct. 29, 2015", 8 pgs.
"U.S. Appl. No. 14/159,071, Final Office Action dated May 14, 2015", 7 pgs.
"U.S. Appl. No. 14/159,071, Non Final Office Action dated Dec. 8, 2014", 14 pgs.
"U.S. Appl. No. 14/327,234, Notice of Allowance dated Jun. 22, 2017", 12 pgs.
"U.S. Appl. No. 14/327,234, Response filed May 17, 2017 to Restriction Requriement dated Apr. 6, 2017", 8 pgs.
"U.S. Appl. No. 14/327,234, Restriction Requirement dated Apr. 6, 2017", 7 pgs.
"U.S. Appl. No. 14/483,214, Examiner Interview Summary dated Apr. 12, 2017", 3 pgs.
"U.S. Appl. No. 14/483,214, Final Office Action dated Dec. 16, 2015", 9 pgs.
"U.S. Appl. No. 14/483,214, Non Final Office Action dated May 2, 2017", 10 pgs.
"U.S. Appl. No. 14/483,214, Non Final Office Action dated Jun. 5, 2015", 8 pgs.
"U.S. Appl. No. 14/483,214, Non Final Office Action dated Oct. 6, 2016", 12 pgs.
"U.S. Appl. No. 14/483,214, Response filed Jan. 6, 2017 to Non Final Office Action dated Oct. 6, 2016", 16 pgs.
"U.S. Appl. No. 14/483,214, Response filed Mar. 14, 2016 to Final Office Action dated Dec. 16, 2015", 15 pgs.
"U.S. Appl. No. 14/483,214, Response filed May 15, 2015 to Restriction Requirement dated Mar. 25, 2015", 2 pgs.
"U.S. Appl. No. 14/483,214, Response filed Sep. 2, 2015 to Non Final Office Action dated Jun. 5, 2015", 13 pgs.
"U.S. Appl. No. 14/483,214, Restriction Requirement dated Mar. 25, 2015", 6 pgs.
"U.S. Appl. No. 14/658,429, Final Office Action dated Aug. 29, 2016", 9 pgs.
"U.S. Appl. No. 14/658,429, Non Final Office Action dated Feb. 23, 2017", 6 pgs.
"U.S. Appl. No. 14/658,429, Non Final Office Action dated Mar. 24, 2016", 7 pgs.
"U.S. Appl. No. 14/658,429, Response filed Nov. 21, 2016 to Final Office Action dated Aug. 29, 2016", 14 pgs.
"U.S. Appl. No. 14/658,429, Response Filed Jun. 20, 2016 to Non-Final Office Action dated Mar. 24, 2016", 12 pgs.
"U.S. Appl. No. 14/684,936, Corrected Notice of Allowance dated Sep. 22, 2016", 4 pgs.
"U.S. Appl. No. 14/684,936, Non Final Office Action dated Mar. 22, 2016", 7 pgs.
"U.S. Appl. No. 14/684,936, Notice of Allowance dated Aug. 30, 2016", 6 pgs.
"U.S. Appl. No. 14/684,936, Response filed Jun. 9, 2016 to Non Final Office Action dated Mar. 22, 2016", 8 pgs.
"U.S. Appl. No. 14/798,809, Response filed Apr. 3, 2017 to Restriction Requirement dated Jan. 4, 2017", 8 pgs.

(56) References Cited

OTHER PUBLICATIONS

"U.S. Appl. No. 14/798,809, Restriction Requirement dated Jan. 4, 2017", 10 pgs.
"U.S. Appl. No. 14/812,583, Non Final Office Action dated May 9, 2017", 14 pgs.
"U.S. Appl. No. 14/812,583, Preliminary Amendment filed Jul. 29, 2015", 6 pgs.
"U.S. Appl. No. 14/812,583, Response filed Mar. 16, 2017 to Restriction Requirement dated Jan. 23, 2017", 6 pgs.
"U.S. Appl. No. 14/812,583, Restriction Requirement dated Jan. 23, 2017", 8 pgs.
"U.S. Appl. No. 14/865,762, Preliminary Amendment filed Oct. 14, 2015", 6 pgs.
"U.S. Appl. No. 14/865,762, Restriction Requirement dated Apr. 13, 2017", 6 pgs.
"U.S. Appl. No. 14/973,057, Final Office Action dated Feb. 13, 2017", 7 pgs.
"U.S. Appl. No. 14/973,057, Non Final Office Action dated Oct. 18, 2016", 6 pgs.
"U.S. Appl. No. 14/973,057, Notice of Allowance dated Apr. 27, 2017", 7 pgs.
"U.S. Appl. No. 14/973,057, Preliminary Amendment filed Dec. 18, 2015", 7 pgs.
"U.S. Appl. No. 14/973,057, Response filed Jan. 18, 2017 to Non Final Office Action dated Oct. 18, 2016", 8 pgs.
"U.S. Appl. No. 14/973,057, Response filed Apr. 5, 2017 to Final Office Action dated Feb. 13, 2017", 9 pgs.
"U.S. Appl. No. 14/973,057, Response filed Sep. 21, 2016 to Restriction Requirement dated Jul. 29, 2016", 5 pgs.
"U.S. Appl. No. 14/973,057, Restriction Requirement dated Jul. 29, 2016", 8 pgs.
"U.S. Appl. No. 15/008,528, Preliminary Amendment dated Jan. 29, 2016", 8 pgs.
"U.S. Appl. No. 15/093,384, Preliminary Amendment filed Apr. 28, 2016", 5 pgs.
"U.S. Appl. No. 15/130,414, Preliminary Amendment filed Mar. 9, 2017", 6 pgs.
"U.S. Appl. No. 15/224,741, Preliminary Amendment filed Sep. 12, 2016", 8 pgs.
"U.S. Appl. No. 15/267,714, Non Final Office Action dated May 10, 2017", 23 pgs.
"U.S. Appl. No. 15/267,714, Preliminary Amendment filed Oct. 6, 2016", 7 pgs.
"U.S. Appl. No. 15/267,714, Response filed Feb. 28, 2017 to Restriction Requirement dated Jan. 5, 2017", 8 pgs.
"U.S. Appl. No. 15/267,714, Restriction Requirement dated Jan. 5, 2017", 5 pgs.
"U.S. Appl. No. 15/352,721, Corrected Notice of Allowance dated Apr. 27, 2017", 2 pgs.
"U.S. Appl. No. 15/352,721, Notice of Allowance dated Mar. 10, 2017", 11 pgs.
"U.S. Appl. No. 15/352,721, Preliminary Amendment filed Feb. 3, 2017", 6 pgs.
"U.S. Appl. No. 12/025,414, Applicant's Summary of Examiner Interview filed Apr. 9, 2012", 4 pgs.
"U.S. Appl. No. 12/025,414, Final Office Action dated Mar. 14, 2012", 6 pgs.
"U.S. Appl. No. 12/025,414, Final Office Action dated May 1, 2012", 10 pgs.
"U.S. Appl. No. 12/025,414, Non Final Office Action dated Oct. 25, 2011", 10 pgs.
"U.S. Appl. No. 12/025,414, Notice of Allowance dated Jun. 13, 2012", 7 pgs.
"U.S. Appl. No. 12/025,414, Response filed Apr. 9, 2012 to Final Office Action dated Mar. 14, 2012", 15 pgs.
"U.S. Appl. No. 12/025,414, Response filed May 21, 2012 to Final Office Action dated May 1, 2012", 6 pgs.
"U.S. Appl. No. 12/025,414, Response filed Jul. 26, 2011 to Restriction Requirement dated Jul. 19, 2011", 8 pgs.
"U.S. Appl. No. 12/025,414, Response filed Dec. 22, 2011 to Non Final Office Action dated Oct. 25, 2011", 13 pgs.
"U.S. Appl. No. 12/025,414, Restriction Requirement dated Jul. 19, 2011", 5 pgs.
"U.S. Appl. No. 12/483,807, Final Office Action dated Nov. 4, 2011", 20 pgs.
"U.S. Appl. No. 12/872,663, Response filed Sep. 13, 2012 to Non Final Office Action dated Jun. 20, 2012", 9 pgs.
"U.S. Appl. No. 13/800,334, Final Office Action dated Apr. 6, 2016", 19 pgs.
"Ascent Total Knee System", Biomet, Inc., (Oct. 31, 1999), 16 pgs.
"Australian Application Serial No. 2013222609, First Examiner Report dated Feb. 16, 2015", 5 pgs.
"Australian Application Serial No. 2013222609, Response filed Sep. 17, 2015 to First Examiner Report dated Feb. 16, 2015", 17 pgs.
"Comprehensive® Reverse Shoulder System", Biomet Orthopedics brochure, (2009), 8 pgs.
"Comprehensive® Reverse Shoulder System Surgical Technique", Biomet Orthopedics, (2009-2012), 48 pgs.
"Comprehensive® Reverse Shoulder System Technical Design Features", Biomet Orthopedics, (2009), 3 pgs.
"Comprehensive® Shoulder System Surgical Technique", Biomet Orthopedics brochure, (2007), 1-53.
"Comprehensive® Total Shoulder System", Biomet Orthopedics brochure, (2011), 4 pgs.
"Customized Patient Instruments, Patient specific instruments for patient specific needs", DePuy Orthopaedics, Inc., (2008), 14 pgs.
"Customized Patient Instruments, Primary Cruciate Retaining Surgical Technique for use with the Sigma® Knee System Utilizing Specialist® 2 Instrumentation", DePuy Orthopaedics, Inc., (2008), 1-23.
"Discovery® Elbow System", Biomet Orthopedics, Inc., (Nov. 30, 2007), 3 pgs.
"Discovery® Elbow System Surgical Technique", Biomet Orthopedics, Inc., (Dec. 31, 2008), 1-25.
"DURALOC® Cementless Acetabular Reconstruction", Surgical Technique brochure, DePuy International Ltd., (2007), 10 pgs.
"European Application Serial 13710642.3, Communication Pursuant to Article 94(3) EPC dated Nov. 6, 2015", 3 pgs.
"European Application Serial 13710642.3, Intention to grant dated Jun. 17, 2016", 7 pgs.
"European Application Serial 13710642.3, Response filed Mar. 16, 2016 to Communication Pursuant to Article 94(3) EPC dated Nov. 6, 2015", 8 pgs.
"European Application Serial No. 07809326.7, Examination Notification Art. 94(3) dated Jan. 22, 2015", 6 pgs.
"European Application Serial No. 07809326.7, Extended European Search Report dated Nov. 15, 2011", 6 pgs.
"European Application Serial No. 07809326.7, Office Action dated Jan. 28, 2009", 2 pgs.
"European Application Serial No. 07809326.7, Office Action dated Dec. 2, 2011", 1 pg.
"European Application Serial No. 07809326.7, Response filed Jun. 6, 2012 to Extended European Search Report dated Nov. 15, 2011", 6 pgs.
"European Application Serial No. 07809326.7, Response filed Jul. 31, 2015 to Examination Notification Art. 94(3) dated Jan. 22, 2015", 10 pgs.
"European Application Serial No. 09731923.0, Communication Pursuant to Article 94(3) EPC dated Nov. 29, 2016", 5 pgs.
"European Application Serial No. 09731923.0, Examination Notification Art. 94(3) dated Feb. 10, 2015", 7 pgs.
"European Application Serial No. 09731923.0, Office Action dated Feb. 3, 2011", 2 pgs.
"European Application Serial No. 09731923.0, Response filed Apr. 10, 2017 to Communication Pursuant to Article 94(3) EPC dated Nov. 29, 2016", 18 pgs.
"European Application Serial No. 09731923.0, Response filed Aug. 20, 2015 to Examination Notification Art. 94(3) dated Feb. 10, 2015", 11 pgs.
"European Application Serial No. 09732174.9, Communication Pursuant to Article 94(3) EPC dated Mar. 3, 2016", 4 pgs.

(56) References Cited

OTHER PUBLICATIONS

"European Application Serial No. 09732174.9, Communication Pursuant to Article 94(3) EPC dated Oct. 17, 2016", 4 pgs.
"European Application Serial No. 09732174.9, Examination Notification Art. 94(3) dated Mar. 7, 2014", 5 pgs.
"European Application Serial No. 09732174.9, Office Action dated Feb. 3, 2011", 2 pgs.
"European Application Serial No. 09732174.9, Response filed Feb. 22, 2017 to Communication Pursuant to Article 94(3) EPC dated Oct. 17, 2016", 6 pgs.
"European Application Serial No. 09732174.9, Response filed Jul. 13, 2016 to Communication Pursuant to Article 94(3) EPC dated Mar. 3, 2016", 12 pgs.
"European Application Serial No. 09732174.9, Response filed Jul. 14, 2014 to Examination Notification Art. 94(3) dated Mar. 7, 2014", 6 pgs.
"European Application Serial No. 09792468.2, Communication Pursuant to Article 94(3) EPC dated Jun. 7, 2016", 4 pgs.
"European Application Serial No. 09792468.2, Examination Notification Art. 94(3) dated Jan. 29, 2015", 5 pgs.
"European Application Serial No. 09792468.2, Office Action dated Jul. 8, 2011", 2 pgs.
"European Application Serial No. 09792468.2, Response filed Jan. 9, 2012 to Office Action dated Jul. 8, 2011", 11 pgs.
"European Application Serial No. 09792468.2, Response filed May 29, 2015 to Examination Notification Art. 94(3) dated Jan. 29, 2015", 8 pgs.
"European Application Serial No. 09792468.2, Response filed Sep. 28, 2016 to Communication Pursuant to Article 94(3) EPC dated Jun. 7, 2016", 21 pgs.
"European Application Serial No. 10705064.3, Communication Pursuant to Article 94(3) EPC dated Dec. 8, 2015", 4 pgs.
"European Application Serial No. 10705064.3, Examination Notification Art. 94(3) dated Feb. 4, 2015", 6 pgs.
"European Application Serial No. 10705064.3, Office Action dated Nov. 22, 2011", 2 pgs.
"European Application Serial No. 10705064.3, Response filed Apr. 18, 2016 to Communication Pursuant to Article 94(3) EPC dated Dec. 8, 2015", 8 pgs.
"European Application Serial No. 10705064.3, Response filed Aug. 14, 2015 to Examination Notification Art. 94(3) dated Feb. 4, 2015", 9 pgs.
"European Application Serial No. 10705951.1, Communication Pursuant to Article 94(3) EPC dated Jan. 22, 2013", 7 pgs.
"European Application Serial No. 10705951.1, Office Action dated Oct. 7, 2011", 2 pgs.
"European Application Serial No. 10705951.1, Response filed May 23, 2013 to Communication Pursuant to Article 94(3) EPC dated Jan. 22, 2013", 8 pgs.
"European Application Serial No. 12156937.0, Decision of Grant dated May 4, 2015", 2 pgs.
"European Application Serial No. 12156937.0, Examination Notification Art. 94(3) dated Dec. 11, 2013", 5 pgs.
"European Application Serial No. 12156937.0, Extended European Search Report dated Sep. 6, 2012", 9 pgs.
"European Application Serial No. 12156937.0, Response filed Apr. 16, 2013 to Extended European Search Report dated Sep. 6, 2012", 9 pgs.
"European Application Serial No. 12156937.0, Response filed Apr. 17, 2014 to Examination Notification Art. 94(3) dated Dec. 11, 2013", 15 pgs.
"European Application Serial No. 12724475.4, Communication Pursuant to Article 94(3) EPC dated Aug. 31, 2016", 5 pgs.
"European Application Serial No. 12724475.4, Examination Notification Art. 94(3) dated Nov. 24, 2014", 7 pgs.
"European Application Serial No. 12724475.4, Office Action dated Jan. 21, 2014", 2 pgs.
"European Application Serial No. 12724475.4, Response filed Jan. 10, 2017 to Communication Pursuant to Article 94(3) EPC dated Aug. 31, 2016", 17 pgs.
"European Application Serial No. 12724475.4, Response filed Apr. 15, 2015 to Examination Notification Art. 94(3) dated Nov. 24, 2014", 9 pgs.
"European Application Serial No. 13710642.3, Amendment dated Sep. 1, 2014", 7 pgs.
"European Application Serial No. 13710642.3, Office Action dated Oct. 10, 2014", 2 pgs.
"European Application Serial No. 16179349.2, Extended European Search Report dated Mar. 22, 2017", 9 pgs.
"Great Britain Application Serial No. 1116054.6, Search Report dated Dec. 21, 2011", 4 pgs.
"Hand Instruments", High Performance, Precision Series brochure by Arthrotek, copyright, (2000), 3 pgs.
"Hipsextant Instructions of Use", Surgical Planning Associates, Inc., (2011), 19 pgs.
"International Application Serial No. PCT/EP2010/061630, International Search Report dated Nov. 30, 2010", 3 pgs.
"International Application Serial No. PCT/GB2007/003737, International Preliminary Report on Patentability dated Apr. 7, 2009", 8 pgs.
"International Application Serial No. PCT/GB2007/003737, Written Opinion dated Jan. 25, 2008", 7 pgs.
"International Application Serial No. PCT/US2007/013223, International Preliminary Report on Patentability dated Dec. 24, 2008", 5 pgs.
"International Application Serial No. PCT/US2007/013223, International Search Report dated Nov. 26, 2007", 3 pgs.
"International Application Serial No. PCT/US2007/013223, Written Opinion dated Nov. 26, 2007", 4 pgs.
"International Application Serial No. PCT/US2009/039507, International Preliminary Report on Patentability dated Oct. 28, 2010", 9 pgs.
"International Application Serial No. PCT/US2009/039507, International Search Report dated Jul. 14, 2009", 6 pgs.
"International Application Serial No. PCT/US2009/039507, Written Opinion dated Jul. 14, 2009", 7 pgs.
"International Application Serial No. PCT/US2009/039578, International Preliminary Report on Patentability dated Oct. 28, 2010", 9 pgs.
"International Application Serial No. PCT/US2009/039578, International Search Report dated Jul. 31, 2009", 6 pgs.
"International Application Serial No. PCT/US2009/039578, Written Opinion dated Jul. 31, 2009", 7 pgs.
"International Application Serial No. PCT/US2009/056670, International Preliminary Report on Patentability dated Mar. 31, 2011", 12 pgs.
"International Application Serial No. PCT/US2009/056670, International Search Report dated Mar. 2, 2010", 7 pgs.
"International Application Serial No. PCT/US2009/056670, Invitation to Pay Additional Fees and Partial Search Report dated Nov. 26, 2009".
"International Application Serial No. PCT/US2009/056670, Written Opinion dated Mar. 2, 2010", 10 pgs.
"International Application Serial No. PCT/US2009/061434, International Preliminary Report on Patentability dated May 5, 2011", 6 pgs.
"International Application Serial No. PCT/US2009/061434, International Search Report dated Feb. 2, 2010", 4 pgs.
"International Application Serial No. PCT/US2009/061434, Written Opinion dated Feb. 2, 2010", 4 pgs.
"International Application Serial No. PCT/US2010/024073, International Preliminary Report on Patentability dated Aug. 25, 2011", 8 pgs.
"International Application Serial No. PCT/US2010/024073, International Search Report dated Jun. 4, 2010", 4 pgs.
"International Application Serial No. PCT/US2010/024073, Written Opinion dated Jun. 4, 2010", 6 pgs.
"International Application Serial No. PCT/US2010/024579, International Preliminary Report on Patentability dated Sep. 1, 2011", 7 pgs.
"International Application Serial No. PCT/US2010/024579, International Search Report dated Apr. 22, 2010", 3 pgs.

(56) References Cited

OTHER PUBLICATIONS

"International Application Serial No. PCT/US2010/024579, Written Opinion dated Apr. 22, 2010", 5 pgs.
"International Application Serial No. PCT/US2010/024584, International Preliminary Report on Patentability dated Sep. 1, 2011", 8 pgs.
"International Application Serial No. PCT/US2010/024584, International Search Report dated Aug. 19, 2010", 6 pgs.
"International Application Serial No. PCT/US2010/024584, Written Opinion dated Aug. 19, 2010", 6 pgs.
"International Application Serial No. PCT/US2010/038177, International Preliminary Report on Patentability dated Dec. 22, 2011", 10 pgs.
"International Application Serial No. PCT/US2010/038177, International Search Report dated Aug. 24, 2010", 4 pgs.
"International Application Serial No. PCT/US2010/038177, Written Opinion dated Aug. 24, 2010", 8 pgs.
"International Application Serial No. PCT/US2010/038845, International Preliminary Report on Patentability dated Jan. 5, 2012", 9 pgs.
"International Application Serial No. PCT/US2010/038845, International Search Report dated Oct. 5, 2010", 4 pgs.
"International Application Serial No. PCT/US2010/038845, Written Opinion dated Oct. 5, 2010", 7 pgs.
"International Application Serial No. PCT/US2010/050701, International Preliminary Report on Patentability dated Apr. 12, 2012", 10 pgs.
"International Application Serial No. PCT/US2010/050701, International Search Report dated Dec. 7, 2010", 6 pgs.
"International Application Serial No. PCT/US2010/050701, Written Opinion dated Dec. 7, 2010", 8 pgs.
"International Application Serial No. PCT/US2011/026333, International Preliminary Report on Patentability dated Sep. 7, 2012", 10 pgs.
"International Application Serial No. PCT/US2011/026333, International Search Report dated Aug. 9, 2011", 6 pgs.
"International Application Serial No. PCT/US2011/026333, Invitation to Pay Additional Fees dated May 3, 2011".
"International Application Serial No. PCT/US2011/026333, Written Opinion dated Aug. 9, 2011", 8 pgs.
"International Application Serial No. PCT/US2011/026412, International Preliminary Report on Patentability dated Sep. 30, 2012", 8 pgs.
"International Application Serial No. PCT/US2011/026412, International Search Report dated May 9, 2011", 5 pgs.
"International Application Serial No. PCT/US2011/026412, Written Opinion dated May 9, 2011", 6 pgs.
"International Application Serial No. PCT/US2011/057300, International Preliminary Report on Patentability dated May 16, 2013", 11 pgs.
"International Application Serial No. PCT/US2011/057300, International Search Report dated Mar. 5, 2012", 7 pgs.
"International Application Serial No. PCT/US2011/057300, Written Opinion dated Mar. 5, 2012", 9 pgs.
"International Application Serial No. PCT/US2012/026356, International Preliminary Report on Patentability dated Sep. 6, 2013", 8 pgs.
"International Application Serial No. PCT/US2012/026356, International Search Report dated May 8, 2012", 5 pgs.
"International Application Serial No. PCT/US2012/026356, Written Opinion dated May 8, 2012", 6 pgs.
"International Application Serial No. PCT/US2012/038351, International Search Report dated Jul. 6, 2012", 6 pgs.
"International Application Serial No. PCT/US2012/038351, International Preliminary Report on Patentability dated Nov. 28, 2013", 9 pgs.
"International Application Serial No. PCT/US2012/038351, Written Opinion dated Jul. 6, 2012", 8 pgs.
"International Application Serial No. PCT/US2012/041893, International Search Report dated Oct. 23, 2012", 5 pgs.
"International Application Serial No. PCT/US2012/042081, International Preliminary Report on Patentability dated Jan. 3, 2014", 7 pgs.
"International Application Serial No. PCT/US2012/042081, Written Opinion dated Sep. 5, 2012", 6 pgs.
"International Application Serial No. PCT/US2012/052853, International Preliminary Report on Patentability dated Mar. 13, 2014", 14 pgs.
"International Application Serial No. PCT/US2012/052853, International Search Report dated Nov. 15, 2012", 6 pgs.
"International Application Serial No. PCT/US2012/052853, Written Opinion dated Nov. 15, 2012", 12 pgs.
"International Application Serial No. PCT/US2012/059189, International Preliminary Report on Patentability dated Apr. 24, 2014", 10 pgs.
"International Application Serial No. PCT/US2012/059189, International Search Report dated Dec. 18, 2012", 6 pgs.
"International Application Serial No. PCT/US2012/059189, Written Opinion dated Dec. 18, 2012", 9 pgs.
"International Application Serial No. PCT/US2012/060842, International Preliminary Report on Patentability dated May 8, 2014", 7 pgs.
"International Application Serial No. PCT/US2012/060842, International Search Report dated Feb. 6, 2013", 4 pgs.
"International Application Serial No. PCT/US2012/060842, Written Opinion dated Feb. 6, 2013", 5 pgs.
"International Application Serial No. PCT/US2012/060848, International Preliminary Report on Patentability dated May 8, 2014", 11 pgs.
"International Application Serial No. PCT/US2012/060848, Invitation to Pay Additional Fees dated Feb. 6, 2013".
"International Application Serial No. PCT/US2012/060848, Written Opinion dated Apr. 12, 2013", 9 pgs.
"International Application Serial No. PCT/US2012/060853, International Preliminary Report on Patentability dated May 8, 2014", 11 pgs.
"International Application Serial No. PCT/US2012/060853, Invitation to Pay Additional Fees dated Feb. 7, 2013", 4 pgs.
"International Application Serial No. PCT/US2012/060853, Written Opinion dated Apr. 9, 2013", 9 pgs.
"International Application Serial No. PCT/US2012/060854, International Preliminary Report on Patentability dated May 8, 2014", 8 pgs.
"International Application Serial No. PCT/US2012/060854, International Search Report dated Feb. 6, 2013", 4 pgs.
"International Application Serial No. PCT/US2012/060854, Written Opinion dated Feb. 6, 2013", 6 pgs.
"International Application Serial No. PCT/US2013/026875, International Preliminary Report on Patentability dated Sep. 4, 2014", 9 pgs.
"International Application Serial No. PCT/US2013/026875, International Search Report dated Jun. 7, 2013", 5 pgs.
"International Application Serial No. PCT/US2013/026875, Written Opinion dated Jun. 7, 2013", 8 pgs.
"International Application Serial No. PCT/US2013/057097, International Preliminary Report on Patentability dated Mar. 12, 2015", 10 pgs.
"International Application Serial No. PCT/US2013/057097, International Search Report dated Oct. 14, 2013", 6 pgs.
"International Application Serial No. PCT/US2013/057097, Written Opinion dated Oct. 14, 2013", 9 pgs.
"International Application Serial No. PCT/US2013/067505, International Preliminary Report on Patentability dated May 14, 2015", 13 pgs.
"International Application Serial No. PCT/US2013/067505, International Search Report dated Apr. 14, 2014", 5 pgs.
"International Application Serial No. PCT/US2013/067505, Invitation to Pay Additional Fees dated Feb. 6, 2014", 6 pgs.
"International Application Serial No. PCT/US2013/067505, Written Opinion daated Apr. 14, 2014", 11 pgs.
"International Application Serial No. PCT/US2013/074288, International Preliminary Report on Patentability dated Jun. 25, 2015", 13 pgs.

(56) References Cited

OTHER PUBLICATIONS

"International Application Serial No. PCT/US2013/074288, International Search Report dated May 23, 2014", 7 pgs.
"International Application Serial No. PCT/US2013/074288, Written Opinion dated May 23, 2014", 11 pgs.
"International Application Serial No. PCT/US2014/022000, International Search Report dated Jun. 24, 2014", 3 pgs.
"International Application Serial No. PCT/US2014/022000, Written Opinion dated Jun. 24, 2014", 5 pgs.
"International Application Serial No. PCT/US2014/023655, International Search Report dated Jul. 10, 2014", 4 pgs.
"International Application Serial No. PCT/US2014/023655, Written Opinion dated Jul. 10, 2014", 6 pgs.
"International Application Serial No. PCT/US2014/068131, International Search Report dated May 8, 2015", 5 pgs.
"International Application Serial No. PCT/US2014/068131, Written Opinion dated May 8, 2015", 9 pgs.
"International Application Serial No. PCT/US2015/039561, International Preliminary Report on Patentability dated Jan. 19, 2017", 8 pgs.
"International Application Serial No. PCT/US2015/039561, International Search Report dated Sep. 14, 2015", 5 pgs.
"International Application Serial No. PCT/US2015/039561, Written Opinion dated Sep. 14, 2015", 6 pgs.
"Is Subchondroplasty® Right for Me?", [Online] retrieved from the internet: <http://www.subchondroplast}'..com/about subchondroplast}'./ is subchondroplasty right for >, (Jul. 1, 2013), 1 pg.
"Japanese Application Serial No. 2011-505080, Appeal Decision dated Jun. 24, 2015", (W/ English Translation), 3 pgs.
"Japanese Application Serial No. 2011-505080, Decision of Refusal dated Nov. 27, 2013", (W/ English Translation), 4 pgs.
"Japanese Application Serial No. 2011-505080, Office Action dated Feb. 25, 2015", (W/ English Translation), 2 pgs.
"Japanese Application Serial No. 2011-505080, Office Action dated Apr. 3, 2013", (W/ English Translation), 6 pgs.
"Japanese Application Serial No. 2011-505080, Response filed Mar. 27, 2014 to Decision of Refusal dated Nov. 27, 2013", (W/ English Translation), 12 pgs.
"Japanese Application Serial No. 2011-505080, Response filed May 25, 2015 to Office Action dated Feb. 25, 2015", No English Translation, 6 pgs.
"Japanese Application Serial No. 2011-505080, Response filed Jul. 3, 2013 to Office Action dated Apr. 3, 2013", (W/ English Translation), 11 pgs.
"Japanese Application Serial No. 2011-527885, Office Action dated Aug. 27, 2013", (English Translation), 8 pgs.
"Japanese Application Serial No. 2011-527885, Response filed Nov. 26, 2013 to Office Action dated Aug. 27, 2013", (W/ English Translation of Claims), 9 pgs.
"Japanese Application Serial No. 2013-537691, Office Action dated Feb. 10, 2015", No English Translation, 3 pgs.
"Japanese Application Serial No. 2013-537691, Office Action dated Apr. 15, 2014", (W/ English Translation), 2 pgs.
"Japanese Application Serial No. 2013-537691, Office Action datd Aug. 19, 2014", (W/ English Translation), 4 pgs.
"Japanese Application Serial No. 2013-537691, Response filed Jul. 5, 2014 to Office Action dated Apr. 15, 2014", No English Translation, 7 pgs.
"Japanese Application Serial No. 2013-537691, Response filed Dec. 19, 2014 to Office Action dated Aug. 19, 2014", No English Translation, 8 pgs.
"Japanese Application Serial No. 2014-257600, Examiners Decision of Final Refusal dated Dec. 20, 2016", (W/ English Translation), 2 pgs.
"Japanese Application Serial No. 2014-257600, Office Action dated May 24, 2016", (W/ English Translation), 5 pgs.
"Japanese Application Serial No. 2014-257600, Office Action dated Oct. 27, 2015", (W/ English Translation), 6 pgs.
"Japanese Application Serial No. 2014-257600, Response filed Jan. 20, 2016 to Office Action dated Oct. 27, 2015", (W/ English Translation of Claims), 5 pgs.
"Japanese Application Serial No. 2014-257600, Voluntary Amendment filed Dec. 19, 2014", No English Translation, 16 pgs.
"Japanese Application Serial No. 2014-511538, Office Action dated Apr. 7, 2015", (W/ English Translation), 5 pgs.
"Japanese Application Serial No. 2014-511538, Office Action dated Nov. 17, 2015", W/ English Translation, 5 pgs.
"Japanese Application Serial No. 2014-511538, Response filed Feb. 17, 2016 to Office Action dated Nov. 17, 2015", (W/ English Translation of Claims), 9 pgs.
"Japanese Application Serial No. 2014-511538, Response filed Jul. 6, 2015 to Office Action dated Apr. 7, 2015", No English Translation, 6 pgs.
"Japanese Application Serial No. 2014-558800, Office Action dated Sep. 1, 2015", (W/ English Translation), 8 pgs.
"Japanese Application Serial No. 2014-558800, Response filed Dec. 1, 2015 to Office Action dated Sep. 1, 2015", (W/ English Translation), 9 pgs.
"Japanese Application Serial No. 2014511538, Office Action dated Apr. 7, 2015", (W/ English Translation), 8 pgs.
"Knee tensor combined with laser femoral head locator", Research Disclosure, No. 507, (Jul. 2006), 903.
"Insall/Burstein II Modular Knee System", Zimmer, Inc., (1989), 20 pgs.
"Magnum™, M2a-Magnum™ Operative Technique", brochure. Biomet UK Ltd., (2008), 14 pgs.
"MAX-Ti™ Modular Protrusio Cage", Surgical Technique brochure. Biomet Orthopedics, Inc., (2003), 10 pgs.
"MAX-Ti™ Modular Protrusio Cage", Surgical Technique brochure. Biomet Orthopedics, Inc., (2006), 12 pgs.
"Method for constructing an allograft sleeve", Research Disclosure, No. 476, (Dec. 2003), 1294.
"Minimally Invasive Solution Technique—Instrumentation", The M/G Unicompartmental Knee, (2001), 4 pgs.
"MIS Minimally Invasive Solution, The M/G Unicompartmental Knee Minimally Invasive Surgical Technique", Zimmer, Inc. Nexgen Complete Knee Solution, 97-5791-02, (Aug. 14, 2008), 27 pgs.
"Nex Gen Complete Knee Solution-Intramedually Instrumentation Surgical Technique", NexGen Cruciate Retaining & Legacy Posterior Stablized Knee, (1994), 37 pgs.
"Nexgen Complete Knee Solution", Extramedullary/Intramedullary Tibial Resector: Surgical Technique, Zimmer, Inc. 97-5997-02 Rev 1, (2000), 26 pgs.
"NexGen Complete Knee Solution-Multi-Reference 4-in-1 Femoral Instrumentation-Anterior Reference Surgical Technique", (Aug. 1, 2001), 17 pgs.
"NexGen System Complete Knee Solution—Design Rationale", (date unknown), 26 pgs.
"Orthopaedic Salvage System Femoral/Tibial Augmentation", Biomet Orthopedics, Inc., Product Brochure, (2003, 2004), 12 pgs.
"OSS™ Orthopaedic Salvage System, Femoral/Tibial Augmentation", Biomet Orthopedics, Inc.,, (Mar. 31, 2004), 1-8.
"Oxford® Partial Knee", Biomet, (Feb. 2011), 8 pgs.
"Oxford® Partial Knee Microplasty® Instrumentation Surgical Technique", Biomet, (May 2011), 1-54.
"PAR 5™ Protrusio Acetabular Reconstruction System", Biomet Orthopedics, Inc., (2006), 12 pgs.
"Patient Matched PMI Implants, C.A.M.R.A. 3-D Imaging", Brochure, Biomet, Inc., Form Y-BMI-191/013191, (1991), 6 pgs.
"Proximal Tibial Replacement (MOST)", Zimmer MOST Options System Surgical Technique, (2005), 84 pgs.
"Regenerex® Porous Titanium Construct", Biomet brochure, (2011), 12 pgs.
"Regenerex® Tibial Cone Augment, Surgical Technique Addendum to the Vanguard® SSK Revision System", brochure. Biomet® Orthopedics., (Mar. 31, 2010), 1-8.
"Scorpio Single Axis Total Knee System—Passport Total Knee Instruments", Suri:iical TechniQue by Srvker Howmedica Osteonics, (2000), 54 pgs.
"Signature™ Hip Technology Personalized Patient Care brochure", Biomet® Orthopedics., (2013), 8 pgs.

(56) References Cited

OTHER PUBLICATIONS

"Signature™ Personalized Patient Care", Surgical Technique Acetabular Guide System brochure, Biomet® Orthopedics, (2013), 1-13.
"Signature™ Personalized Patient Care, Surgical Technique Addendum to the Vanguard Knee System", Biomet® Orthopedics Brochure, (May 15, 2009), 1-8.
"Simple Instruments Surgical Technique for the Knee", Biomet, Inc., (2000), 4 pgs.
"Subchondroplasty", [Online] retrieved from the internet: <http://www.subchondroplasty.com/>, (Jul. 1, 2013), 1 pg.
"Surgical Navigation for Total Knee Arthroplasty—Believed to have been presented at the American Academy of Orthopedic Surgeons", (Feb. 2001), 24 pgs.
"Surgical Technique for the Maxim®, Ascent™ and Vanguard™ Total Knee Systems", Microplasty™ minimally invasive knee instruments brochure, (Feb. 29, 2004), 15 pgs.
"Surgical Technique—Nexgen Complete Knee Solution for the Legacy Knee LPS-Flex Fixed Bearing Knee", Zimmer, Inc., (2004, 2007), 12 pgs.
"Taperloc Complete Hip System Surgical Technique", Biomet: Brochure 2012 REV061512, (2011), 12 pgS.
"The AGC Revision Knee System Surgical Technique", Biomet, Inc., (1997), 14 pgs.
"The Fudger™—The Ultimate Weapon in the Femoral Referencing War", Biomet, Inc., 2 pgs.
"The Oxford® Partial Knee Surgical Technique", Biomet, (Feb. 2010), 1-38.
"TruMatch™ Personalized knee replacement solutions", SIGMA® DePuy Orthopaedics, Inc, tri-fold brochure, (2009), 2 pgs.
"United Kingdom Application Serial No. 0619534.1, Search Report dated Dec. 18, 2006", (Dec. 8, 2006), 1 pg.
"United Kingdom Application Serial No. 1116054.6, Office Action dated Aug. 12, 2016", 2 pgs.
"United Kingdom Application Serial No. 1116054.6, Response filed Oct. 11, 2016 to Office Action dated Aug. 12, 2016", 12 pgs.
"United Kingdom Application Serial No. 11160546, First Examination Report dated Jun. 6, 2016", 4 pgs.
"United Kingdom Application Serial No. 1207103.1, Amendment filed Apr. 13, 2012", 9 pgs.
"United Kingdom Application Serial No. 1207103.1, Office Action dated May 14, 2015", 3 pgs.
"United Kingdom Application Serial No. 1207103.1, Office Action dated Oct. 6, 2015", 2 pgs.
"United Kingdom Application Serial No. 1207103.1, Response filed Sep. 14, 2015 to Office Action dated May 14, 2015", 22 pgs.
"United Kingdom Application Serial No. 1216577.5, Office Action dated Oct. 20, 2016", 4 pgs.
"United Kingdom Application Serial No. 1216577.5, Office Action dated Oct. 29, 2015", 4 pgs.
"United Kingdom Application Serial No. 1216577.5, Response filed Feb. 24, 2016 to Office Action dated Oct. 29, 2015", 27 pgs.
"United Kingdom Application Serial No. 1216577.5, Response filed Oct. 25, 2016 to Office Action dated Oct. 20, 2016", 24 pgs.
"United Kingdom Application Serial No. 1308746.5, Office Action dated Oct. 14, 2016", 5 pgs.
"United Kingdom Application Serial No. 1516672.1, Combined Search and Examination Report dated Oct. 22, 2015", 5 pgs.
"United Kingdom Application Serial No. 1516672.1, Office Action dated Mar. 7, 2016", 3 pgs.
"United Kingdom Application Serial No. 1516672.1, Response filed Feb. 22, 2016 to Combined Search and Examination Report dated Oct. 22, 2015", (English Translation of Claims), 37 pgs.
"United Kingdom Application Serial No. 1516672.1, Response filed Apr. 13, 2016 to Office Action dated Mar. 7, 2016", 13 pgs.
"Vanguard Complete Knee System", Biomet Othopedics, Vanguard, System Summary, (2011), 8 pgs.
"Vanguard® PFR Partial Knee Patellofemoral Replacement System", Surgical Technique, Biomet Orthopaedics (Aug. 31, 2010), 1-25.
"What is Subchondroplasty", [Online]. Retrieved from the Internet: <http://www.subchondroplasty.com/about subchondroplasty/what is subchondroplasty.>, (Jul. 1, 2013), 2 pgs.
"Zimmer MIS Multi-Reference 4-in-1 Femoral Instrumentation Surgical Technique", Zimmer, Inc., (2003, 2008, 2009), 48 pgs.
"Zimmer® UniSpacer® Knee System", Zimmer, Inc., (2005), 4 pgs.
Biomet, "The Oxford® Partial Knee System Surgical Technique", Biomet: Manual of the Surgical Technique, (Feb. 2010), 44 pgs.
Birnbaum, Klaus M. D, "Computer-Assisted Orthopedic Surgery With Individual Templates and Comparison to Conventional Method", SPINE vol. 26, No. 4, Lippincott Williams & Wilkins, Inc., (2001), 365-370.
Botha, Charl P, "Technical Report: DeVIDE—The Delft Visualisation and Image processing Development Environment", (May 31, 2006), 1-49.
Clohisy, John C, et al., "Periacetabular Osteotomy in the Treatment of Severe Acetabular Dysplasia", The Journal of Bone & Joint Surgery, vol. 87-A • No. 2, (2005), 7 pgs.
Cohen, Zohara A, et al., "Knee cartilage topography, thickness, and contact areas from MRI: in-vitro calibration and in-vivo measurements", Journal of the OsteoArthritis Research Society International. Osteoarthritis and Cartilage, vol. 7; No. 1, (1999), 95-109.
Deakon, "Posterior Cruciate Ligament Reconstruction Technique Using the Modular ACL/PCL Guide Rationale and Surgical Technique", Arthrotek®, a Biomet Company, (2003), 6 pgs.
Eckhoff, Donald G, et al., "Three-Dimensional Mechanics, Kinematics, and Morphology of the Knee Viewed in Virtual Reality", The Journal of Bone & Joint Surgery, vol. 81, (Dec. 4, 2005), 71-80.
Farr, J, et al., "Anteromedial Tibial Tubercle Osteotomy (Fulkerson Osteotomy)", Re-print from V. Sanchis-Alfonso (ed), Anterior Knee Pain and patellar Instability, DOI: 10.1007/978-0-85729-507-1_40, © Springer-Verlag London Limited, (2011), 9 pgs.
Farr, J, et al., "Surgical Technique for Anteromedialization of the Tibial Tubercle with the Tracker™ AMZ Guide System", Sports Medicine and Arthroscopy Review, vol. 2, No. 3, (1994), 12 pgs.
Fortin, Thomas, et al., "Precise Dental Implant Placement in Bone Using Surgical Guides in Conjunction with Medical Imaging Techniques", Journal of Oral Implantology, Clinical, vol. 26, No. 4, (2000), 300-303.
Friedman, R J, et al., "The Use of Computerized Tomography in the Measurement of Glenoid Version", Journal of Bone & Joint Surgery Am. (JBJS) 1992;74, (Aug. 1992), 1032-1037.
Genant, H K, et al., "Advanced CT bone imaging in osteoporosis", Rheumatology, 47, (2008), 8 pgs.
Guldberg, et al., "3D Imaging of Tissue Integration with Porous Biomaterials", Biomaterials, 29, (Oct. 2008), 3757-3761.
Haaker, R G, et al., "Minimal-invasive navigiert implantierte unikondylare Knieendoprothese", Orthopade 2006 35: Spinger Medizin Verlag, (Sep. 13, 2006), 1073-1079.
Hafez, M A, et al., "Computer-assisted Total Knee Arthroplasty Using Patient-specific Templating", Clinical Orthopaedics and Related Research, No. 444 Lippincott Williams & Wilkins, (2006), 184-192.
Hazan, Eric J, "Computer-Assisted Orthopaedic Surgery, A New Paradigm", Techniques in Orthopaedics® vol. 18, No. 2 (2003), 221-229.
Hitt, Kirby, et al., "Anthropometric Measurements of the Human Knee: Correlation to the Sizing of Current Knee Arthroplasty Systems", The Journal of Bone & Joint Surgery, (2003), 114-122.
Hutmacher, Dietmar W, "Scaffolds in tissue engineering bone and cartilage", Biomaterials, 21(24), (2000), 2529-2543.
Kaus, Michael R, "Automated Segmentation of MR Images of Brain Tumors", Radiology, vol. 218, No. 2,, (2001), 586-591.
Kelly, Todd C, "Role of Navigation in Total Hip Arthroplasty", The Journal of Bone & Joint Surgery(2009) vol. 91-A, Supplement 1, (2009), 153-8.
Keys, Graham W., "Reduced Invasive Approach for Oxford II Medial Unicompartmental Knee Replacement—a Preliminary Study", The Knee, (1999), 193-196.
Klein, M, "Robot assisted insertion of craniofacial implants—clinical experience", CARS 2001, Elsevier Science B.V., (2001), 133-138.

(56) References Cited

OTHER PUBLICATIONS

Lombardi, Adolph, et al., "Patient-Specific Approach in Total Knee Arthroplasty", Knee Orthopedics, ORTHOSuperSite, [Online]. Retrieved from the Internet: <http://www.orthosupersite.com/view.aspx?rid=31419,>, (Sep. 1, 2008), 5 pgs.

Lynch, John A, et al., "Cartilage segmentation of 3D MRI scans of the osteoarthritic knee combining user knowledge and active contours", Medical Imaging 2000: Image Processing SPIE vol. 3979, (2000), 925-935.

Masatoshi, Naito, et al., "Curved Periacetabular Osteotomy for Treatment of Dysplastic Hip", Clinical Orthopaedics and Related Research, (Apr. 2005), 129-135.

Miller, et al., "Unicompartmental Knee System", The Miller/Galante Advantage; Zimmer, 11 pgs.

Miller, Nancy H, et al., "Long-term Results of the Dial Osteotomy in the Treatment of High-grade Acetabular Dysplasia", Clinical Orthopaedics and Related Research, (2005), 115-123.

Murphy, S B, et al., "The Hip Sextant: Navigation of Acetabular Component Orientation Using a Mechanical Instrument", (2009), 1 pg.

Nicholls, Paul M. D, "Trauma Grand Rounds PMI (Patient-Matched Implants)", Biomet Orthopedics, Inc.,, (Feb. 29, 2000), 1 pg.

Overhoff, H M, et al., "Total Knee Arthroplasty: Coordinate System Definition and Planning based on 3-D Ultrasound Image Volumes", CARS 2001, Elsevier Science B.V., (2001), 283-288.

Patsch, J M, et al., "Noninvasive imaging of bone microarchitecture", Annals of the NY Academy of Sciences, (2011), 77-87.

Portheine, F, "CT-basierte Planung und DISOS-Schablonennavigation in der Kniegelenkendoprothetik", Navigation und Robotic in der Gelenk—und Wirbelsaulenchiruqie, Kapitel 32, Springer Verlag, (2003), 262-269.

Portheine, F, et al., "Entwicklung eines klinischen Demonstrators fur die computerunterstutzte Orthopadische Chirurgie mit CT-Bildbasierten Individualschablonen, Bildverarbeitung fur die Medizin", English version: FIP ID 752773, (1998), 5 pgs.

Portheine, K, "Development of a clinical demonstrator for computer assisted orthopedic surgery with CT-image based individual templates", Computer Assisted Radiology and Surgery Elsevier Science B.V., English Version of FIP ID 752770, (1997), 944-949.

Radermacher, K, et al., "Computer Integrated Orthopaedic Surgery: Connection of Planning and Execution in Surgical Intervention", Computer-integrated surgery: technology and clinical applications, (1996), 451-463.

Radermacher, K, et al., "CT Image-Based Planning and Execution of Interventions in Orthopedic Surgery Using Individual Templates, Experimental Results and Aspects of Clinical Applications", Computer Assisted Orthopedic Surgery (CAOS), Hogrefe & Huber Publishers, (1995), 42-52.

Radermacher, K, et al., "Image Guided Orthopedic Surgery Using Individual Templates", Springer Berlin/Heidelberg, CVRMed-MRCAS'97, vol. 1205, (1997), 606-615.

Radermacher, K, et al., "Technique for Better Execution of CT Scan Planned Orthopedic Surgery on Bone Structures", British Library—"The world's knowledge" 2nd Congress of ISCAS Conference, (Jun. 1995), 933-938.

Radermacher, Klaus, et al., "Computer Assisted Orthopaedic Surgery with Image Based Individual Templates", Clinical Orthopaedics and Related Research No. 354, Lippincott Williams & Wilkins, (Sep. 1998), 28-38.

Schuller-Gotzburg, P, et al., "3D-Implantatplanung und Stereolithographie-Implantatbohrschablonen", Stomatologie 101.3, (May 2004), 55-59.

Sharp, Michael S, "Patient-Specific, Resurfacing Bi-Compartmental Arthuroplasty Futuretech", Orthopaedic Product News, (Apr. 2008), 12-15.

Sisto, Domenick J, et al., "Custom Patellofemoral Arthroplasty of the Knee Surgical Technique", Journal of Bone and Joint Surgery, vol. 89-A, (2006), 214-225.

Slamin, John, et al., "Do You Have This Implant in My Size?", MDT Medical Design Technology, [Online]. Retrieved from the Internet: <http://www.mdtmag.com/scripts/ShowPR.asp?PUBCODE=046&ACCT=0007796& ISSUE . . . >, (Jul. 31, 2008), 3 pgs.

Steinwachs, Matthias Reinhard, "Cartilage Repair—Autologous Chondrocyte Transplantation and Autologous Matrix-induced Chondrogenesis", European Musculoskeletal Review, (2006), 65-68.

Subburaj, K, et al., "Automated 3D Geometric Reasoning in Computer Assisted Joint Reconstructive Surgery", IEEE International Conference on Automation Science and Engineering, (2009), 367-372.

Thoma, W, et al., "Endoprothetischen Versorgung des Kniegelenks auf der Basis eines 3D-computertomographischen Subtraktionsverfahrens", Topic: Computer-aided orthopedic surgery. Orthopedist 2000 29: Springer Verlag W/ Original German Document, (2000), 641-644.

Tripp, et al., "A Nondestructive Prescreening Method for Bone Collagen Content Using Micro-Computed Tomography", Radiocarbon, vol. 52, (2010), 612-619.

Yasunaga, Yuji, et al., "Rotational Acetabular Osteotomy for Advanced Osteoarthritis Secondary to Dysplasia of the Hip. Surgical Technique", The Journal of Bone & Joint Surgery, (2007), 11 pgs.

U.S. Appl. No. 15/911,701, filed Mar. 5, 2018, Virtual Surgery Planning System and Method.

U.S. Appl. No. 15/878,984, filed Jan. 24, 2018, Alignment Guides With Patient-Specific Anchoring Elements.

U.S. Appl. No. 15/875,204, filed Jan. 19, 2018, Method and Apparatus for Manufacturing an Implant.

U.S. Appl. No. 15/863,421, filed Jan. 5, 2018, Patient-Specific Acetabular Alignment Guides.

U.S. Appl. No. 15/887,740, filed Feb. 2, 2018, Backup Surgical Instrument System and Method.

U.S. Appl. No. 15/933,576, filed Mar. 23, 2018, Patient-Specific Orthopedic Instruments.

U.S. Appl. No. 11/363,548 U.S. Pat. No. 7,780,672, filed Feb. 27, 2006, Femoral Adjustment Device and Associated Method.

U.S. Appl. No. 11/756,057 U.S. Pat. No. 8,092,465, filed May 31, 2007, Patient Specific Knee Alignment Guide and Associated Method.

U.S. Appl. No. 13/303,546 U.S. Pat. No. 8,398,646, filed Nov. 23, 2011, Patient-Specific Knee Alignment Guide and Associated Method.

U.S. Appl. No. 13/800,334, filed Mar. 13, 2013, Patient-Specific Knee Alignment Guide and Associated Method.

U.S. Appl. No. 12/103,834 U.S. Pat. No. 7,967,868, filed Apr. 16, 2008 Patient-Modified Implant and Associated Method.

U.S. Appl. No. 12/103,824, filed Apr. 16, 2008, Method and Apparatus for Manufacturing an Implant.

U.S. Appl. No. 13/081,618 U.S. Pat. No. 8,486,150, filed Apr. 7, 2011, Patient-Modified Implant.

U.S. Appl. No. 13/923,827 U.S. Pat. No. 8,979,936, filed Jun. 21, 2013, Patient-Modified Implant.

U.S. Appl. No. 14/658,429, filed Mar. 16, 2015, Patient-Modified Implant.

U.S. Appl. No. 15/130,414, filed Apr. 15, 2016, Patient-Specific Acetabular Guides and Associated Instruments.

U.S. Appl. No. 15/672,724, filed Aug. 9, 2017, Patient-Specific Augments.

U.S. Appl. No. 13/041,883, filed Mar. 7, 2011, Patient-Specific Femoral Guide.

U.S. Appl. No. 13/041,495 U.S. Pat. No. 8,864,769, filed Mar. 7, 2011, Alignment Guides With Patient-Specific Anchoring Elements.

U.S. Appl. No. 13/041,469 U.S. Pat. No. 8,608,749, filed Mar. 7, 2011, Patient-Specific Acetabular Guides and Associated Instruments.

U.S. Appl. No. 13/047,924, filed Mar. 15, 2011, Patient-Specific Augments.

U.S. Appl. No. 13/045,169, filed Mar. 10, 2011, Instrument With Transparent Portion for Use With Patient-Specific Alignment Guide.

U.S. Appl. No. 13/400,652 U.S. Pat. No. 9,339,278, filed Feb. 21, 2012, Patient-Specific Acetabular Guides and Associated Instruments.

U.S. Appl. No. 14/483,214, filed Sep. 11, 2014, Alignment Guides With Patient-Specific Anchoring Elements.

U.S. Appl. No. 14/105,669, U.S. Pat. No. 9,662,127, filed Dec. 13, 2013, Patient-Specific Acetabular Guides and Associated Instruments.

(56) References Cited

OTHER PUBLICATIONS

U.S. Appl. No. 14/812,583, filed Jul. 29, 2015, Patient-Specific Augments.
U.S. Appl. No. 12/872,663, U.S. Pat. No. 8,407,067, filed Aug. 31, 2010, Method and Apparatus for Manufacturing an Implant.
U.S. Appl. No. 13/766,419, filed Feb, 13, 2013, Method and Apparatus for Manufacturing an Implant.
U.S. Appl. No. 14/739,160, filed Jun. 15, 2015, Method and Apparatus for Manufacturing an Implant.
U.S. Appl. No. 11/971,390 U.S. Pat. No. 8,070,752, filed Jan. 9, 2008, Patient Specific Alignment Guide and Inter-Operative Adjustment.
U.S. Appl. No. 12/025,414 U.S. Pat. No. 8,298,237, filed Feb. 4, 2008, Patient-Specific Alignment Guide for Multiple Incisions.
U.S. Appl. No. 12/371,096, filed Feb. 13, 2009, Method and Apparatus for Manufacturing an Implant.
U.S. Appl. No. 12/483,807 U.S. Pat. No. 8,473,305, filed Jun. 12, 2009, Method and Apparatus for Manufacturing an Implant.
U.S. Appl. No. 12/039,849 U.S. Pat. No. 8,282,646, filed Feb. 29, 2008, Patient Specific Knee Alignment Guide and Associated Method.
U.S. Appl. No. 12/211,407 U.S. Pat. No. 8,608,748, filed Sep. 16, 2008, Patient Specific Guides.
U.S. Appl. No. 14/107,316 U.S. Pat. No. 9,480,490, filed Dec. 16, 2013, Patient-Specific Guides.
U.S. Appl. No. 12/389,901 U.S. Pat. No. 8,133,234, filed Feb. 20, 2009, Patient Specific Acetabular Guide and Method.
U.S. Appl. No. 13/343,957 U.S. Pat. No. 8,900,244, filed Jan. 5, 2012, Patient Specific Acetabular Guide and Method.
U.S. Appl. No. 12/486,992 U.S. Pat. No. 8,858,561, filed Jun. 18, 2009, Patient-Specific Alignment Guide.
U.S. Appl. No. 12/571,969 U.S. Pat. No. 9,173,661, filed Oct. 1, 2009, Patient Specific Alignment Guide With Cutting Surface and Laser Indicator.
U.S. Appl. No. 14/865,762, filed Sep. 25, 2015, Patient Specific Alignment Guide With Cutting Surface and Laser Indicator.
U.S. Appl. No. 12/714,023 U.S. Pat. No. 8,241,293, filed Feb. 26, 2010, Patient Specific High Tibia Osteotomy.
U.S. Appl. No. 13/572,895 U.S. Pat. No. 8,828,087, filed Aug. 13, 2012, Patient-Specific High Tibia Osteotomy.
U.S. Appl. No. 12/888,005 U.S. Pat. No. 8,377,066, filed Sep. 22, 2010, Patient-Specific Elbow Guides and Associated Methods.
U.S. Appl. No. 13/744,022 U.S. Pat. No. 9,005,297, filed Jan. 17, 2013, Patient-Specific Elbow Guides and Associated Methods.
U.S. Appl. No. 14/684,936 U.S. Pat. No. 9,539,013, filed Apr. 13, 2015, Patient-Specific Elbow Guides and Associated Methods.
U.S. Appl. No. 12/893,306 U.S. Pat. No. 9,113,971, filed Sep. 29, 2010, Femoral Acetabular Impingement Guide.
U.S. Appl. No. 14/798,809, filed Jul. 14, 2015, Femoral Acetabular Impingement Guide.
U.S. Appl. No. 12/938,913 U.S. Pat. No. 9,289,253, filed Nov. 3, 2010, Patient-Specific Shoulder Guide.
U.S. Appl. No. 15/008,528, filed Jan. 28, 2016, Patient-Specific Shoulder Guide.
U.S. Appl. No. 12/938,905, filed Nov. 3, 2010, Patient-Specific Implants.
U.S. Appl. No. 12/955,361 U.S. Pat. No. 8,591,516, filed Nov. 29, 2010, Patient-Specific Orthopedic Instruments.
U.S. Appl. No. 12/973,214 U.S. Pat. No. 9,345,548, filed Dec. 20, 2010, Patient-Specific Pre-Operative Planning.
U.S. Appl. No. 15/093,384, filed Apr. 7, 2016. Patient-Specific Pre-Operative Planning.
U.S. Appl. No. 12/255,945 U.S. Pat. No. 9,730,616, filed Oct. 22, 2008, Mechanical Axis Alignment Using MRI Imaging.
U.S. Appl. No. 15/650,035, filed Jul. 14, 2017, Mechanical Axis Alignment Using MRI Imaging.
U.S. Appl. No. 12/978,069 U.S. Pat. No. 8,568,487, filed Dec. 23, 2010, Patient-Specific Hip Joint Devices.
U.S. Appl. No. 14/064,970 U.S. Pat. No. 9,662,216, filed Oct. 28, 2013, Patient-Specific Hip Joint Devices.
U.S. Appl. No. 15/495,432, filed Apr. 24, 2017, Patient-Specific Hip Joint Devices.
U.S. Appl. No. 13/041,665 U.S. Pat. No. 8,535,387, filed Mar. 7, 2011, Patient-Specific Tools and Implants.
U.S. Appl. No. 14/027,340 U.S. Pat. No. 9,445,907, filed Sep. 16, 2013, Patient-Specific Tools and Implants.
U.S. Appl. No. 15/224,741, filed Aug. 1, 2016, Patient-Specific Tools and Implants.
U.S. Appl. No. 13/111,007 U.S. Pat. No. 8,603,180, filed May 19, 2011, Patient-Specific Acetabular Guides and Associated Instruments.
U.S. Appl. No. 14/100,134 U.S. Pat. No. 9,480,580, filed Dec. 9, 2013, Patient-Specific Acetabular Alignment Guides.
U.S. Appl. No. 15/267,714, filed Sep. 16, 2016, Patient-Specific Acetabular Alignment Guides.
U.S. Appl. No. 13/527,981, filed Jun. 20, 2012, Backup Surgical Instrument System and Method.
U.S. Appl. No. 14/327,234, filed Jul. 9, 2014, Patient-Specific Knee Alignment Guide and Associated Method.
U.S. Appl. No. 13/713,710 U.S. Pat. No. 9,241,745, filed Dec. 13, 2012, Patient-Specific Femoral Version Guide.
U.S. Appl. No. 14/973,057 U.S. Pat. No. 9,743,935, filed Dec. 17, 2015, Patient-Specific Femoral Version Guide.
U.S. Appl. No. 13/106,295 U.S. Pat. No. 8,632,547, filed May 12, 2011, Patient-Specific Osteotomy Devices and Methods.
U.S. Appl. No. 14/086,447 U.S. Pat. No. 9,522,010, filed Nov. 21, 2013, Patient-Specific Orthopedic Instruments.
U.S. Appl. No. 15/352,721 U.S. Pat. No. 9,700,329, filed Nov. 16, 2016, Patient-Specific Orthopedic Instruments.
U.S. Appl. No. 15/618,331, filed Jun. 9, 2017, Patient-Specific Orthopedic Instruments.
"U.S. Appl. No. 15/933,576, Preliminary Amendment Filed Apr. 17, 2018", 6 pgs.
"U.S. Appl. No. 14/798,809, Notice of Allowance dated May 3, 2018", 7 pgs.
"U.S. Appl. No. 15/495,432, Non Final Office Action dated May 9, 2018", 9 pgs.
"U.S. Appl. No. 15/972,591, Preliminary Amendment Filed May 21, 2018", 6 pgs.
"European Application Serial No. 10705951.1, Communication Pursuant to Article 94(3) EPC dated May 23, 2018", 7 pgs.
"U.S. Appl. No. 14/865,762, Response filed Jun. 8, 2018 to Non Final Office Action dated Mar. 8, 2018", 17 pgs.
"U.S. Appl. No. 15/008,528, Non Final Office Action dated Jun. 11, 2018", 13 pgs.
"U.S. Appl. No. 15/224,741, Non Final Office Action dated Jun. 11, 2018", 10 pgs.
"U.S. Appl. No. 15/130,414, Non Final Office Action dated Jul. 27, 2018", 7 pgs.
"U.S. Appl. No. 14/739,160, Notice of Allowance dated Aug. 6, 2018", 9 pgs.
"U.S. Appl. No. 14/739,160, Response filed Apr. 16, 2018 to Non Final Office Action dated Jan. 16, 2018", 19 pgs.
"U.S. Appl. No. 15/887,740, Preliminary Amendment Filed Apr. 27, 2018", 8 pgs.
"U.S. Appl. No. 14/798,809, Corrected Notice of Allowability dated Jun. 27, 2018", 4 pgs.
"U.S. Appl. No. 15/008,528, Response Filed Sep. 11, 2018 to Non-Final Office Action dated Jun. 11, 2018", 14 pgs.
"U.S. Appl. No. 14/865,762, Non Final Office Action dated Aug. 27, 2018", 15 pgs.
"European Application Serial No. 17188434.9, Extended European Search Report dated Aug. 30, 2018", 9 pgs.
"U.S. Appl. No. 15/224,741, Response filed May 14, 2018 to Restriction Requirement dated Mar. 15, 2018", 8 pgs.
"U.S. Appl. No. 13/041,883, Appeal Decision mailed Sep. 13, 2018", 13 pgs.
"U.S. Appl. No. 14/798,809, Notice of Allowance dated Sep. 24, 2018", 6 pgs.

* cited by examiner

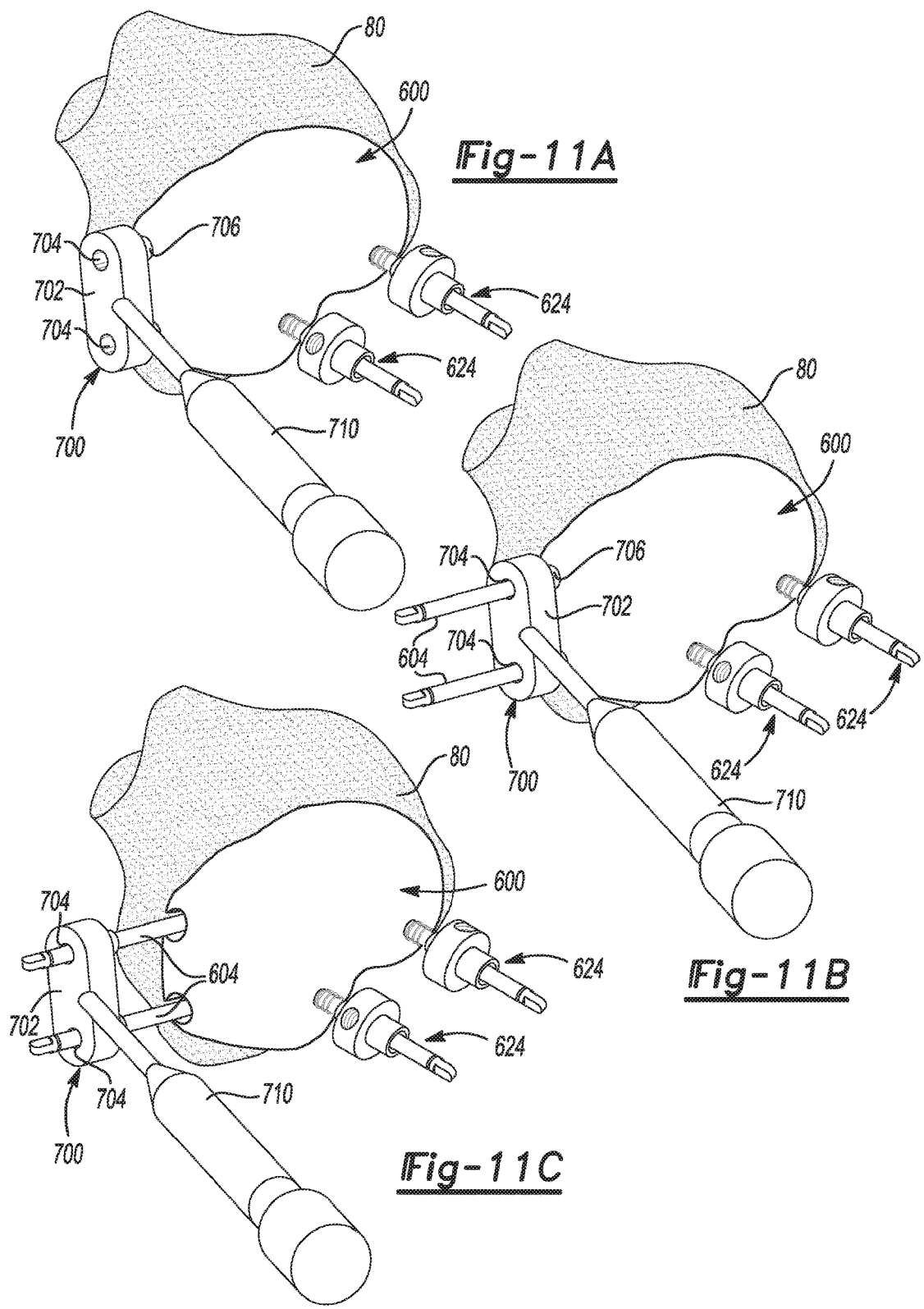

PATIENT-SPECIFIC KNEE ALIGNMENT GUIDE AND ASSOCIATED METHOD

CROSS-REFERENCE TO RELATED APPLICATIONS

This application is continuation-in-part of U.S. patent application Ser. No. 13/800,334 filed on Mar. 13, 2013, which is a divisional of U.S. patent application Ser. No. 13/303,546 filed on Nov. 23, 2011, now U.S. Pat. No. 8,398,646 issued on Mar. 19, 2013, which is a continuation of U.S. patent application Ser. No. 11/756,057 filed on May 31, 2007, which is now U.S. Pat. No. 8,092,465 issued on Jan. 10, 2012, which claims the benefit of U.S. Provisional Application No. 60/812,694 filed on Jun. 9, 2006. The disclosures of the above applications are incorporated herein by reference.

INTRODUCTION

Proper alignment of prosthetic components in knee arthroscopy is an important factor in the longevity and function of the implant. Misalignment can cause increased wear of the implant, patient discomfort, and functional limitation.

Although various methods and devices are known for addressing the above problems, patient specific alignment methods and alignment guides are still desirable.

SUMMARY

The present teachings provide a method of preparing a joint for a prosthesis in a patient. In one aspect, the method includes obtaining scan data associated with the joint of the patient, preparing a three-dimensional image of the joint based on the scan data, preparing an interactive initial surgical plan based on the scan data, sending the surgical plan to a surgeon, receiving a finalized surgical plan from surgeon, and preparing an image of a patient-specific alignment guide.

In another aspect, the method includes securing a patient-specific alignment guide to a joint surface of the patient, attaching a guide element through the alignment guide to the joint surface, removing the alignment guide without removing the guide element, and resecting the joint surface using the guide element.

The present teachings also provide a method of preparing a knee joint for a prosthesis in a patient. The method includes locking a patient-specific femoral alignment guide onto a femoral joint surface of the patient, inserting at least one first guide element through the femoral alignment guide into the anterior or the anterior-medial side of the femoral joint surface, and drilling resection-locating apertures in the distal side of femoral joint surface. The method further includes removing the femoral alignment guide without removing the first guide element, supporting a femoral resection device on the first guide element, and resecting the femoral joint surface.

The present teachings further provide an orthopedic device for preparing a knee joint for a prosthesis in a patient. The orthopedic device includes a femoral alignment guide having a patient-specific three-dimensional curved inner surface. The curved inner surface is preoperatively configured from medical image scans of the knee joint of the patient to nestingly conform and mate and match only in one position to a corresponding three-dimensional femoral surface of a joint surface of the patient. The femoral alignment guide has a first guiding aperture corresponding to a distal portion of the femoral surface and a second guiding aperture corresponding to an anterior portion of the femoral surface.

According to various embodiments, a method of preparing a knee joint for a prosthesis in a patient is disclosed. The method includes mating a patient-specific three-dimensional curved inner surface of a femoral alignment guide onto a corresponding three-dimensional femoral joint surface of the patient, the patient-specific three-dimensional curved inner surface preoperatively configured from medical scans of the knee joint of the patient, drilling a first hole into an anterior portion of the femoral joint surface through a corresponding first guiding aperture of the femoral alignment guide and drilling a second hole into an anterior portion of the femoral joint surface through a corresponding second guiding aperture of the femoral alignment guide. In the method, the second guiding aperture is asymmetrically located relative to the first guiding aperture on the femoral alignment guide. The method can further include mating a portion of the inner surface of the femoral alignment guide to articular cartilage covering the femoral joint surface. The method can further include mating a portion of the inner surface of the femoral alignment guide to a bone portion underlying articular cartilage of the femoral joint surface. The method can further include inserting first and second guiding pins through the corresponding first and second guiding apertures and first and second holes. The method can further include removing the femoral alignment guide without removing the first and second guiding pins. The method can further include sliding the femoral alignment guide through open portions of corresponding perimeters of the first and second guiding apertures. The method can further include supporting a cutting block on the first and second guiding pins. The method can further include guiding a patient-specific femoral resection through the cutting block, the patient-specific resection determined by preoperative configuring the first and second guiding apertures on the femoral alignment guide to correspond to the patient-specific resection.

According to various embodiments, a method of preparing a knee joint for a prosthesis in a patient may include mating a patient-specific three-dimensional curved inner surface of a femoral alignment guide onto a corresponding three-dimensional femoral joint surface of a patient, the patient-specific three-dimensional curved inner surface preoperatively configured from medical scans of the knee joint of the patient, drilling first and second holes into an anterior portion of the femoral joint surface through corresponding first and second guiding apertures of the femoral alignment guide, wherein the first and second guiding apertures are preoperative configured for locating a femoral resection of the patient according to the medical scans of the patient and a preoperative surgical plan for the patient, and inserting first and second guiding pins through the corresponding first and second guiding apertures and the first and second holes. The method may further include removing the femoral alignment guide without removing the first and second guiding pins. The method may further include sliding the femoral alignment guide through open portions of corresponding perimeters of the first and second guiding apertures. The method may further include supporting a cutting block on the first and second guiding pins. The method may further include guiding a patient-specific femoral resection through the cutting block. The method may further include mating a portion of the inner surface of the femoral alignment guide to at least one of articular cartilage and underlying bone of the femoral joint surface.

According to various embodiments, a method of preparing a knee joint for a prosthesis in a patient can include mating a patient-specific three-dimensional curved inner surface of a tibial alignment guide onto a corresponding three-dimensional tibial joint surface of the patient, the patient-specific three-dimensional curved inner surface pre-operatively configured from medical scans of the knee joint of the patient, and wrapping a portion of the tibial alignment guide around an anterior-medial edge of the tibial joint surface. The method may further include drilling a first tibial guiding hole into an anterior portion of the tibial joint surface through a first corresponding anterior aperture of the tibial alignment guide. The method may further include drilling a second tibial guiding hole into an anterior portion of the tibial joint surface through a second corresponding anterior aperture of the tibial alignment guide. The method may further include inserting first and second guiding pins through the corresponding first and second anterior apertures and into the corresponding first and second tibial guiding holes. The method may further include removing the tibial alignment guide without removing the first and second guiding pins by sliding the tibial alignment guide through open portions of corresponding perimeters of the first and second anterior apertures of the tibial alignment guide.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 11A is a perspective view of the femoralalignment guide of FIG. 8 shown with a drill guide;

FIG. 11B is a perspective view of the femoral alignment guide of FIG. 11A shown with two guide pins drilled through the drill guide;

FIG. 11C is perspective view of the femoral alignment guide of FIG. 11B showing the removal of the drill guide;

DESCRIPTION OF VARIOUS ASPECTS

The following description is merely exemplary in nature and is in no way intended to limit the scope of the present teachings, applications, or uses. For example, although the present teachings are illustrated for alignment guides in knee surgery, the present teachings can be used for other guides, templates, jigs, drills, rasps or other instruments used in various orthopedic procedures.

The present teachings provide a method for preparing patient-specific alignment guides for use in orthopedic surgery for a joint, such as, for example, the knee joint. Conventional, not patient-specific, prosthesis components available in different sizes can be used with the alignment guides, although patient-specific femoral and tibial prosthesis components prepared with computer-assisted image methods can also be used. Computer modeling for obtaining three dimensional images of the patient's anatomy, such as a patient's joint, for example, the patient-specific prosthesis components, when used, and the alignment guides and templates can be provided by various CAD programs and/or software available from various vendors or developers, such as, for example, from Materialise USA, Ann Arbor, Mich.

Figure 1:
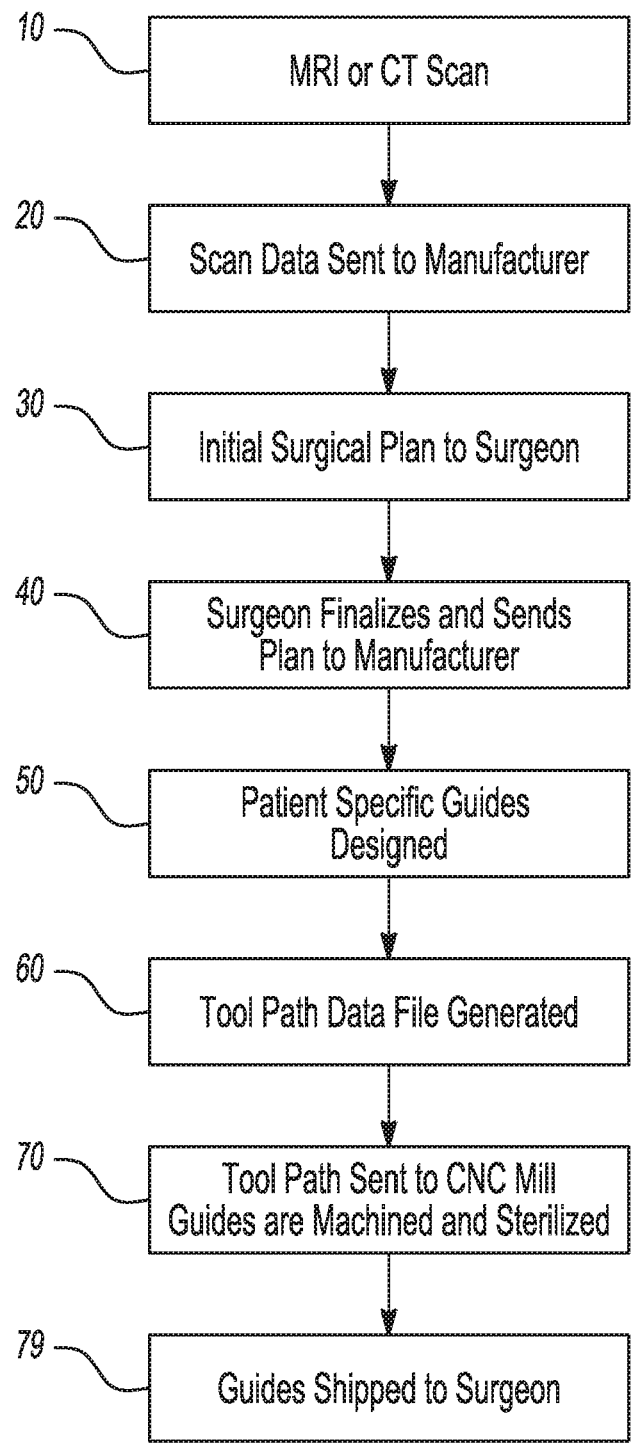
FIG. 1 is a flowchart of an exemplary method of preparing patient specific alignment guides according to the present teachings.
Figure 2:
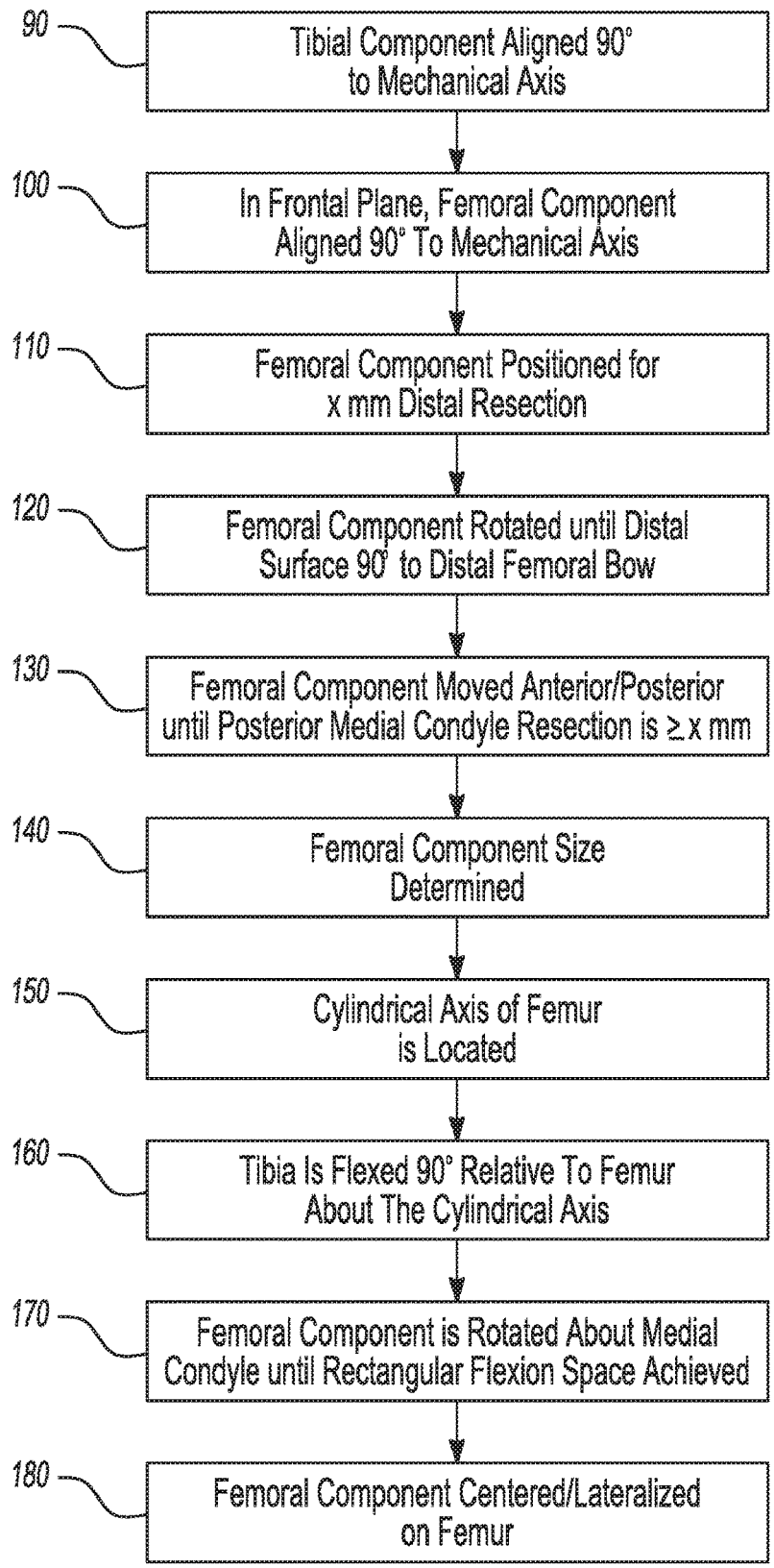
FIG. 2 is a flowchart of an alignment method according to the present teachings.
Figure 3:
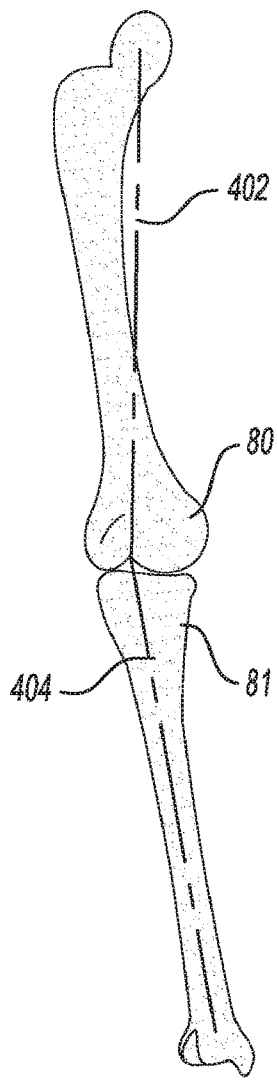
FIG. 3 is a view illustrating the mechanical axis in a patient's anatomic image.

Referring to FIG. 1, an MRI scan or a series of CT scans of the entire leg of the joint to be reconstructed, including hip and ankle, as shown in FIG. 3, can be performed at a medical facility or doctor's office, at aspect 10. In some cases, the scan may be performed with the patient wearing an unloader brace to stress the ligaments. The scan data obtained can be sent to a manufacturer, at aspect 20. The scan data can be used to construct a three-dimensional image of the joint and provide an initial implant fitting and alignment in a computer file form or other computer representation. The initial implant fitting and alignment can be obtained using an alignment method, such as the alignment method illustrated in FIG. 2 and described below. Other alignment methods can also be used, such as alignment protocols used by individual surgeons.

Figure 7:
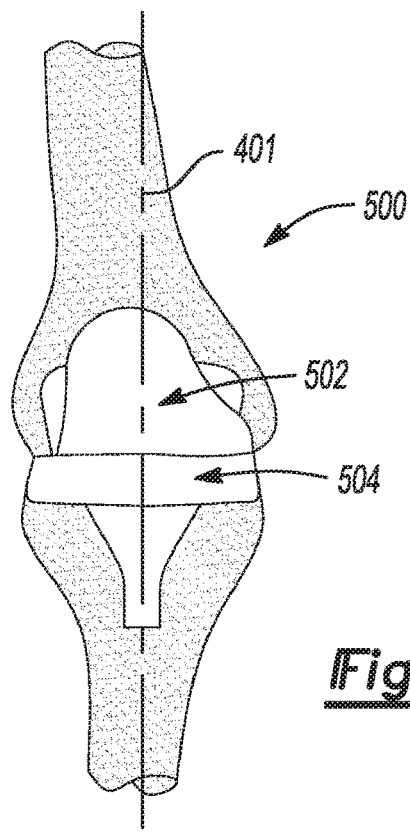
FIG. 7 is an exemplary image of a patient's anatomy with implants shown, as viewed in interactive software according to the present teachings.

The outcome of the initial fitting is an initial surgical plan that can be printed or provided in electronic form with corresponding viewing software. The initial surgical plan can be surgeon-specific, when using surgeon-specific alignment protocols. The initial surgical plan, in a computer file form associated with interactive software, can be sent to the surgeon, or other medical practitioner, for review, at 30. The surgeon can incrementally manipulate the position of images of implant components 502, 504 in an interactive image form 500 of the joint, as illustrated in FIG. 7. After the surgeon modifies and/or approves the surgical plan, the surgeon can send the final, approved plan to the manufacturer, at 40.

Various methods of sending the initial and final surgeon-approved surgical plans can be used. The surgical plans can be, for example, transferred to an electronic storage medium, such as CD, DVD, flash memory, which can then be mailed using regular posting methods. Alternatively, the surgical plan can be e-mailed in electronic form or transmitted through the internet or other web-based service, without the use of a storage medium.

After the surgical plan is approved by the surgeon, patient-specific alignment guides for the femur and tibia can be developed using a CAD program or other imaging software, such as the software provided by Materialise, for example, according to the surgical plan, at 50. Computer instructions of tool paths for machining the patient-specific alignment guides can be generated and stored in a tool path data file, at 60. The tool path can be provided as input to a CNC mill or other automated machining system, and the alignment guides can be machined from polymer, ceramic, metal or other suitable material, and sterilized, at 70. The sterilized alignment guides can be shipped to the surgeon or medical facility, at aspect 79 for use during the surgical procedure.

Figure 4:
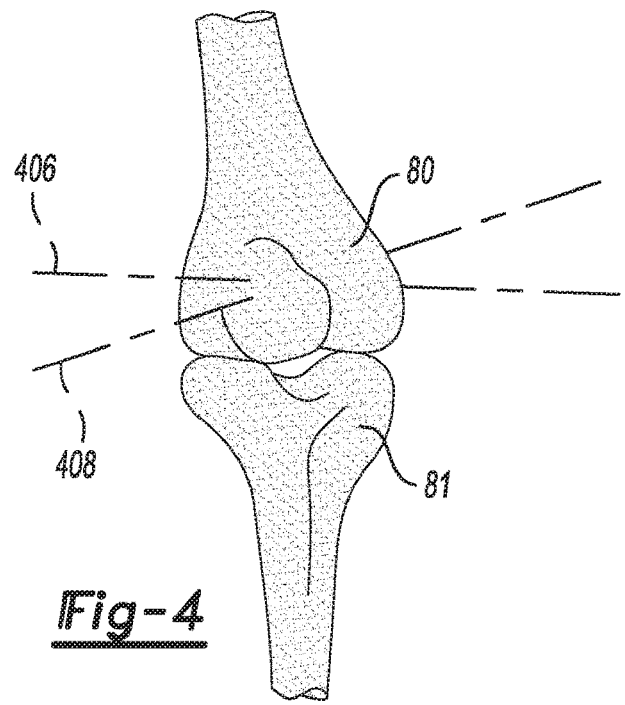
FIG. 4 is a view illustrating the t ansepicondylar and cylindrical axes in a patient's anatomic image.
Figure 8:
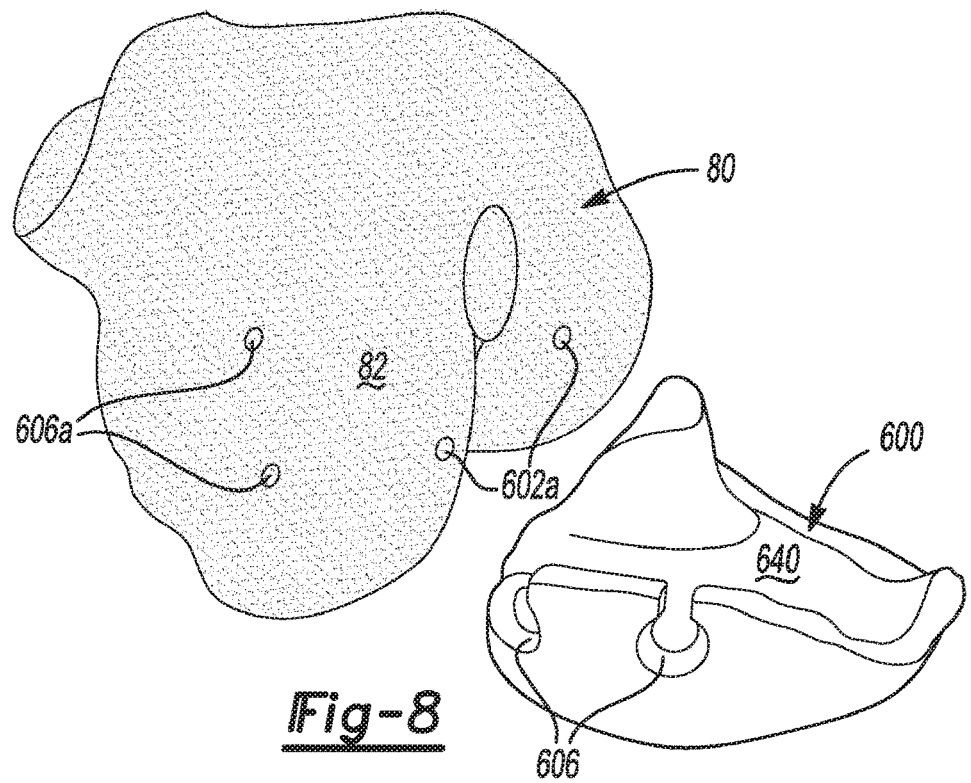
FIG. 8 is a perspective view of an exemplary femoral alignment guide according to the present teachings, shown next to a corresponding anatomic femur.
Figure 9A:
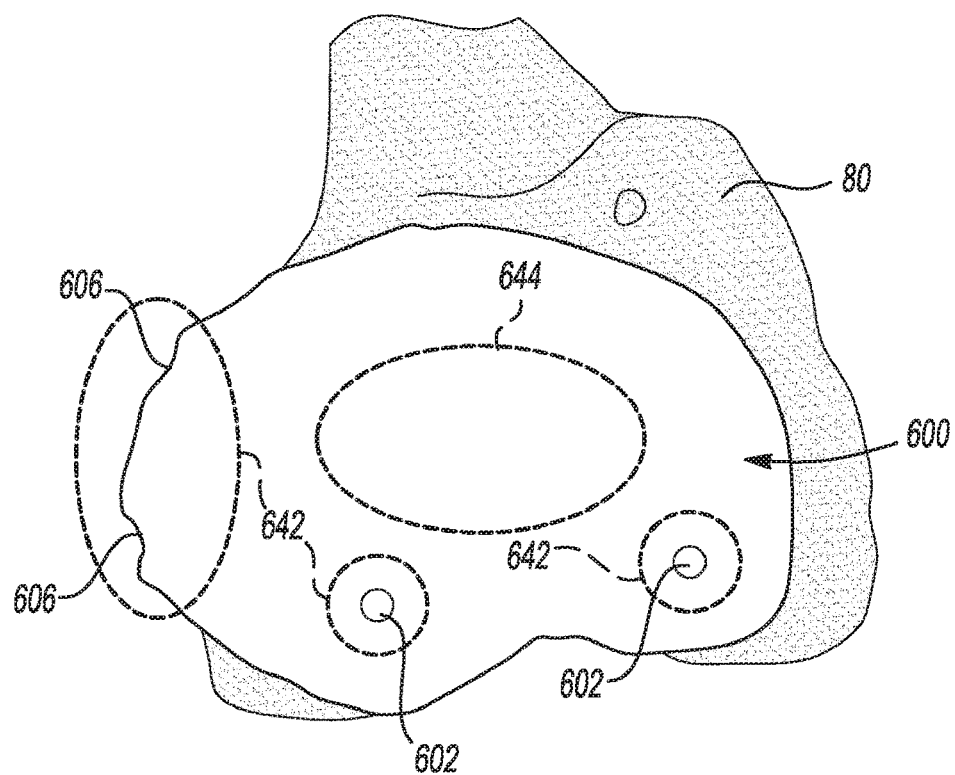
FIGS. 9A and 9B are perspective views of the femoral alignment guide of FIG. 8 shown mounted on the femur.
Figure 9B:
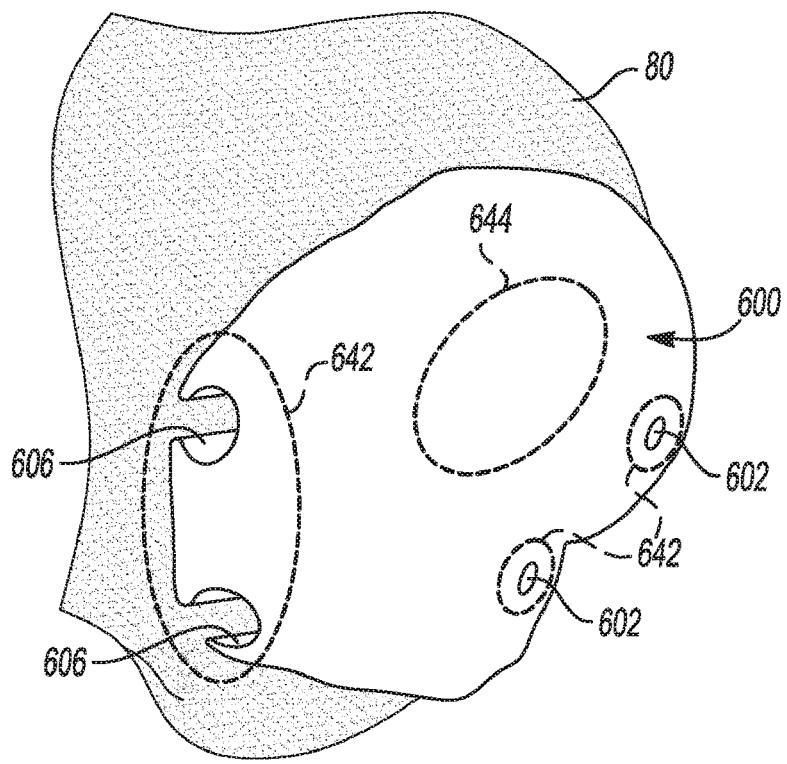

Referring to FIG. 2, an exemplary method for providing the initial implant fitting and alignment is illustrated. The method can be modified or completely replaced according to a surgeon-specific alignment protocol. After the scan data is converted to three dimensional images of the patient anatomy from hip to ankle, images of the tibial and femoral components can be manipulated for obtaining patient-specific alignment by making use of the femoral and tibial mechanical axes 402, 404, illustrated in FIG. 8, and the transepicondylar and cylindrical axes 406, 408, illustrated in FIG. 4. Images of the knee joint anatomy can include images of the joint surfaces of the distal femur and proximal tibial with or without the associated soft tissues, such as articular cartilage, on the respective bone surfaces.

Generally, the femoral mechanical axis is defined as the line joining the center of the femoral head and the center of the intercondylar notch. The femoral anatomic axis is defined as the line along the center of the femoral shaft. The tibial mechanical axis is the line joining the center of the tibial plateau to the center of the tibial plafond or the center of the distal end of the tibia. The tibial anatomic axis is the line along the center of the tibial shaft. The transepicondylar axis is the line connecting the most prominent points of the epicondyles. The cylindrical axis is the line connecting the centers of the condyles when the condyles are approximated by coaxial cylinders. A detailed discussion of the various joint-related axes and the relation of the transepicondylar axis 406 and cylindrical axis 408 is provided in Eckhoff et al, *Three-Dimensional Mechanics, Kinematics, and Morphology of the Knee Viewed in Virtual Reality*, J Bone Joint Surg Am. 87:71-80, 2005, which is incorporated herein by reference.

Figure 5:
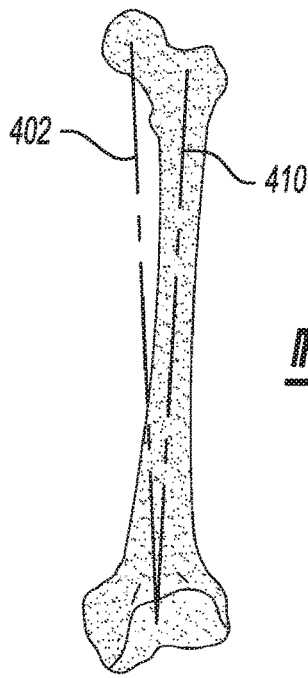
FIG. 5 is a view illustrating the mechanical and anatomic axes in a patient's femoral image.

The relation of the femoral mechanical axis 402 to the anatomic axis 410 for the femur is illustrated in FIG. 5. The femoral and tibial mechanical axes 402, 404 may or may not coincide, as illustrated in FIG. 3. In the following discussion, reference is made to a single mechanical axis 401 encompassing the femoral and tibial mechanical axes 402, 404. The alignment procedure illustrated in FIG. 2 makes use of the mechanical, anatomic, transepicondylar and cylindrical axes in various degrees. The present teachings, however, are not limited to this alignment procedure. Multiple alignment procedures can be provided to accommodate the experience and preference of individual surgeons. For example, the alignment procedure can be based on the anatomic and mechanical axes, or can be substantially based on the cylindrical axis. Further, the alignment procedure can be deformity-specific, such that is adapted, for example, to a valgus or varus deformity.

With continued reference to FIGS. 2-5 and 7, in the image space, the tibial component 504 can be aligned 90° to the mechanical axis 401, at aspect 90. In the frontal plane, the femoral component 502 can be aligned 90° to the mechanical axis 401, at aspect 100. The femoral component 502 can be positioned for "x" mm distal resection, at 110, where "x" can be about 9 mm or as other measurement as indicated for a specific patient. The femoral component 502 can be rotated until its distal surfaces are at 90° to the distal femoral bow (component flexion/extension), at 120. The femoral component 502 can be moved anteriorly/posteriorly until the posterior medial condyle resection is greater or equal to "x" mm, at aspect 130.

The femoral component size can be determined by observing the anterior resection relative to anterior cortex, at 140. If the femoral size is adjusted, the new size can be positioned at the same location relative to the distal and posterior cut planes.

The cylindrical axis 408 of the femur can be located, at aspect 150. The tibia can be flexed 90° relative to the femur about the cylindrical axis 408, at aspect 160. The femoral component 502 can be rotated about the medial condyle until a rectangular flexion space is achieved, at aspect 170. Alternatively, the rotation can be relative to the transepicondylar axis, anterior/posterior axis, and posterior condylar axis, or a combination of all four axes. The femoral component 502 can be centered or lateralized on the femur, at aspect 180. The location for various distal holes for locating the femoral resection block can be also determined.

Referring to FIGS. 6, and 8-15B, an exemplary alignment guide 600 and method of use is illustrated in connection with the patient's femur 80. Reference numbers 200-250 relate to aspects of the method of FIG. 6 and are described in connection with the instruments shown in FIGS. 8-15B for the femur 80.

The alignment guide 600 includes an inner guide surface 640 designed to closely conform, mate and match the femoral joint surface 82 of the patient in three-dimensional space such that the alignment guide 600 and the femoral joint surface are in a nesting relationship to one another. Accordingly, the alignment guide 600 can conform, mate and snap on or "lock" onto the distal surface of the femur 80 in a unique position determined in the final surgical plan, at 200. The alignment guide 600 can have variable thickness. In general, the alignment guide 600 can be made as thin as possible while maintaining structural stiffness. For example, certain areas around and adjacent various securing or guiding apertures 602, 606 can be thickened to provide structural support for guiding a drill or for holding a drill guide or supporting other tools or devices. Exemplary thickened areas 642 are indicated with dotted lines in FIGS. 9A and 9B. Other areas can be cut out for viewing the underlying bone or cartilage of femoral joint surface 82. Viewing areas 644 are indicated with dotted lines in FIGS. 9A and 9B.

Figure 10A:
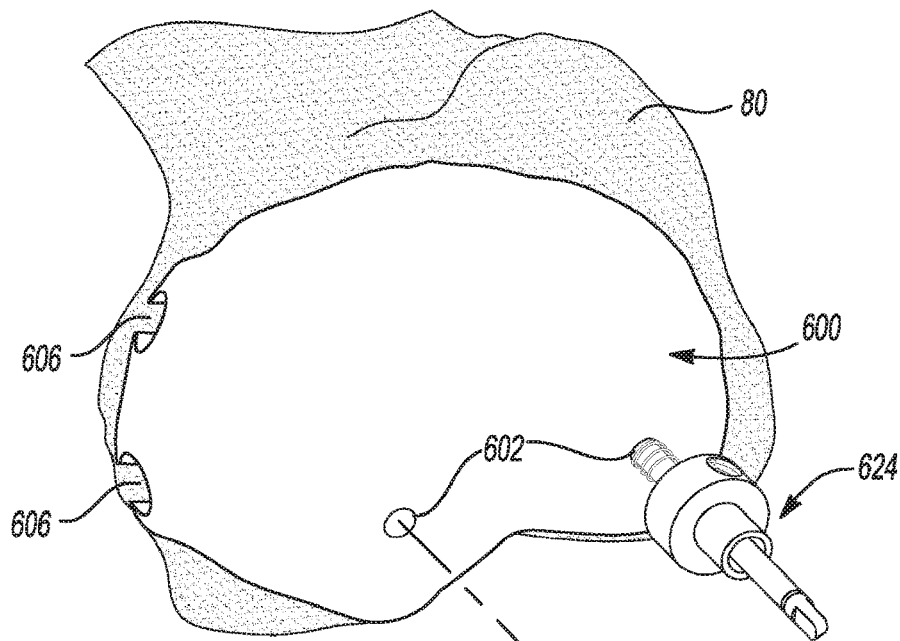
FIGS. 10A and 10B are perspective views of the femoral alignment guide of FIG. 8 shown with spring pins securing the alignment guide to the femur.
Figure 10B:
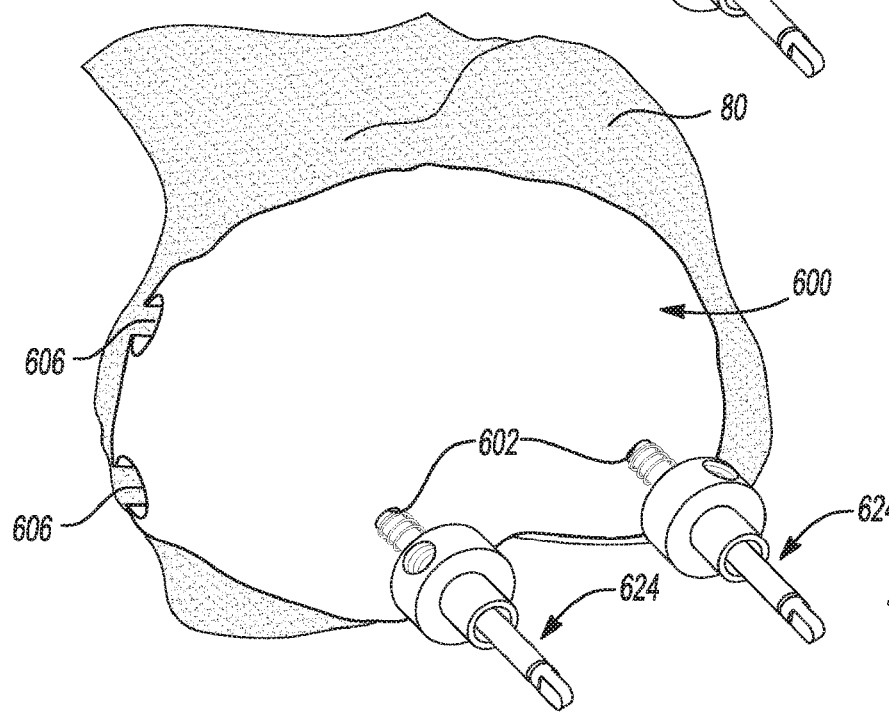
Figure 13A:
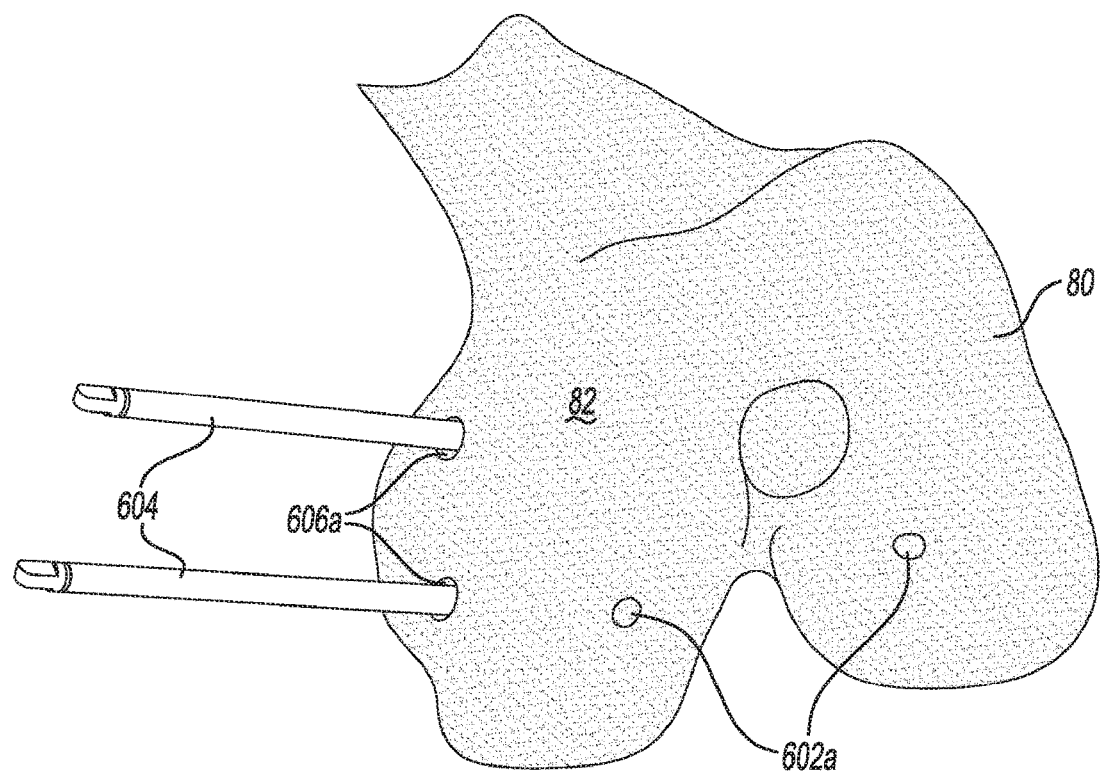
FIG. 13A is a perspective view of FIG. 12B illustrating the guide pins after the removal of the femoral alignment guide.
Figure 13B:
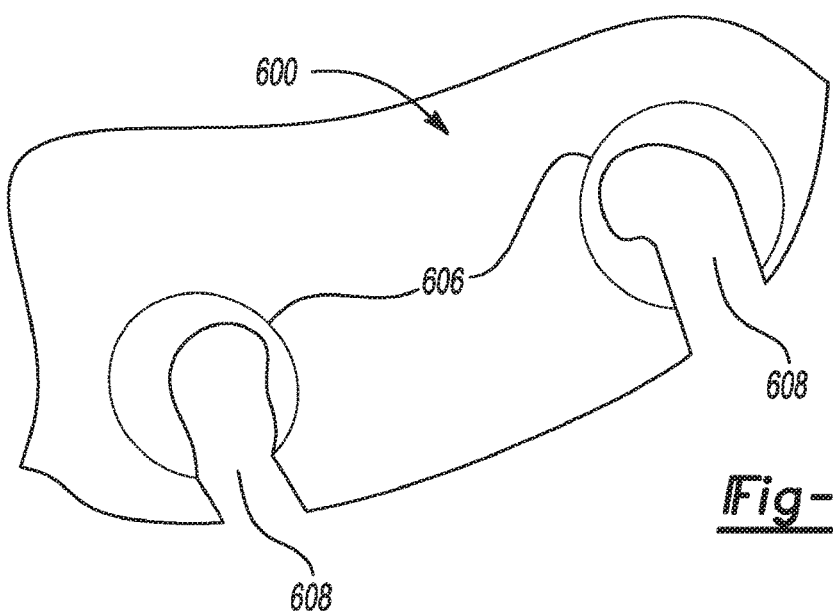
FIG. 13B illustrates a detail of the femoral alignment guide of FIG. 12B.

Referring to FIGS. 10A and 10B, the alignment guide 600 can be secured to the femoral joint surface 82 with fixation members or fasteners 624, such as, for example, spring pins, or other securing fasteners that are received through distal apertures 602 of the alignment guide 600. Locating holes 602a corresponding to the apertures 602 of the alignment guide 600 can be drilled in the distal femur 80 to locate a femoral resection block or other cutting device 620, such as a 4-in-1 cutting block, at 220. The alignment guide 600 can also include guiding apertures 606. Guiding apertures 606 are shown in the anterior-medial side relative to the femur 80, but can also be made in the anterior side of the femur 80 or in other locations and orientations. The guiding apertures 606 can be counter-bored and have a partially open portion 608 in their perimeter for sliding the alignment guide off pins or other fasteners without removing such fasteners, as shown in FIG. 13A and discussed below.

Referring to FIGS. 11A and 11B, a drill guide 700 can be placed in alignment with the guiding apertures 606. The drill guide 700 can include a body 702 having guiding bores 704 corresponding to the guiding apertures 606. The guiding bores 704 can have portions 706 that extend beyond the body 702 and into the guiding apertures 606 for facilitating alignment. The drill guide 700 can also include a handle 710 extending sideways from the body 702 and clear from the drilling path.

Figure 6:
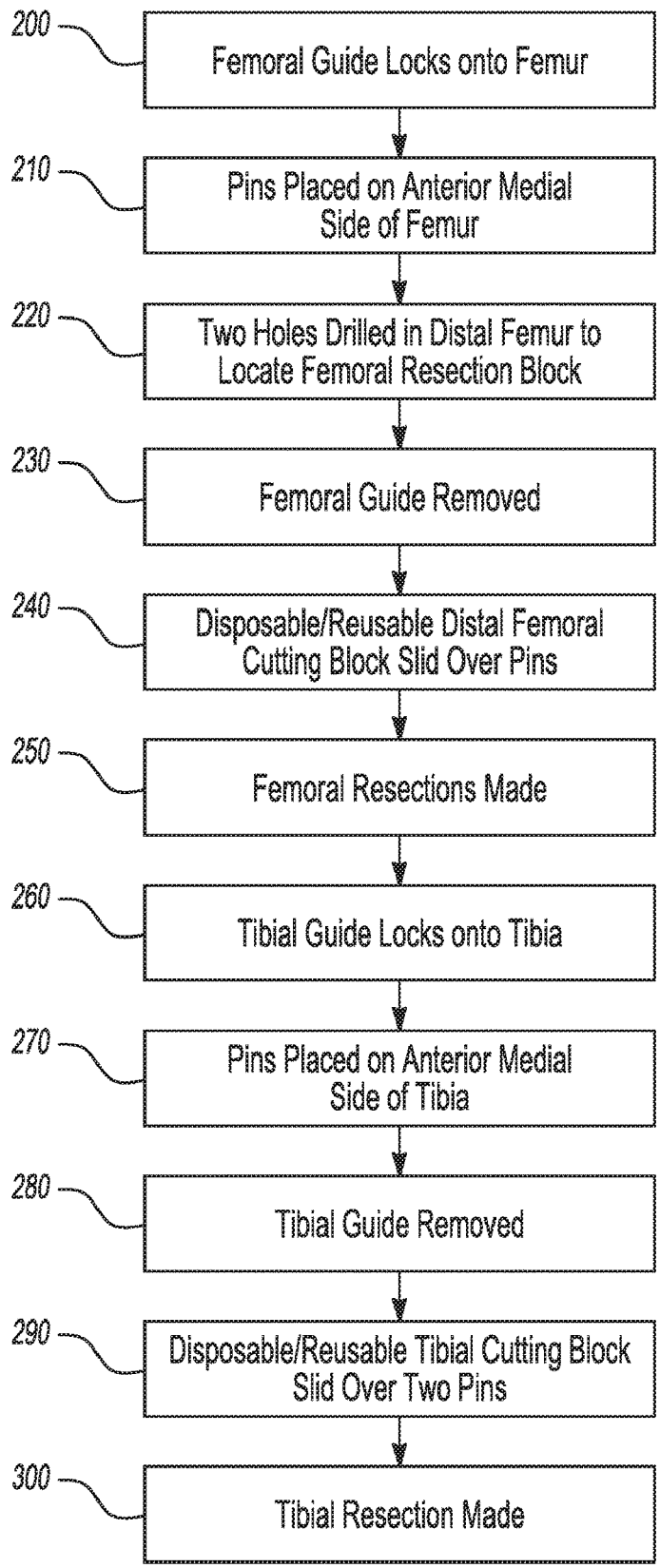
FIG. 6 is a flowchart of an exemplary method of using patient specific alignment guides according to the present teachings.

Referring to FIG. 11C, guide elements 604, such as pins or other fasteners, for example, can be drilled through the guiding bores 704 of the drill guide 700 on the anterior or anterior-medial side of the femur 80, at aspect 210 of the method of FIG. 6. The guide elements 604 can be parallel or at other angles relative to another. The guide elements 604 can define a plane that is parallel to a distal resection plane for the femur.

Figure 12A:
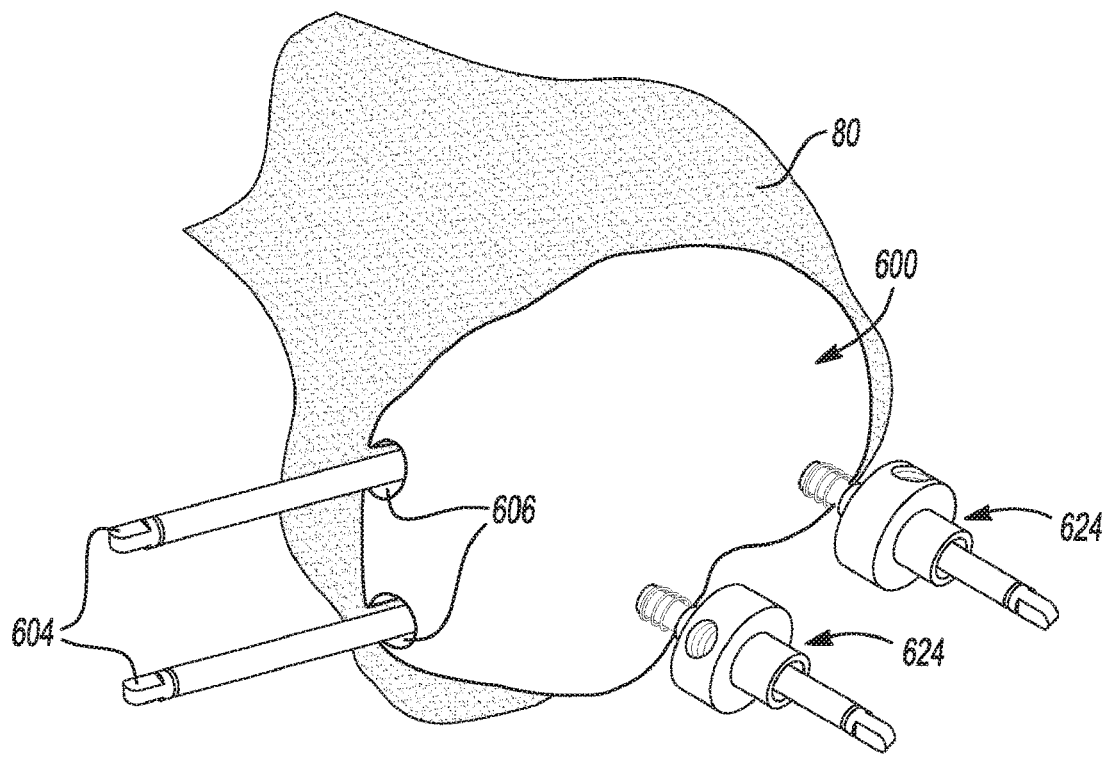
FIG. 12A is a perspective view of the femoral alignment guide of FIG. 11C shown after the removal of the drill guide.
Figure 12B:
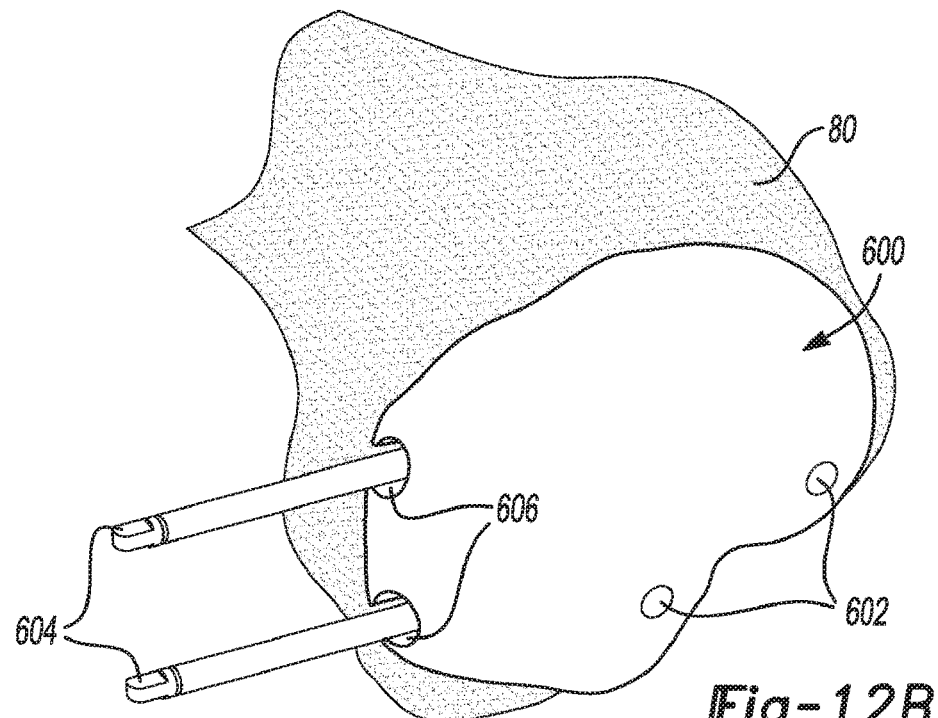
FIG. 12B is a perspective view of the femoral alignment guide of FIG. 12A shown after the removal of the spring pins.

Referring to FIG. 12A, the drill guide 700 can be removed. Referring to FIGS. 12B-13B, the fasteners 624 can be removed, and the alignment guide 600 can be removed from the femur 80 by sliding the alignment guide 600 off the guide elements 604 through the open portions 608 of the guiding apertures 606 without removing the guide elements 604 at the anterior/medial corner of the knee, at aspect 230 of FIG. 6.

The guide elements 604 can be used to prepare the joint surfaces for the prosthesis by mounting cutting guides/blocks for resecting the joint surface. Alternatively, a robotic arm or other automated, guided or computer controlled device that can guide the resections based on the pre-operative surgical plan can be mounted on the guide elements 604 and assist the surgeon in preparing the joint surface for the prosthesis.

Figure 14A:
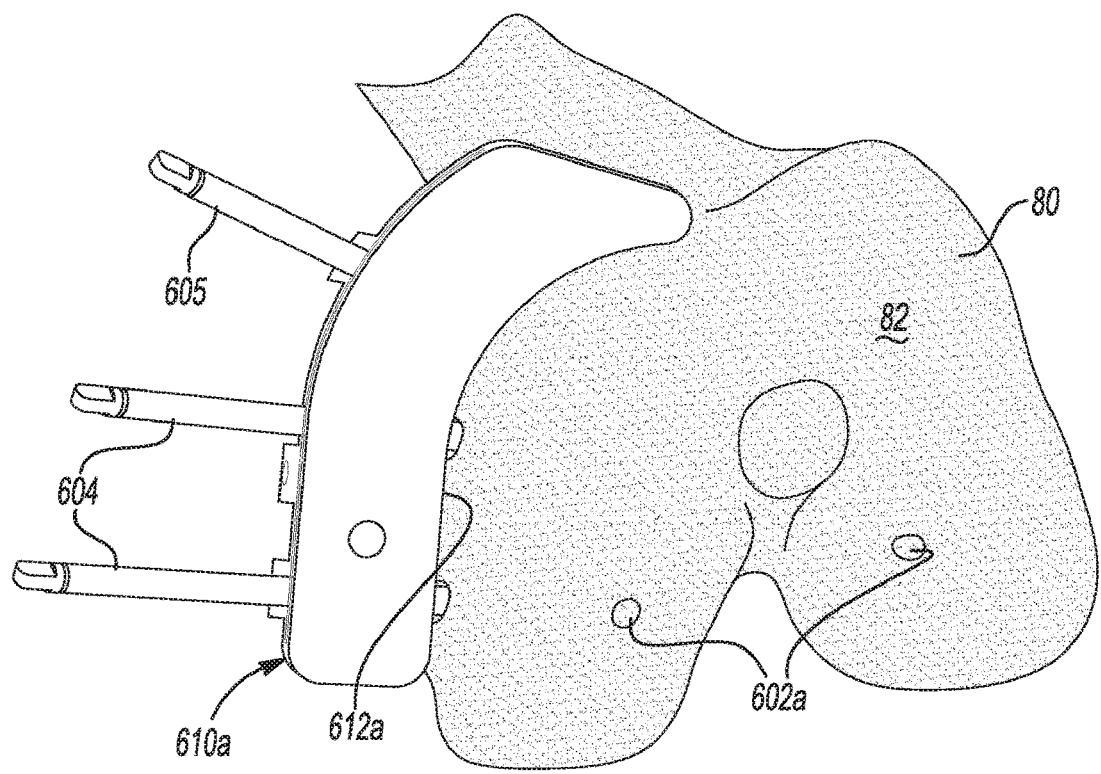
FIG. 14A is a perspective view of a distal femoral cutting block shown over two pins on a patient's femur, according to the present teachings.
Figure 14B:
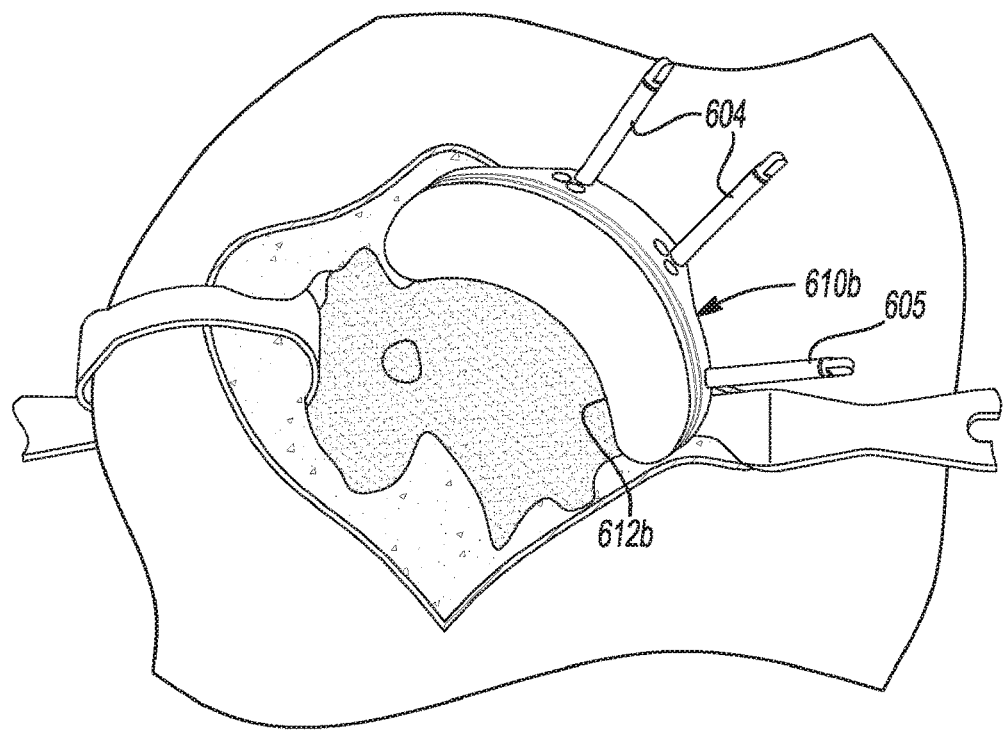
FIG. 14B is a perspective view of a distal femoral cutting block shown over two guide pins on a patient's femur, according to the present teachings.

Referring to FIGS. 14A and 14B, exemplary distal cutting blocks 610a, 610b that can be mounted over the guide element 604 for making the distal resection, at aspect 640 of FIG. 6, are illustrated. A third fixation element 605, obliquely oriented relative to the guide elements 604 can also be used. The distal cutting blocks 610a, 610b can have an inner surface 612a, 612b that generally follows the shape of the femur 80 to a lesser or greater degree. The distal cutting blocks 610a, 610b can be disposable or re-usable.

Figure 15A:
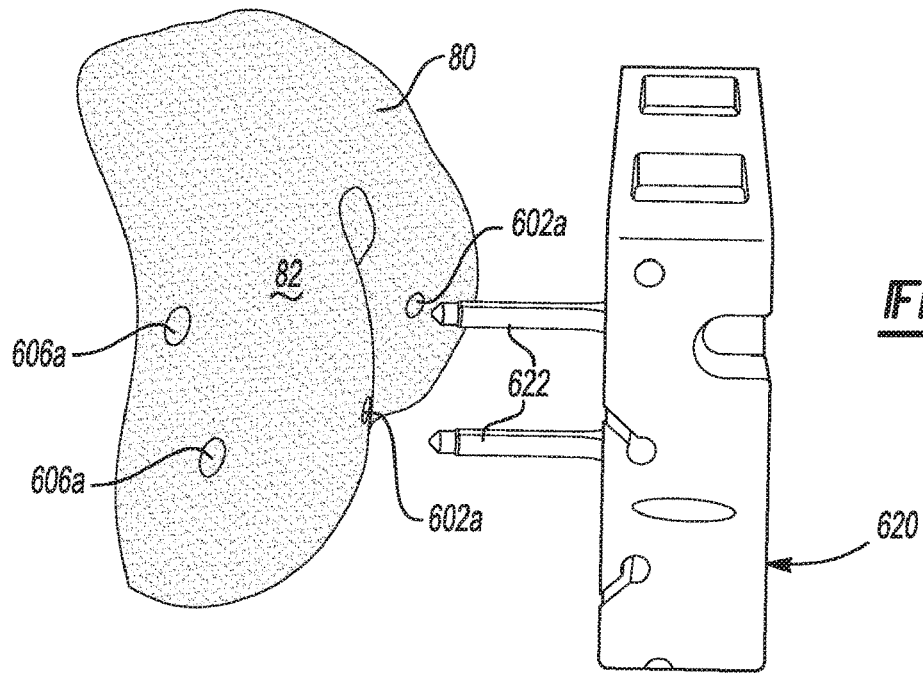
FIG. 15A is a perspective view of an exemplary 4-in-1 cutting block positioned on the femur with reference to holes corresponding to the spring pins.
Figure 15B:
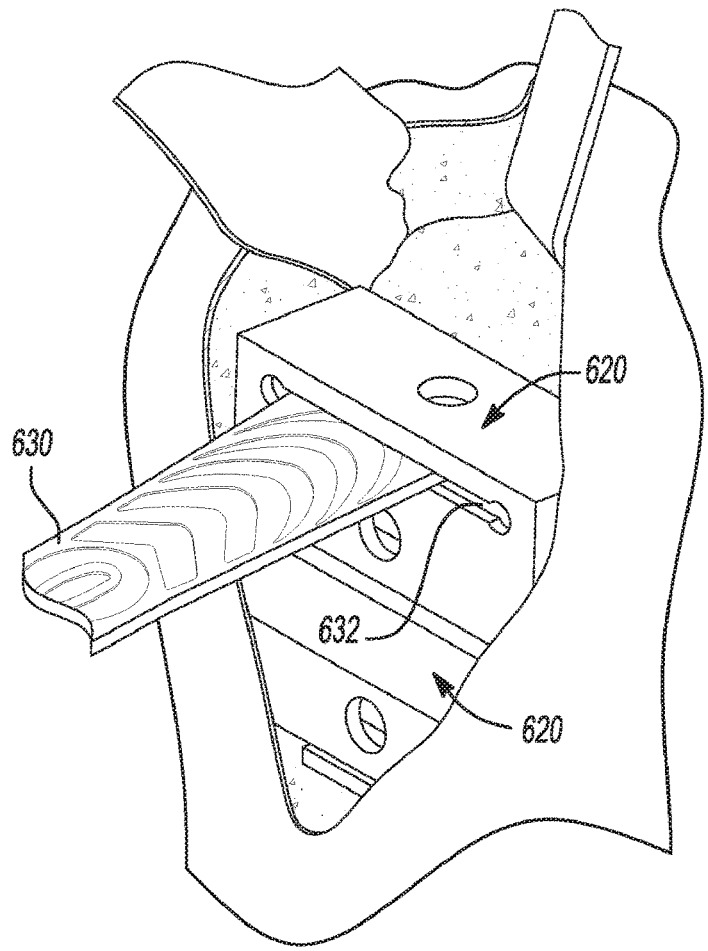
FIG. 15B a perspective view of the cutting block of FIG. 15A shown with a cutting blade.

Referring to FIGS. 15A and 15B, after the distal resections are made with the distal cutting block 610a or 610b, the femoral resection block 620 can be mounted with pegs or other supporting elements 622 into the holes 602a corresponding to the fasteners 624. The femoral resections can be made using, for example, a cutting blade 630 through slots 632 of the femoral resection block 620, at aspect 250 of FIG. 6.

Referring to FIGS. 6 and 16A-D, an exemplary alignment guide 600 is illustrated in connection with the patient's tibia 81. Reference numbers 260-300 relate to aspects of the method of FIG. 6 and are described in connection with the instruments shown in FIGS. 16A-16D for the tibia.

Figure 16A:
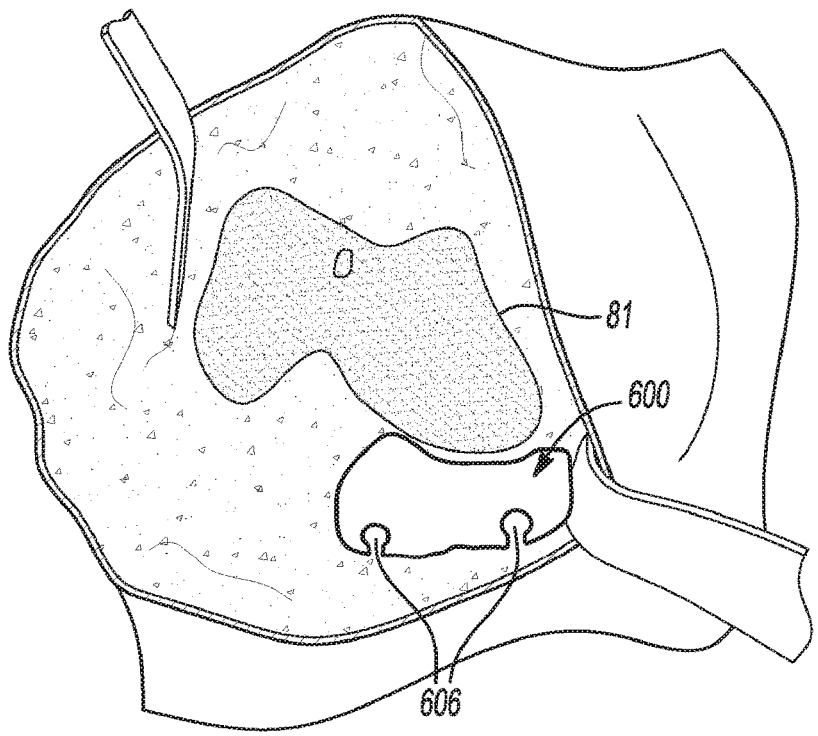
FIG. 16A is a perspective view of a tibial alignment guide according to the present teachings, shown mounted on the tibia.
Figure 16B:
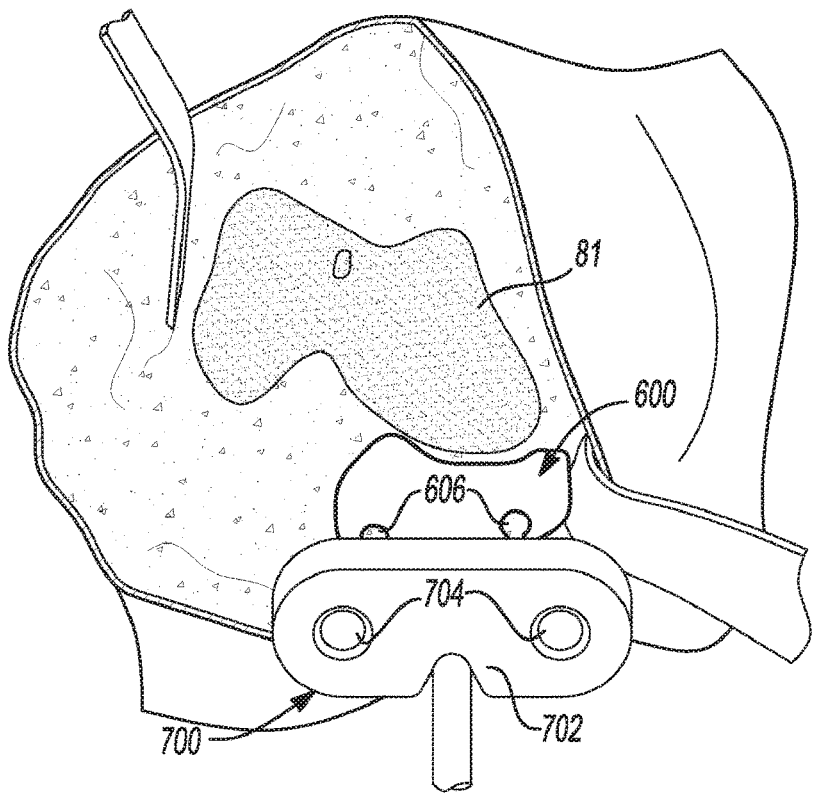
FIG. 16B is a perspective view of the tibial alignment guide of FIG. 16A shown with a drill guide.
Figure 16C:
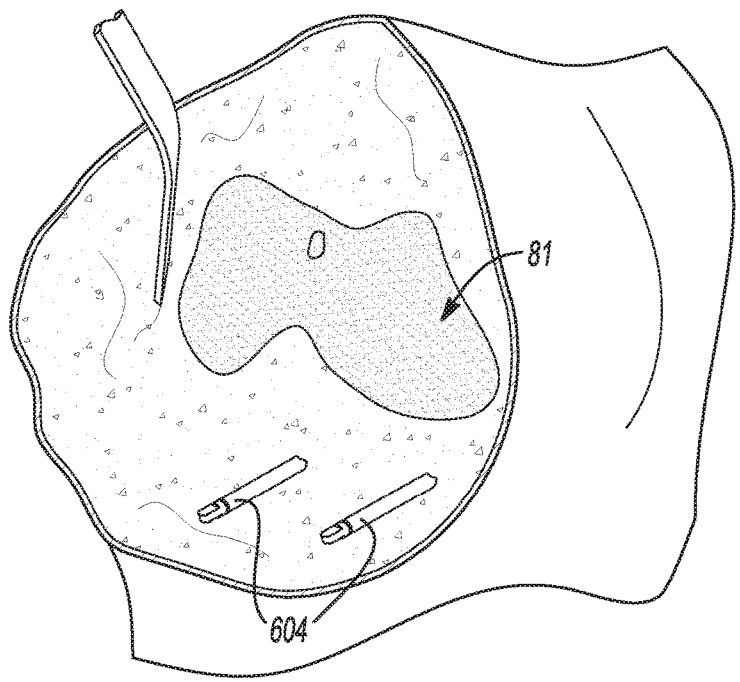
FIG. 16C is a perspective view of FIG. 16B illustrating the guide pins after the removal of the tibial alignment guide.
Figure 16D:
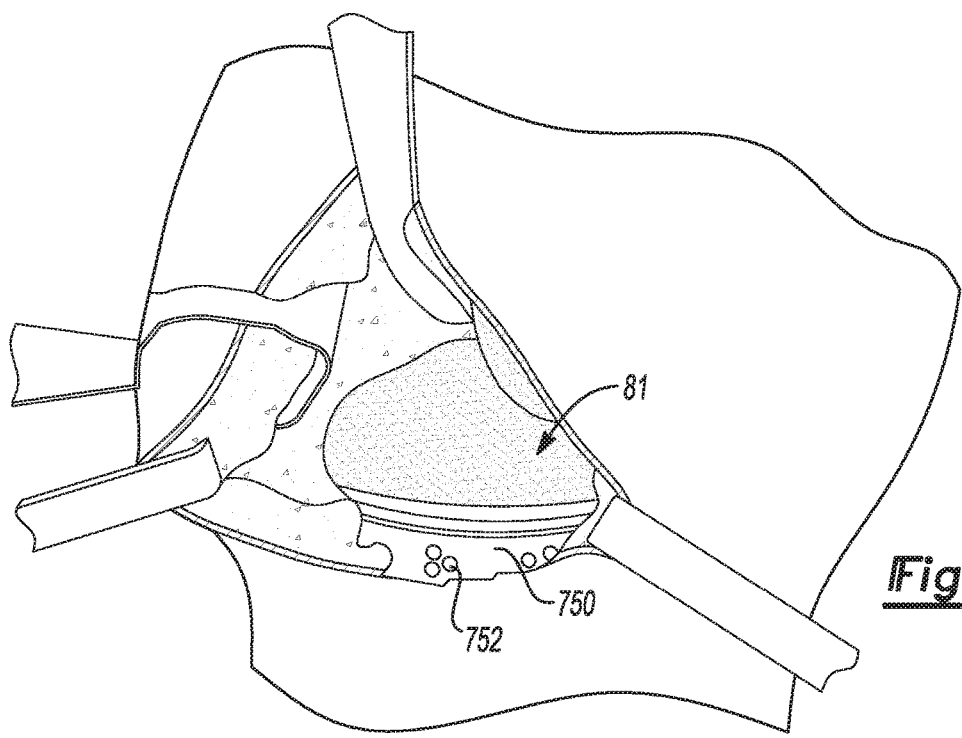
FIG. 16D is a perspective view of FIG. 160 illustrating a tibial cutting guide mounted on the guide pins.

The alignment guide 600 can conform, nestingly mate in three-dimensional space and snap on or "lock" by design onto the tibia 81 in a unique position, at aspect 260 of FIG. 6. The alignment guide 600 can wrap around the anterior-medial edge of the tibia 81, as shown in FIG. 16A. The drill guide 700 can be aligned with the counter-bored guiding apertures 606 of the alignment guide 600, as shown in FIG. 16B. Two or more guide elements 604 can be placed on the anterior medial side of the tibia, at aspect 270 of FIG. 6. An additional fixation element can also be used for additional securing for the alignment guide 600. The drill guide 700 and the alignment guide 600 can be removed, leaving behind the guide elements 604 attached, at aspect 280 of FIG. 6, and as shown in FIG. 16C. A disposable or reusable tibial cutting block 750 can be slid over the guide elements 604, at aspect 290 of FIG. 6, and as shown in FIG. 16O. The tibial cutting block 750 can include a series of holes 752, allowing the cutting block 750 to be translated proximally or distally to adjust the level of the distal resection. The tibial resection can be made, at 300.

The present teachings provide patient-specific alignment guides that can be used for alignment in orthopedic surgery. Each alignment guide includes an inner surface that nestingly mates and conforms in three-dimensional space with a corresponding joint surface of a specific patient. The alignment guides can be used for locating guide elements on the joint surface. After the alignment guides are removed, cutting guides or other cutting devices, including automated or robotic devices, can be mounted on the guide elements for making various resection cuts. Because the alignment guides are not used for cutting, the alignment guides do not require substantive thickness to extend anteriorly, and consequently have a lower profile, and less weight. Additionally, because the alignment guides are removed before cutting, the present teachings provide increased ability to visualize the cuts and the cutting process.

Subchondral Access

Figure 17:
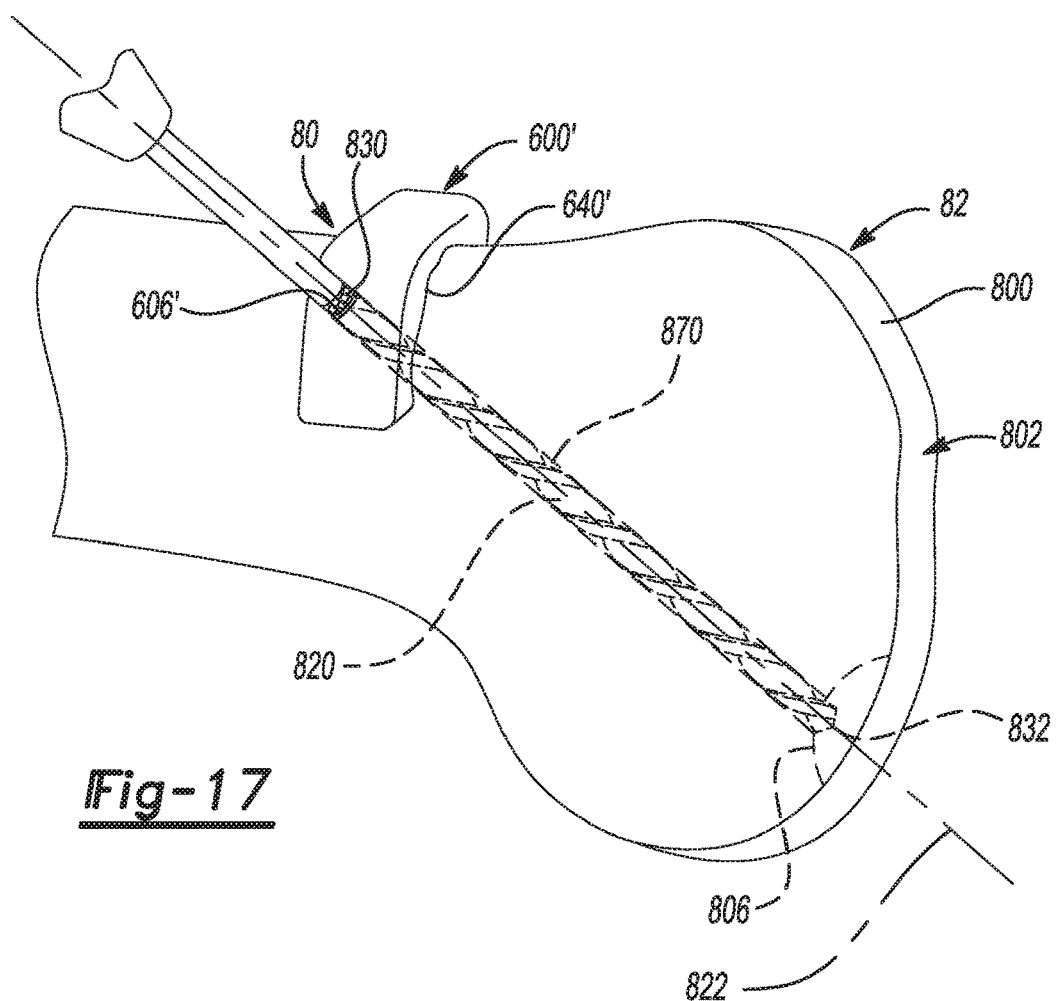
FIG. 17 is a perspective environmental view of a distal femur with a guide positioned thereon and an instrument forming a bore in the femur.

According to various embodiments, the guide 600 or any appropriate guide member, including the guide 600' illustrated in FIG. 17, can be positioned relative to a bone, such as the femur 80, for performing a procedure relative to the bone. For example, as illustrated in FIG. 17, the guide 600' can be positioned relative to the femur 80 to guide a drilling member, such as a drill bit or pin 820, to obtain access to an interior portion of the femur 80 that is beneath a surface of the femur. Once access is obtained to a portion of the femur, such as below the surface of a femur, a procedure can be performed on the femur for various purposes. For example, the procedure can include a tumor resection, a bone filling, and/or a bone replacement.

According to various procedures, a portion of bone that is beneath a condyle, also referred to as subchondral, can be repaired or replaced with a bone void filling material, such as in a procedure generally disclosed using Subchondroplasty® instruments and/or access devices that are provided by Knee Creations LLC, having a place of business in Westchester, Pa., USA and/or Subchondroplasty Orthopedics LLC having a place of business in Westchester, Pa., USA. The Subchondroplasty instruments are known to assist in obtaining access to an area of a bone that is beneath a condyle to perform a procedure interior to the bone to assist in maintaining the condyle region, including a condylar cartilage. For example, a subchondular bone can be reinforced or strengthened with a selected material to strengthen the bone and to reinforce and strengthen support of the condylar cartilage. Appropriate materials can be biomimetic bone substitute material that can be used to strengthen and/or cause replacement of subchondular bone.

Regions that may need to be strengthened include bone marrow lesions that form and may weaken support of the condylar cartilage. Accordingly, the appropriate bone substitute materials can be placed in or around the bone marrow lesions to cause regeneration of the bone and strengthening thereof. Appropriate bone substitute materials can include Accufill® bone void filler that includes injectable calcium phosphate, provided by Knee Creations, LLC having a place of business in New York, N.Y., USA. According to various embodiments, bone void filler materials, including calcium phosphate, can be placed in a bone defect to cause regrowth and/or remineralization of a selected bone region.

It is also understood that the guide 600 can be used to place an instrument, such as the guide elements 604, through one or more guiding apertures 606 to position the instrument at an appropriate and selected location within the bone. For example, as discussed above, the guide 600 can be designed to include the inner guide surface 640 that closely conforms or matches a femoral joint surface 82. The inner guide surface 640 is generally or specifically a three-dimensional curved inner surface that is preoperatively configured from medical image scans of the patient, such as a knee joint of the patient, to nestingly conform and mate and match only in one position to a corresponding three-dimensional femoral surface of the patient. The guiding apertures 606, therefore, are positioned at a selected, known, and specific location relative to the femur 80. The design of the inner guide surface 640 and the placement of the guiding aperture 606 may assist in a guiding and insuring guiding of any appropriate instrument relative to an interior portion of the bone, including the femur 80. The apertures 606' can define a patient specific axis, as discussed herein, to guide an instrument to form a patient specific hole or bore and to a patient specific location. Thus, any appropriate procedure can be performed at an interior of the bone. Appropriate procedures can further include removing a tumor within the bone, removing necrotic tissue within the bone, positioning a bone-growing implant, positioning a supporting device within the bone, or other appropriate procedure.

It is understood that the guide 600, or any appropriate guide, can be designed to mate with a surface of any appropriate bone portion including a distal femoral bone portion surface, a distal anterior femoral bone surface, a vertebral bone surface, a proximal tibial bone surface, or any other appropriate bone surface. Further, a procedure can be performed with the guide 600, according to various embodiments to assist in fixation of bone, implanting an implant transverse through a fracture, tumor removal, bone surface supporting implant or device, or other appropriate procedure.

With reference to FIG. 1, scan data can be generated or obtained at aspect 10. The scan data can include various image data of a patient including MRI scan data and CT scan data. The scan data can be used to generate an initial surgical plan at aspect 30 which is finalized at aspect 40 to design patient-specific guides at aspect 50. The patient specific guides are then made, including being machined, at aspect 70 and are then shipped to a surgeon at aspect 79. The plan that is finalized by the surgeon at aspect 40 can be based upon various diagnoses of a patient. For example, a diagnosis of a bone loss, tumor, fracture, and the like can be made based upon the scan data of the patient. The finalized plan can include placement and/or orientation of a guiding aperture 606' in the guide 600' such that instruments are guided to selected and known diagnosed regions of the patient. It will be understood that although the following discussion relates generally to a subchondrol weakening or lesion relative to a distal femur in a knee joint, any diagnosis can be made and that the guide 600' can be designed, according to method illustrated in FIG. 1, to allow for positioning of an instrument relative to the diagnosed region.

Figure 17A:
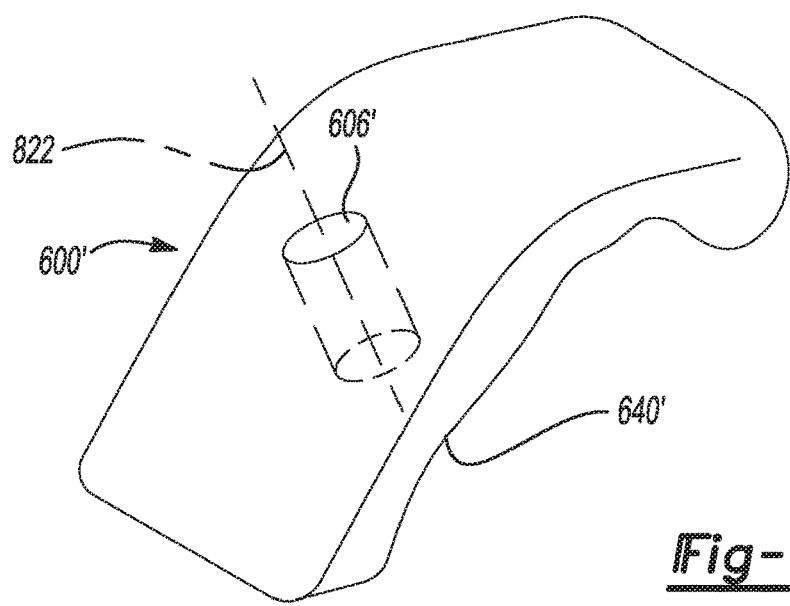
FIG. 17A is a perspective view of the guide of FIG. 17.

Turning reference to FIGS. 17 and 17A, the femur 80 is schematically illustrated. The femur 80 can be illustrated as image data on a display device, such as a computer display device. The FIG. 17 illustrating the femur 80 can represent a natural femur and/or image data or a conversion of image data into a three-dimensional display for viewing by a user and/or operator, including a surgeon. The femur 80 can include the condylar cartilage 800 that can extend over at least a portion of the femur 80 including a condylar region 802 that can define at least a portion of the femoral joint surface 82. Other portions of the femur 80 may not include cartilage, such as medial and/or anterior regions of the femur 80. As illustrated and discussed above, the femoral joint surface 82 can form at least a portion of the knee joint where the femur can articulate with a proximal portion of the tibia 81. Near the condyle 82 and generally below the condylar cartilage 800, a bone lesion and/or weakened bone region 806 can be viewed (i.e. seen in the scan data of the patient) and/or diagnosed. The weakened bone region 806 can be diagnosed or viewed based upon generally known techniques, including viewing the scans, e.g. MRI and CT scans, of the patient and/or a conversion or reconstruction of the scanned data by one skilled in the art. It will be understood that the weakened bone region 806 can be representative of any appropriate diagnosis, including diagnosis of a tumor, fracture, bone marrow lesions, or other bone defect or area for performing a procedure.

Once the weakened bone region 806 is diagnosed in the femur 800, the method illustrated in FIG. 1 can be used to design a patient-specific guide at aspect 50, machine and sterilize the patient-specific guide at aspect 70, and ship the guide to the surgeon at aspect 79. The patient-specific guide 600' can include an inner patient specific surface 640' to contact a selected portion of a surface of the femur 80. It is understood that the guide 600' can be designed to contact a medial, lateral, anterior, anterior medial, anterior lateral, or any appropriate portion of the bone. The patient specific guide 600' and the inner surface 640' can be similar to the guide 600 and inner surface 640 discussed above in that the guide can contact, nest, and/or lock to a specific portion of the anatomy to align the patient specific guiding aperture 606' relative to a specific region, such as the weakened region 806.

As exemplarily illustrated in FIG. 17, an anterior-medial positioning of a patient-specific guide 600' is illustrated. The guide 600' may include one or more of the guide apertures 606' that can be formed through the guide 600'. An instrument, including the guide member 604, the drill 820, or other appropriate member can be positioned through the aperture 606' to form a portal or bore 870 into the femur 80. The bore 870 may be a blind bore that terminates away from the cartilage 800 such that a port or hole is not formed into or through the cartilage 800. Thus, the bore 870 will generally extend only through the bone material and the bore forming instrument need not contact or engage the cartilage 800.

The drill bit 820 can be passed through the guide 600', such as through the guide aperture 606', to engage the femur 800 and drill to the weakened bone region 806. The positioning of the guide 600' and the guiding aperture 606' can be such that the drill 820 will proceed along a patient specific axis 822 through the femur 800 and to the weakened bone region 806. Based upon the scan data from aspect 10 of FIG. 1 and the plan at aspect 40 a patient specific mark can also be placed on the drill bit 820, including a visible demarcation 830, such that the surgeon knows when the drill bit 820, including a tip 832, has moved an appropriate amount into the femur 80. The appropriate amount can include the tip 832 being positioned at the weakened bone region 806. The surgeon may then stop progressing the drill 820 into the femur 80 and perform a procedure through the bore 870 at a patient specific depth.

Once the drill bit 820 has been positioned such that at least the tip 832 has reached the weakened bond region 806, a procedure can occur relative to the femur 80 and the weakened bone region 806. According to various embodiments, a material may be delivered to the weakened bone region 806, such as a bone void filling material, other pharmaceutical, steroid, demineralized bone, or other appropriate material. According to various embodiments, the drill bit 820 can be cannulated such that a material can be delivered through the drill bit 820 directly to the weakened bone region 806. According to various embodiments, however, the drill bit 820 can be removed and a syringe 860 can be moved relative to the femur 80.

Figure 18:
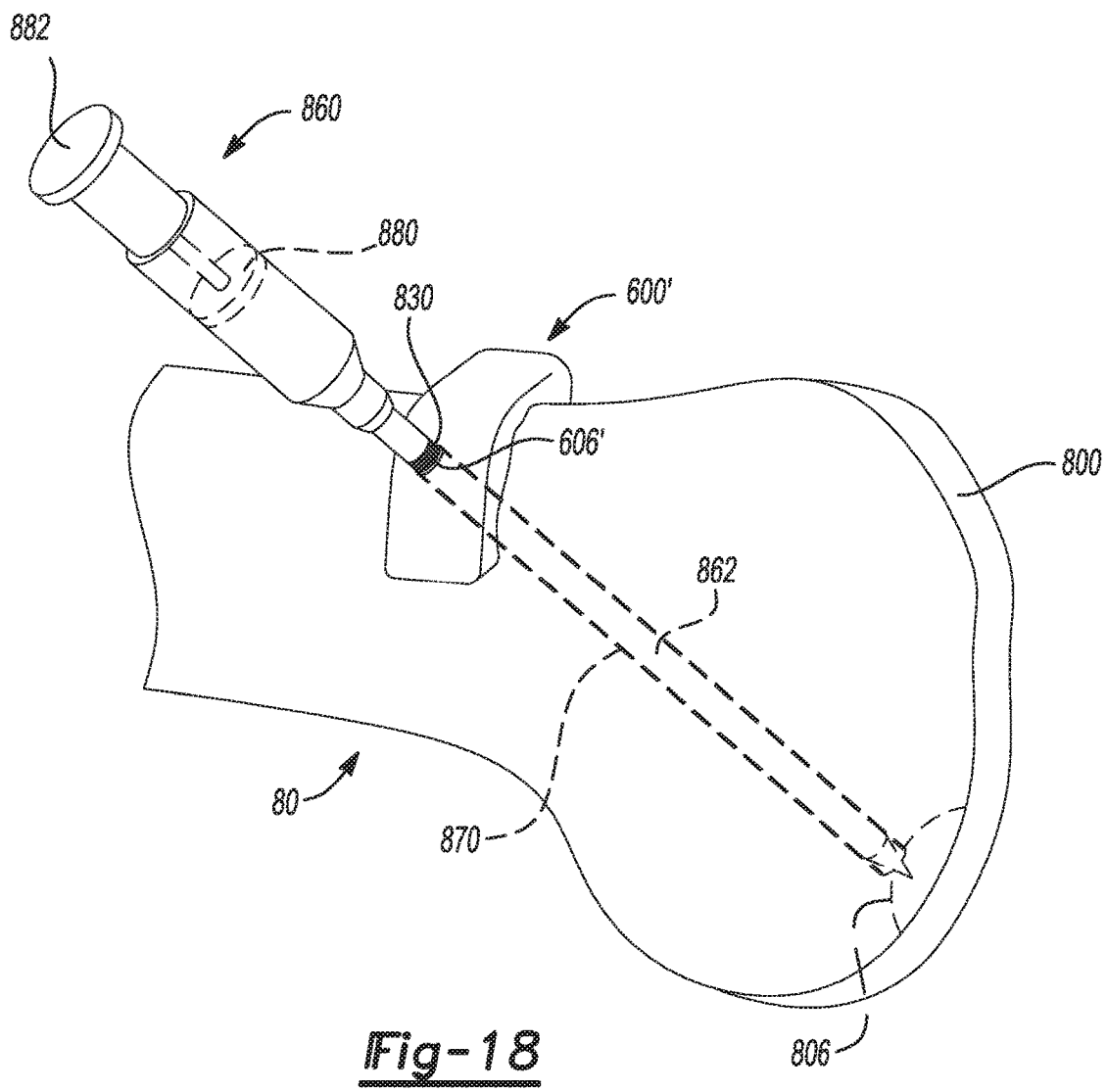
FIG. 18 is an environmental view of a distal femur with a guide positioned thereon and an instrument position in a bore through the guide.

With reference to FIG. 18, the syringe 860 can be positioned relative to the femur 80 such that at least a needle or cannulated member 862 is positioned through the bore 870 that is formed within the femur 80 by the drill bit 820. The bore 870 remains in the femur 80 after the drill bit 820 is withdrawn. The bore 870 is generally a blind bore such that it terminates beneath an external surface of the femur 80. Accordingly, the blind bore 870 does not extend to a surface of the cartilage 800 nor does the drill bit 820 penetrate or contact the cartilage 800. Thus, the cannulated member 862 of the syringe 860 will also not penetrate or contact cartilage 800 during a selected procedure. The bore 870 may also originate at a cartilage free region of the femur 80, or any appropriate bone. A barrel or reservoir 880 can be filled with the selected material that can be ejected through the cannulated member 862 by a plunger mechanism or other pump mechanism 882. A selected treatment, such as a bone void filling material can then be injected into the bone region 806 from the syringe 860.

It is understood, however, that other instruments can be passed through the bore 870 to the weakened bone region 806. Again, the weakened bone region 806 may represent any bone or anatomical feature for which a procedure is appropriate. For example, as discussed above, the weakened bone region 806 can relate to a tumor within the bone, such as within the femur 80. Accordingly, an excising instrument may pass through the bore 870 to the weakened bone region 806 and a biopsy, excision, or other procedure can occur. For example, a biopsy can be obtained of the material within the weakened bone region 806 for a further diagnosis, such as confirmation of a cancerous growth or other growth.

Regardless of the diagnosis of the patient, including the weakened bone region 806, the guide 600' can be designed based upon the plan as illustrated in FIG. 1 to include the guide aperture 606' to guide an instrument relative to a diagnosed region, including the weakened bone region 806. The guiding aperture 606' can allow for guiding an access forming instrument, such as the drill bit 820, and/or a treatment instrument, such as the syringe 860 or a biopsy instrument, as discussed above. The guide 600' can be positioned relative to the femur 80 for various and multiple portions of a procedure to obtain access to a single region for both accessing and/or treating the single region.

The diagnosis region, including the weakened bone region 806 illustrated in FIG. 17, can be accessed due to the patient-specific orientation of the guiding aperture 606' and/or the inner surface 640' of the guide 600' that contacts the femur 80. Accordingly, a procedure can occur that is subchondral and does not engage, contact, or pierce the cartilage 800 of the femur 80. It is understood, in a similar manner, that the guide 600' can be designed to contact any specific bone portion for engaging, treating, or accessing a portion of the bone that is adjacent or near a cartilage or soft tissue portion without contacting or piercing the soft tissue or cartilage portion. Thus, a procedure and/or treatment of the patient can be performed without disturbing the soft tissue, including cartilage, adjacent or on a bone of a patient.

The foregoing discussion discloses and describes merely exemplary arrangements of the present teachings. One skilled in the art will readily recognize from such discussion, and from the accompanying drawings, that various changes, modifications and variations can be made therein without departing from the spirit and scope of the present teachings.

What is claimed is:

1. A femoral alignment guide for preparing a knee joint for a prosthesis in a patient comprising:
   a patient-specific three-dimensional curved inner surface preoperatively configured from medical image scans of the knee joint of the patient to nestingly conform and match with a corresponding three-dimensional femoral surface of a femur of the patient in only one position;
   an exterior surface opposing the inner surface; and
   at least one guide aperture passing through the inner surface and the exterior surface, wherein the at least one guide aperture is configured to form an opening in a perimeter of the femoral alignment guide so as to be only partially surrounded by the femoral alignment guide.

2. The femoral alignment guide of claim 1, further comprising one or more pins configured to be received by the at least one guide aperture and penetrate the femur, wherein the at least one guide aperture is configured to allow for removal of the femoral alignment guide from the femur without removing the one or more pins from the femur.

3. The femoral alignment guide of claim 1, further comprising a distal guide aperture, wherein the femoral alignment guide is configured to position the distal guide aperture at a distal portion of the femoral surface when the femoral alignment guide is positioned on femur.

4. The femoral alignment guide of claim 3, wherein the femoral alignment guide is configured to position the distal guide aperture at one of a distal-lateral portion of a medial condyle and a distal-medial portion of a lateral condyle of the femur.

5. The femoral alignment guide of claim 3, wherein the femoral alignment guide has a thickened area around each of the at least one guide aperture and the distal guide aperture.

6. The femoral alignment guide of claim 1, wherein the femoral alignment guide is configured to position the at least one guide aperture at one of an anterior or anterior-medial portion of the femoral surface when the femoral alignment guide is positioned on the femur.

7. The femoral alignment guide of claim 1, wherein the femoral alignment guide is configured to position the at least one guide aperture at one of a medial portion of a medial condyle and a lateral portion of a lateral condyle of the femur.

8. The femoral alignment guide of claim 1, wherein the three-dimensional curved inner surface of the femoral alignment guide is configured to nestingly conform and match with one or more of articular cartilage covering the femoral surface and a bone portion underlying the femoral surface.

9. A femoral alignment guide for preparing a knee joint for a prosthesis in a patient comprising:
a patient-specific three-dimensional curved inner surface preoperatively configured from medical image scans of the knee joint of the patient to nestingly conform and match with a corresponding three-dimensional femoral surface of a femur of the patient in only one position;
an exterior surface opposing the inner surface;
a first guide aperture passing through the inner surface and the exterior surface, wherein the femoral alignment guide is configured to position the first guide aperture at a distal portion of the femoral surface when the femoral alignment guide is positioned on femur; and
a second guide aperture passing through the inner surface and the exterior surface, wherein the second guide aperture is configured to form an opening in a perimeter of the femoral alignment guide so as to be only partially surrounded by the femoral alignment guide, and wherein the femoral alignment guide is configured to position the second guide aperture at one of an anterior or anterior-medial portion of the femoral surface when the femoral alignment guide is positioned on the femur.

10. The femoral alignment guide of claim 9, further comprising one or more pins configured to be received by the second guide aperture and penetrate the femur, wherein the second guide aperture is configured to allow for removal of the femoral alignment guide from the femur without removing the one or more pins from the femur.

11. The femoral alignment guide of claim 9, wherein the femoral alignment guide is configured to position the first guide aperture at one of a distal-lateral portion of a medial condyle and a distal-medial portion of a lateral condyle of the femur.

12. The femoral alignment guide of claim 9, wherein the femoral alignment guide is configured to position the second guide aperture at one of a medial portion of a medial condyle and a lateral portion of a lateral condyle of the femur.

13. An orthopedic system for preparing a knee joint for a prosthesis in a patient comprising:
a femoral alignment guide, comprising:
a patient-specific three-dimensional curved inner surface preoperatively configured from medical image scans of the knee joint of the patient to nestingly conform and match with a corresponding three-dimensional femoral surface of a femur of the patient in only one position;
an exterior surface opposing the inner surface; and
at least one guide aperture passing through the inner surface and the exterior surface, wherein the at least one guide aperture is configured to form an opening in a perimeter of the femoral alignment guide so as to be only partially surrounded by the femoral alignment guide; and
one or more pins configured to be received by the at least one guide aperture and penetrate the femur, wherein the at least one guide aperture is configured to allow for removal of the femoral alignment guide from the femur without removing the one or more pins from the femur.

14. The orthopedic system of claim 13, further comprising a tibial alignment guide that includes:
a patient-specific three-dimensional inner curved surface preoperatively configured from medical image scans of the knee joint of the patient to nestingly conform and match with a corresponding three-dimensional tibial surface of a tibia of the patient;
first and second tibial guide apertures that are configured to form an opening in a perimeter of the femoral alignment guide so as to be only partially surrounded by the tibial alignment guide.

15. The orthopedic system of claim 14, wherein the tibial alignment guide is configured to wrap around an anterior-medial edge of the tibial surface when positioned on the tibia.

16. The orthopedic system of claim 13, further comprising a distal cutting block mountable to the one or more pins.

17. The orthopedic system of claim 13, wherein the femoral alignment guide has a distal guide aperture, and wherein the femoral alignment guide is configured to position the distal guide aperture at a distal portion of the femoral surface at one of a distal-lateral portion of a medial condyle and a distal-medial portion of a lateral condyle of the femur when the femoral alignment guide is positioned on femur.

18. The orthopedic system of claim 13, wherein the femoral alignment guide is configured to position the at least one guide aperture at one of an anterior or anterior-medial portion of the femoral surface when the femoral alignment guide is positioned on the femur.

19. The orthopedic system of claim 13, wherein the femoral alignment guide is configured to position the at least one guide aperture at one of a medial portion of a medial condyle and a lateral portion of a lateral condyle of the femur.

20. The orthopedic system of claim 13, wherein the three-dimensional curved inner surface of the femoral alignment guide is configured to nestingly conform and match with one or more of articular cartilage covering the femoral surface and a bone portion underlying the femoral surface.

* * * * *